United States Patent [19]
Vesely et al.

[11] Patent Number: 6,019,725
[45] Date of Patent: Feb. 1, 2000

[54] THREE-DIMENSIONAL TRACKING AND IMAGING SYSTEM

[75] Inventors: Ivan Vesely, Cleveland Heights, Ohio; Wayne L. Smith, London, Canada

[73] Assignee: Sonometrics Corporation, London, Canada

[21] Appl. No.: 08/813,662

[22] Filed: Mar. 7, 1997

Related U.S. Application Data

[63] Continuation-in-part of application No. PCT/CA96/00194, Mar. 24, 1996, which is a continuation-in-part of application No. 08/411,959, Mar. 28, 1995, Pat. No. 5,515,853.

[51] Int. Cl.[7] .................................................. A61B 8/00
[52] U.S. Cl. .......................................... 600/447; 128/916
[58] Field of Search ............................ 128/653.1, 653.2, 128/660.08, 661.01, 661.04, 696, 916; 382/128, 285; 73/625, 626

[56] References Cited

U.S. PATENT DOCUMENTS

| | | |
|---|---|---|
| 4,173,228 | 11/1979 | VanSteenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |
| 4,922,912 | 5/1990 | Watanabe . |
| 4,932,414 | 6/1990 | Coleman et al. ............. 128/660.09 |
| 4,940,064 | 7/1990 | Desai . |
| 4,945,305 | 7/1990 | Blood . |
| 5,000,190 | 3/1991 | Petre . |

(List continued on next page.)

FOREIGN PATENT DOCUMENTS

| | | |
|---|---|---|
| 92301264 | 2/1992 | European Pat. Off. . |
| US94/08352 | 7/1994 | WIPO . |
| US94/11298 | 10/1994 | WIPO . |
| US95/01103 | 1/1995 | WIPO . |

OTHER PUBLICATIONS

Davis J.W., Improved Arrival Time Detection for Cardiac Pulse Transit Sonomicrometry, *Computers in Cardiology 1996*, pp. 145–459, 1996.

Morse, Wayne, Medical Electronics, *IEEE Spectrum*, pp. 99–102, Jan. 1997.

Josephson et al., Comparison of Endocardial Cathether Mapping with Intraoperative Mapping of Ventricular Tachycardia, *Circulation*, vol. 61, No. 2, pp. 395–404, 1980.

Josephson et al., Ventricular Tachycardia during Endocardial Pacing. II. Role of Pace–Mapping to Localize Origin of Ventricular Tachycardia, *The American Journal of Cardiology*, vol. 50, pp. 11–22, Jul. 1982.

(List continued on next page.)

*Primary Examiner*—George Manuel
*Attorney, Agent, or Firm*—Benesch, Friedlander, Coplan & Aronoff LLP

[57] ABSTRACT

A 3-D tracking and imaging system (1600) for tracking the position of a surgical instrument (e.g., a catheter, probe, a sensor, needle or the like) inserted into a body, and displaying a 3-D image showing the position of the surgical instrument in reference to a 3-D image of the environment surrounding the surgical instrument. The 3-D tracking and imaging system (1600) aiding a physician in the guidance of the surgical instrument inside the body.

20 Claims, 68 Drawing Sheets

U.S. PATENT DOCUMENTS

| | | |
|---|---|---|
| 5,012,814 | 5/1991 | Mills et al. . |
| 5,016,173 | 5/1991 | Kenet et al. ............................ 382/128 |
| 5,025,786 | 6/1991 | Siegel . |
| 5,041,973 | 8/1991 | Lebron et al. . |
| 5,042,486 | 8/1991 | Pfeiler et al. . |
| 5,054,492 | 10/1991 | Scribner et al. . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,295,484 | 3/1994 | Marcus et al. . |
| 5,297,549 | 3/1994 | Beatty et al. . |
| 5,341,807 | 8/1994 | Nardella . |
| 5,357,956 | 10/1994 | Nardella . |
| 5,391,199 | 2/1995 | Ben-Haim . |
| 5,443,489 | 8/1995 | Ben-Haim . |
| 5,480,422 | 1/1996 | Ben-Haim . |
| 5,515,853 | 5/1996 | Smith et al. . |
| 5,517,990 | 5/1996 | Kalfas et al. . |
| 5,546,951 | 8/1996 | Ben-Haim . |

OTHER PUBLICATIONS

Witkowski et al., An Automated Simultaneous Transmural Cardiac Mapping System, *American Journal of Physiology*, vol. 247, pp. H661–H668, 1984.

Fann et al., Endocardial Activation Mapping and Endocardial Pace–Mapping Using a Balloon Apparatus, *American Journal of Cardiology*, vol. 55, pp. 1076–1083, Apr. 1, 1985.

Tweddell et al., Potential Mapping in Septal Tachycardia: Evaluation of a New Intraoperative Mapping Technique; *Circulation*, vol. 80 (Supplement I), No. 3, pp. I–97–I–108, Sep. 1989.

Hauer et al., Endocardial Catheter Mapping: Wire Skeleton Techniques for Representation of Computed Arrhythmogenic Sites Compared with Intraoperative Mapping, *Circulation*, vol. 74. No. 6. pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *Pace*, vol. II, pp. 449–459, Apr. 1988.

Jackman et al., New Catheter Techniques for Recording Left Free–Wall Accessory Atrioventricular Pathway Activation, *Circulation*, vol. 78, No. 3, pp. 598–611, Sep. 1988.

Shenasa et al., Cardia Mapping, Part I: Wolff–Parkinson–White Syndrome, *Pace*, vol. 13, pp. 223–230, Feb. 1990.

Scheinman et al., Current Role of Catheter Ablative Procedures in Patients with Cardiac Arrhythmias, *Circulation*, vol. 83, No. 6, pp. 2146–2153, Jun. 1991.

Buckles et al., Computer–Enhanced Mapping of Activation Sequences in the Surgical Treatment of Supraventricular Arrhythmias, *Pace*, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, *Journal of American College of Cardiologists*, vol. 17, No. 2, pp. 403–408, Feb. 1991.

Kaltenbrunner et al., Epicardial and Endocardial Mapping of Ventricular Tachycardia in Patients with Myocardial Infarction, *Circulation*, vol. 83, No. 3, pp. 1058–1071, Sep. 1991.

Masse et al., A Three–Dimensional Display for Cardiac Activation Mapping, *Pace*, vol. 14, Pt. 1, pp. 538–545, Apr. 1991.

Desai et al., Orthogonal Electrode Catheter Array for Mapping of Endocardial Focal Site of Ventricular Activation, *Pace*, vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, *Pace*, vol. 15, pp. 854–858, Jun. 1992.

Chen et al., Reappraisal of Electrical Cure of Atrioventricular Nodal Reentrant Tachycardia—Lesions from a Modified Catheter Albation Technique, *International Journal of Cardiology*, vol. 37, pp. 51–60, 1992.

Chen et al., Radiofrequency Catheter Ablation For Treatment of Wolff–Parkinson–White Syndrome–Short–and Long–Term Follow–up, *International Journal of Cardiology*, vol. 37, pp. 199–207, 1992.

Scheinman, North American Society of Pacing and Electrophysiology (NASPE)Survey on Radiofrequency Catheter Ablation: Implications for Clinicians, Third Party Insurers, and Government Regulatory Agencies, *Pace*, vol. 15, pp. 2228–2231, Dec. 1992.

Silka et al., Phase Image Analysis of Anomalour Ventricular Activation in Petiatric Patients with Pre–excitation Syndromes or Ventricular Tachycardia, *American Heart Journal*, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, *Lea & Febiger*, Malvern, Pa., 1993.

Holt et al., Ventricular Arrhythmias—A Guide to Their Localization, *British Heart Journal*, vol. 53, pp. 417–430, 1985.

Joseph et al., Role of Catheter Mapping in the Preoperative Evaluation of Ventricular Tachycardia, *American Journal of Cardiology*, vol. 40, pp. 207–220, Jan. 1982.

Kucher et al., Electrocardiographic Localization of the Site of Ventricular Tachycardia in Patients with Prior Myocardial Infarction, *JACC*, vol. 13, No. 4 pp. 893–900.

Page, Surgical Treatment of Ventricular Tachycardia: Regional Cryoablation Guided by Computerized Epicardial and Endocardial Mapping, *Circulation*, vol. 80, (Supplement I), No. 3, pp. I124–I–134, Sep. 1989.

| FIG.2A. | FIG.2C. |
|---|---|
| FIG.2B. | FIG.2D. |

FIG.2.

|  | FIG.3A. | FIG.3B. | FIG.3C. |  |
|---|---|---|---|---|
| FIG.3D. | FIG.3E. | FIG.3F. | FIG.3G. |  |
| FIG.3H. | FIG.3I. | FIG.3J. | FIG.3K. |
| FIG.3L. | FIG.3M. | FIG.3N. |  |
| FIG.3O. | FIG.3P. | FIG.3Q. |  |

FIG.3.

| FIG.4A. | FIG.4B. | FIG.4C. | FIG.4D. |
|---|---|---|---|
| FIG.4E. | FIG.4F. | FIG.4G. | FIG.4H. |
| FIG.4I. | FIG.4J. | FIG.4K. | FIG.4L. |
| FIG.4M. | FIG.4N. | FIG.4O. | FIG.4P. |

FIG.4.

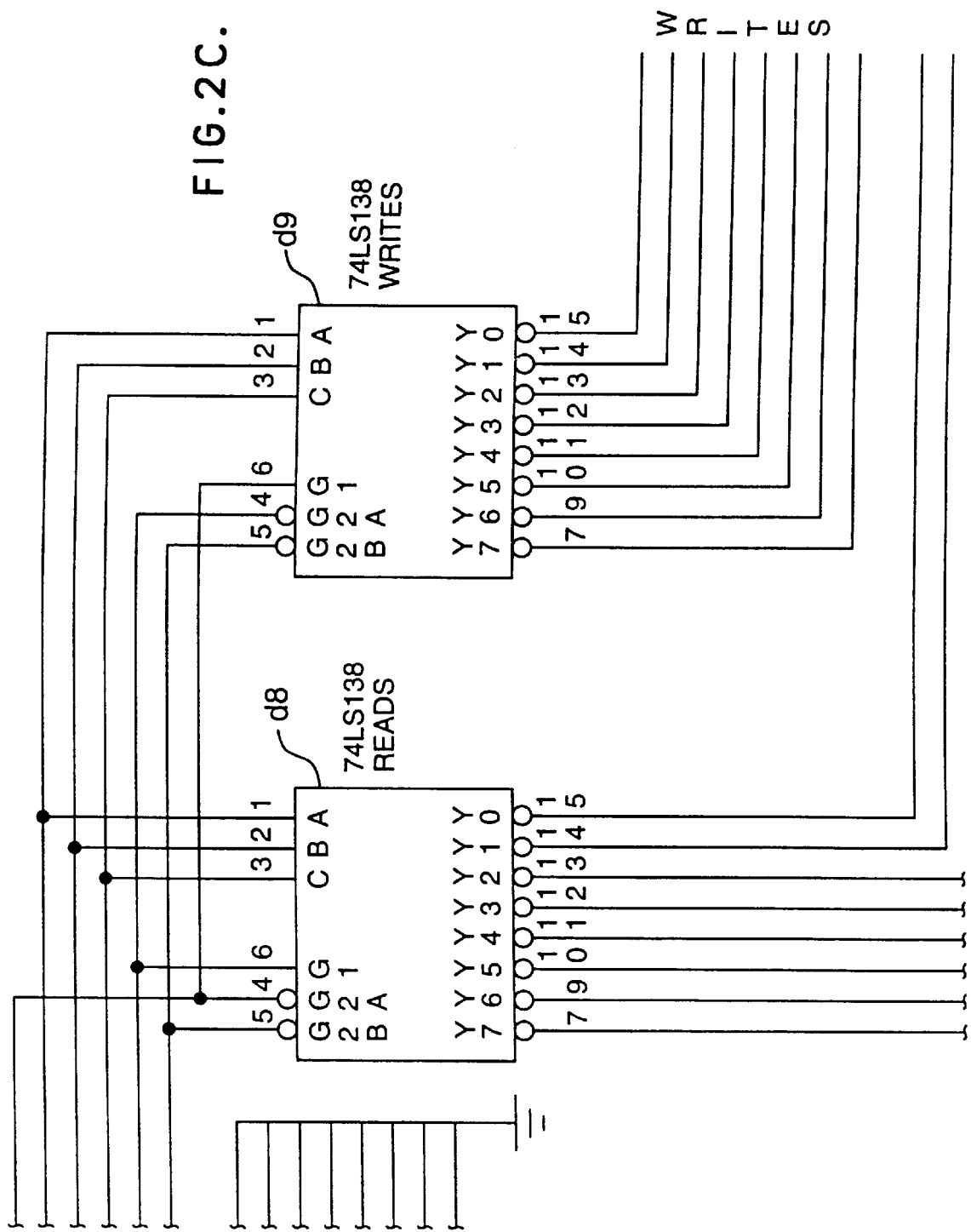

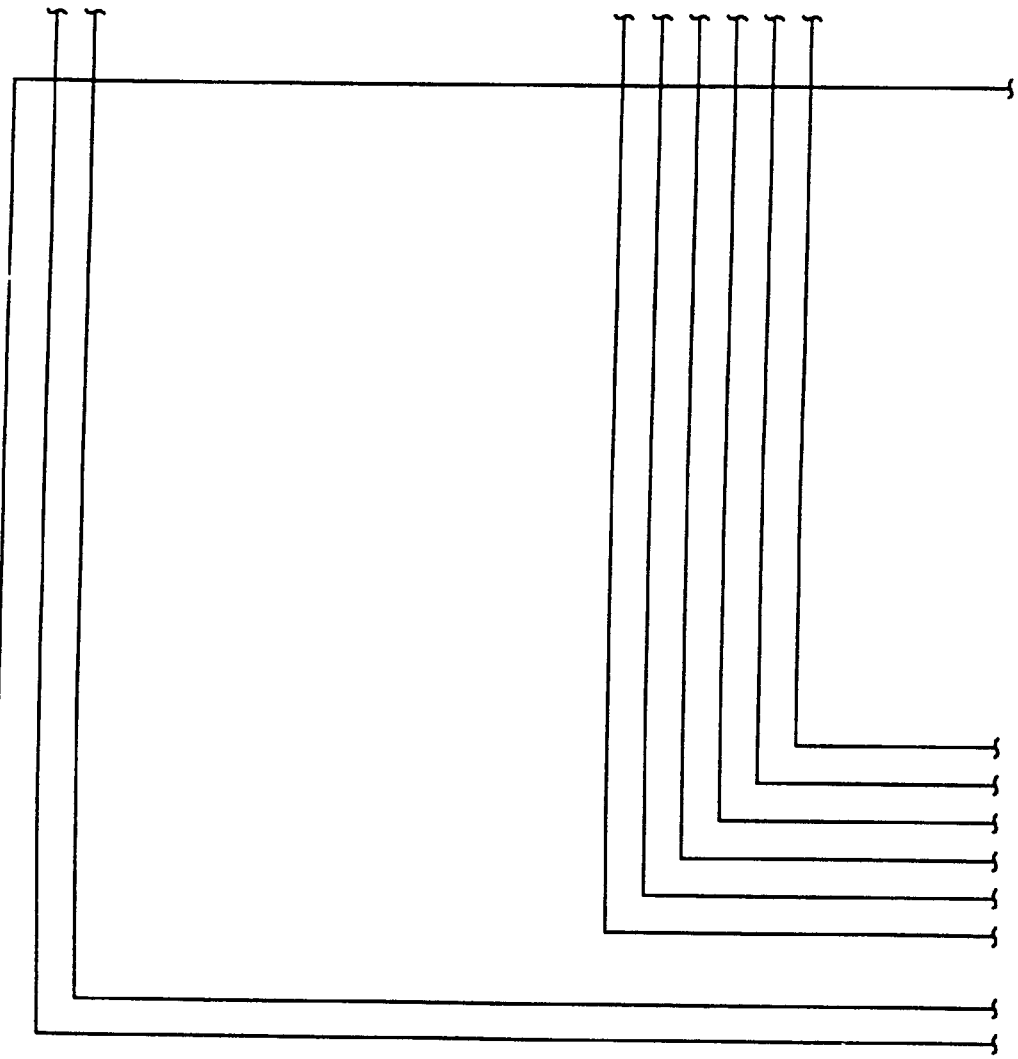

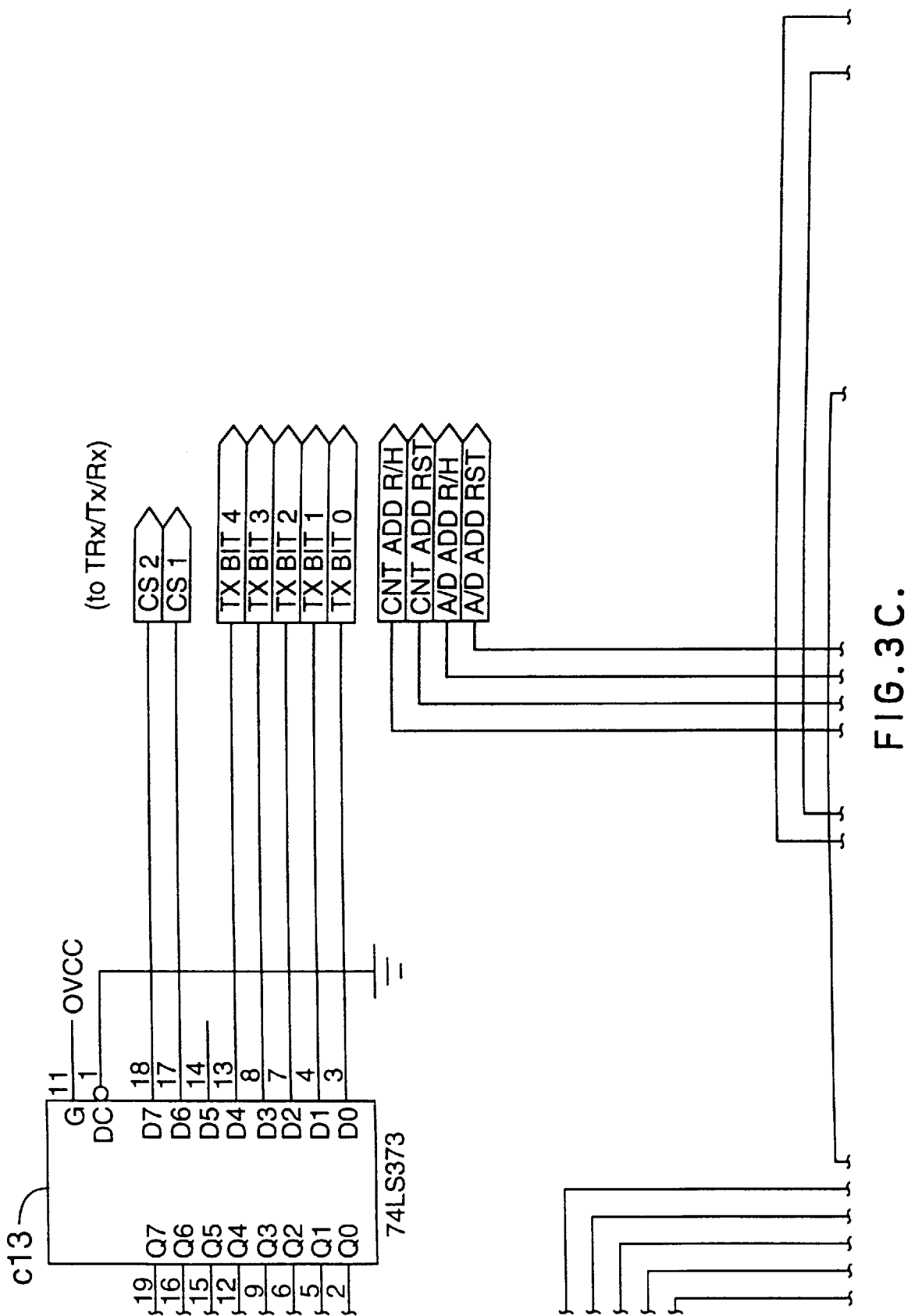

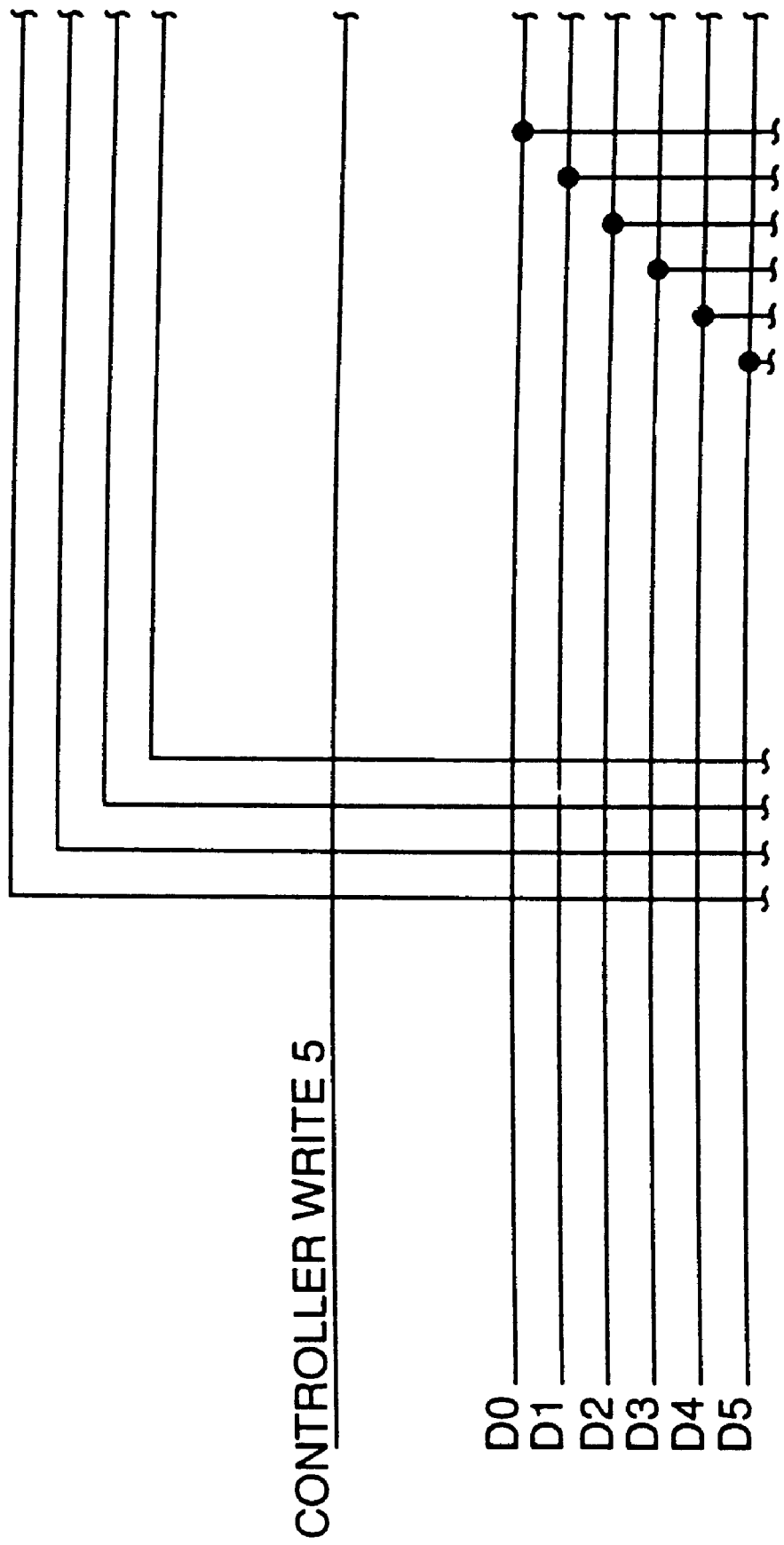

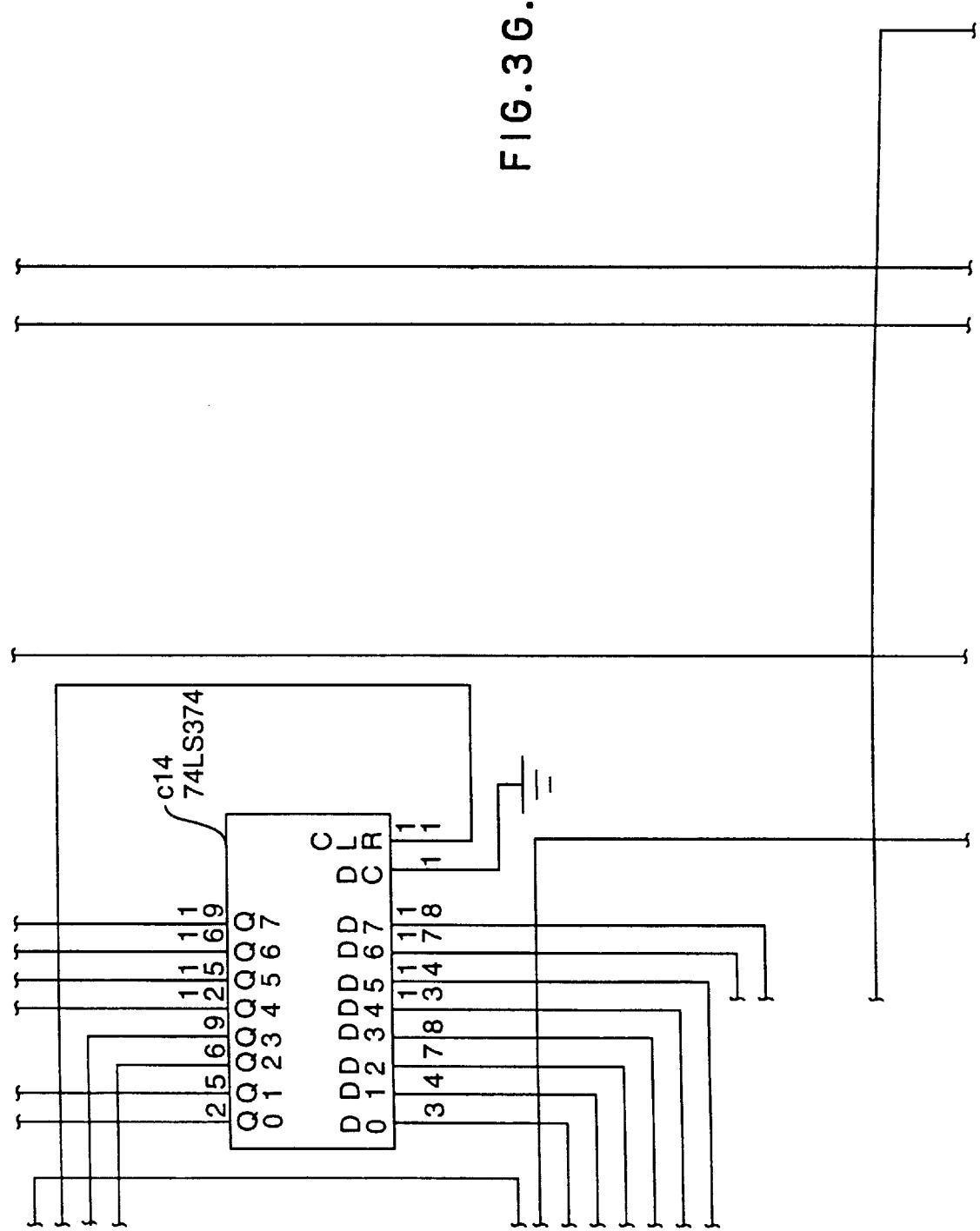

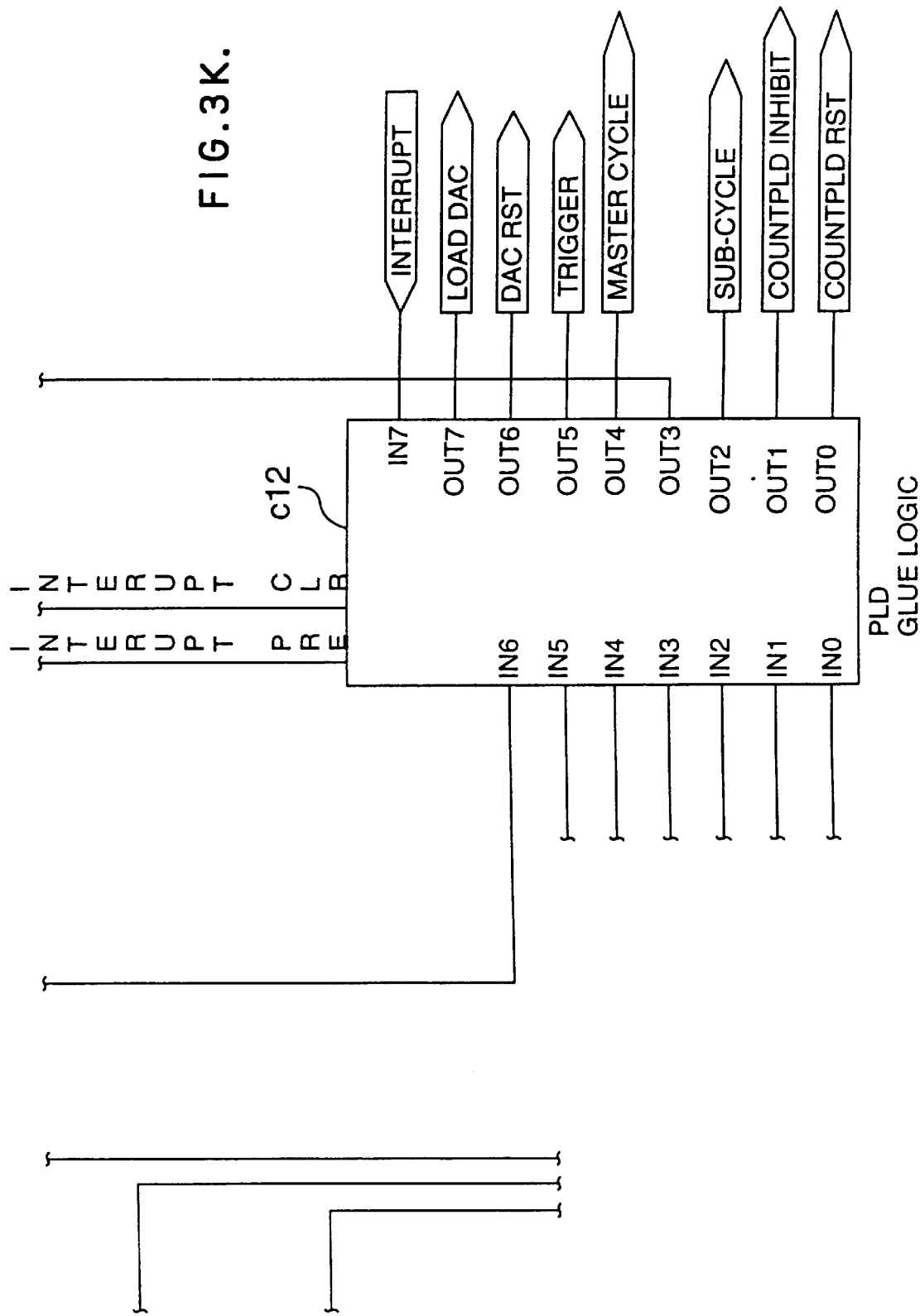

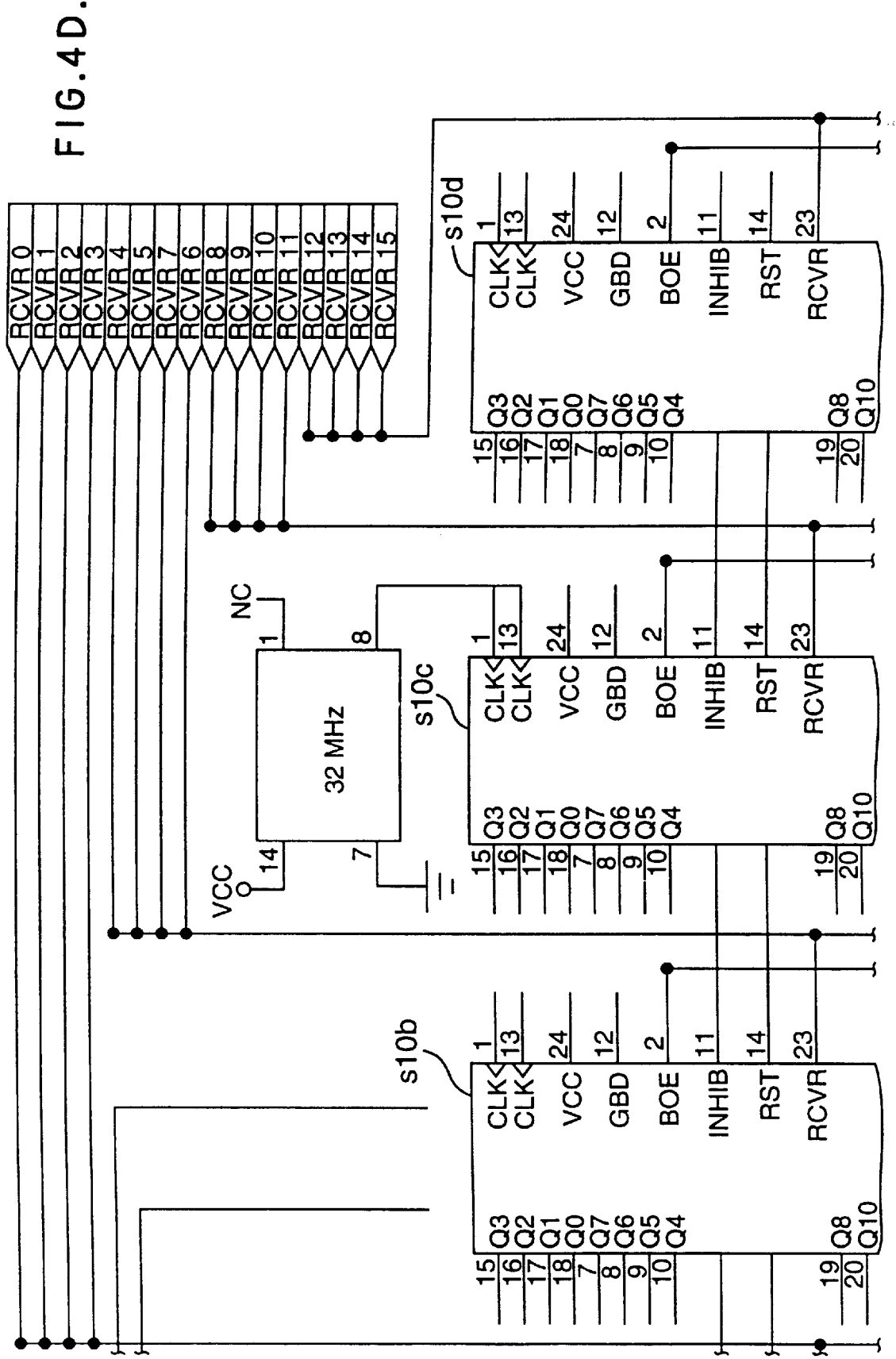

| | | |
|---|---|---|
| FIG.5A. | FIG.5B. | FIG.5C. |
| FIG.5D. | FIG.5E. | FIG.5F. |
| | | | |
|---|---|---|---|
| FIG.5G. | FIG.5H. | FIG.5I. | FIG.5J. |
| FIG.5K. | FIG.5L. | FIG.5M. | FIG.5N. |
FIG.5.
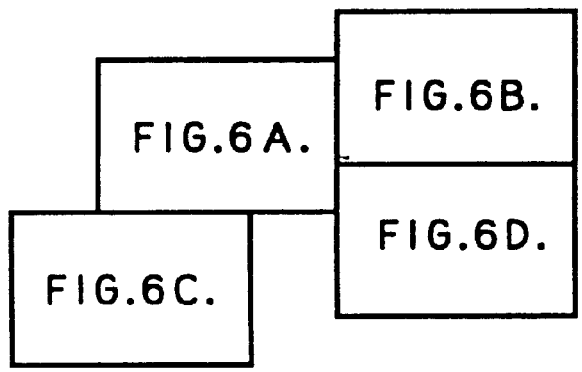
FIG.6.
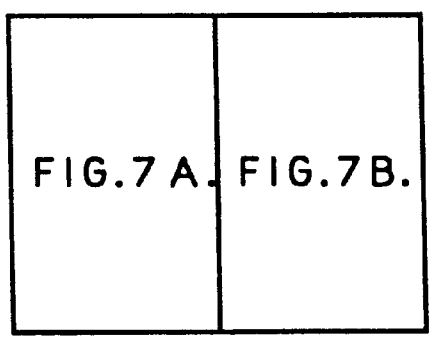
FIG.7.
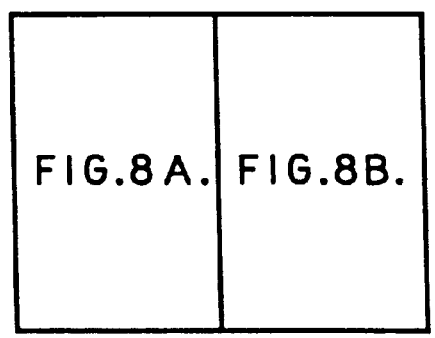
FIG.8.

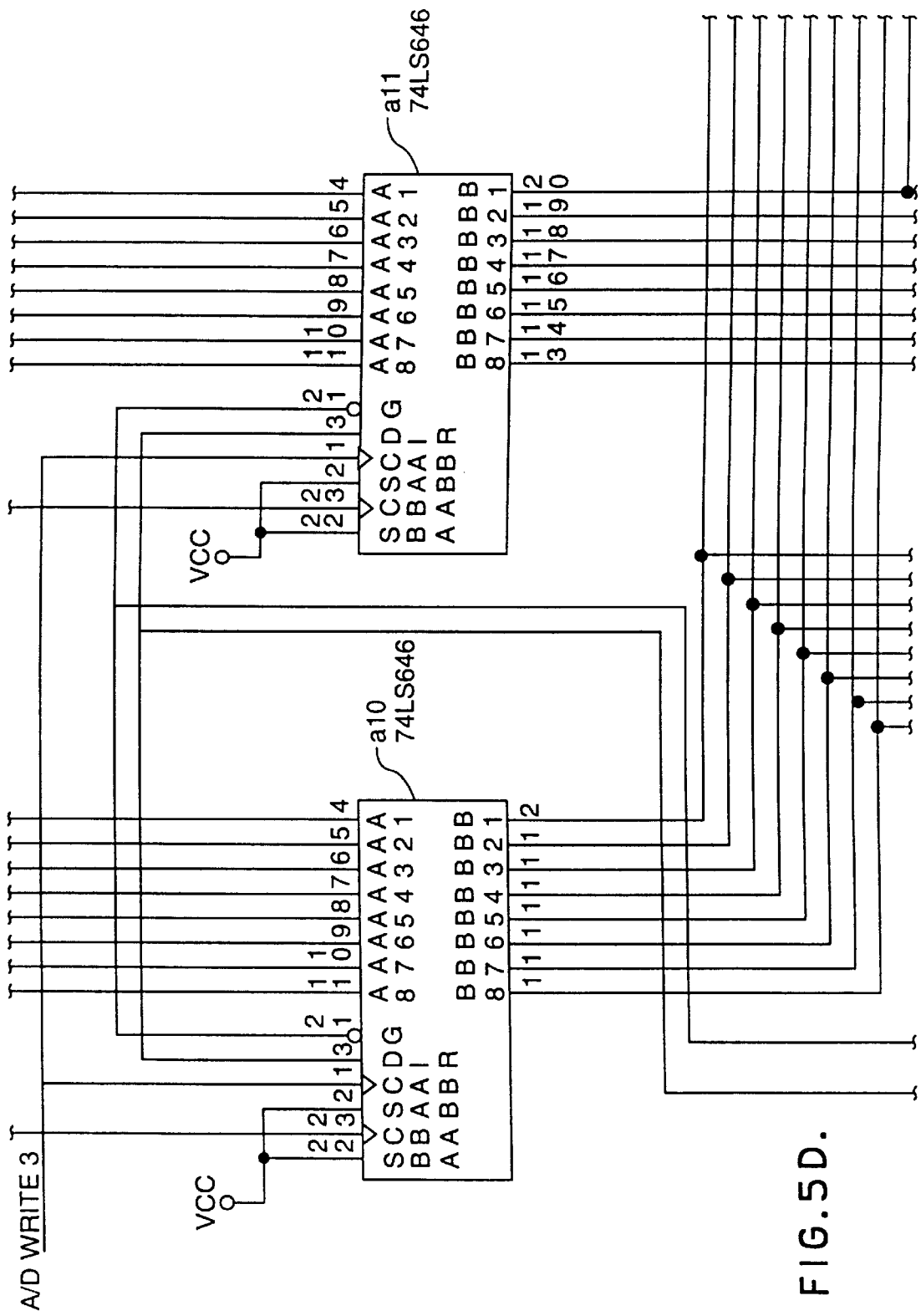

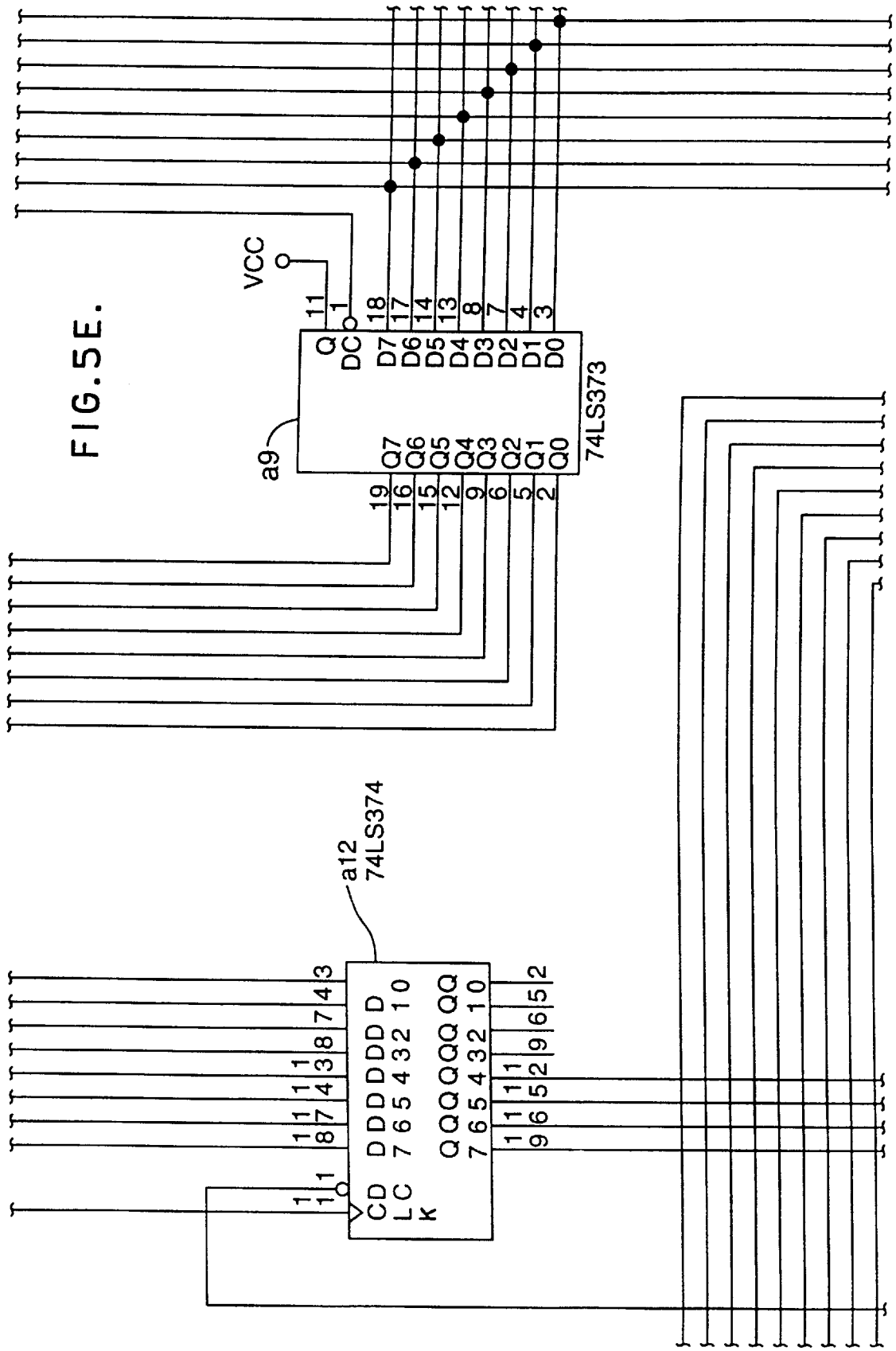

THREE-DIMENSIONAL TRACKING AND IMAGING SYSTEM

RELATED APPLICATIONS

The present application is a continuation-in-part (CIP) of co-pending PCT Application No. PCT/CA96/00194, filed Mar. 24, 1996, which is a continuation-in-part (CIP) of U.S. application Ser. No. 08/411,959 filed Mar. 28, 1995, now U.S. Pat. No. 5,515,853.

FIELD OF THE INVENTION

The present invention relates in general to a 3-D tracking and imaging system, and more particularly to a tracking system for tracking the position of a device by measuring distances in two or three dimensions using multiple transducers, and an imaging system for displaying a tracked device in 3-D space.

BACKGROUND OF THE INVENTION

Using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal), that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received.

Prior art ultrasound tracking systems suffer from a number of shortcomings which limit their utility. Firstly, conventional sonomicrometers use analog circuitry to transmit and receive signals (e.g., phase capacitative charging circuits). The voltage representing the measured distance is then output to a strip chart recorder in analog form. This data must then be digitized for computer analysis.

Secondly, conventional ultrasound tracking systems use analog potentiometers to adjust the inhibit time and the threshold voltage that triggers the receiver circuits. This often requires the use of an oscilloscope. Each time the tracking system is used, these settings must be manually set and adjusted in order to tune the system. This can be time consuming and annoying. As a whole, the function of the tracking system cannot be changed. The repetition frequency is fixed, regardless of the number of channels used, and the tracking system is therefore very limited in terms both of the distances that can be measured, and the temporal precision with which the tracking system operates.

Thirdly, conventional ultrasound tracking systems feature pairs of transmitter and receiver crystals that are energized sequentially at fixed repetition rates. As such, prior art tracking systems lack experimental flexibility. For example, before a pair of crystals is implanted in the medium (e.g., a bodily structure, such as a human organ), the user must decide the function of each crystal; similarly, the user must determine which distances are to be measured by which crystal pair. This can be awkward because surgery often necessitates changes during the procedure. If either of the receiver or transmitter crystals malfunctions, the distance between them cannot be measured. Critical measurements can therefore be lost after a significant amount of effort is put into setting up the surgery.

Fourthly, conventional ultrasound tracking systems measure only a straight line distance between any isolated pair of crystals. Three-dimensional information is therefore impossible to acquire. Even if multiple combinations of distances could somehow be linked together, the inherently analog nature of the data would necessitate the use of additional, complex hardware.

Finally, conventional ultrasound tracking systems use discrete elements, such as threshold capacitors and potentiometers requiring large plug-in units to increase the number of channels. The systems are very large, usually two feet wide by 18" deep, and up to 12" high. Additional hardware such as strip chart recorders must be used, for visualization and subsequent processing. This can be very awkward given the space constraints at busy research institutes and hospitals.

The present invention provides a unique and advantageous system for tracking the position of a device moving through a medium, and for displaying an image showing the position of the device in relation to the environment surrounding the device.

SUMMARY OF THE INVENTION

According to the present invention there is provided a three-dimensional tracking and imaging system which provides enhanced functionality for diverse clinical and medical research applications.

The 3-D tracking and imaging system of the present invention uses modern day digital electronics in conjunction with an integrated personal computer. External A/D converters are not required, as the data is acquired digitally, directly from the sensors. Due to the speed of the controlling computer, the tracking system of this invention is capable of detecting distance increments as small as 19 $\mu$m. The acquired data can be displayed on the computer screen as it is being obtained, and can be saved to the computer's storage media with a simple key stroke. After an experiment or surgical procedure, the saved data can be examined and manipulated according to the user's specifications.

According to a preferred embodiment of the present invention, virtually every function of the 3-D tracking and imaging system is digitally controlled, and therefore very flexible. To begin, a set-up menu is generated which allows the user to select which transducers are active as well as the function of each channel. Next, a data display program permits the parameters of the transducer to be customized for specific applications. For example, if very few channels are being used, the repetition frequency can be increased so that data can be acquired at several Khz. On the other hand, if the system is being used in vitro, where persistent echoes from a container vessel may present a problem, the repetition frequency can be reduced to allow the echoes to attenuate between successive measurements.

The duration of the power delivered to the transducers can be reduced for precision work or increased if greater distances are required to be measured. The duration of the delay required to overcome electromagnetic interference between transducer leads is adjustable by means of a variable inhibit feature. Additionally, the number of samples displayed and stored in any given data save is variable according to the length of time that a user's protocol demands. Finally, the resolution of the displayed information is variable in conjunction with the degree of motion of the measured specimen. All of these functions are controlled digitally by means of custom designed digital cards or modules discussed in greater detail below, which, in turn, are software controlled.

Additional customized software is included in the 3-D tracking and imaging system of the present invention for post processing and visualizing the acquired data. In these routines, stray data points can be easily removed, three point filters can be applied for smoothing, level shifts can remove areas of discontinuity, channels can be derived, beat analyses can be performed, and automatic minimum/maximum level sensing can be applied. Finally, routines can be provided that allow animated data points in a Cartesian coordinate system while providing volumetric and position information.

The 3-D tracking and imaging system of the present invention overcomes the limitation of prior art transducer pairs. The present system can work with many individual transducers that can be energized sequentially at very high repetition rates, thereby giving the impression that several distances are being measured instantaneously. In reality, the distances are measured in sequence, but since the delay time between successive measurements in the order of 100 microseconds, the measurements occur virtually simultaneously for most biological applications.

Additionally, the 3-D tracking and imaging system of the present invention provides the option of combining the transmitter and receiver circuitry into one transceiver. This provides a researcher with the freedom to affix an array of transducers to a test object (e.g., catheter, needle, probe, etc,) and then decide which transducers are to function as transmitters and which are to function as receivers. Moreover, this type of configuration does not need to be limited strictly to transmitter-receiver pairs. By using transceivers, the duty cycle between implanted transducers can automatically alternate between transmit and receive modes, so that every possible combination of distances between a group of transducers can be determined. This type of application is particularly useful for studies which require redundancy of measurement, as well as for establishing in vivo reference frames from which to base three-dimensional tracking.

The 3-D tracking and imaging system of the present invention is configurable into a true 3-D mode. In this configuration four or more transceivers are implanted within an object (i.e., specimen) in which distances are to be measured, thereby serving as a mobile reference frame. Multiple transmitters are then attached to the specimen at various locations. Since any three transceivers can send and receive signals, they essentially create an x,y plane. The fourth transceiver is then used to determine the z coordinate of the surrounding transducers by determining if the active transmitter lies above or below the reference plane.

Because the 3-D tracking and imaging system of the present invention uses modem day integrated circuitry and custom programmed logic chips, it is physically much smaller than prior art units. A large part of the system of the present invention is implemented within the user PC (personal computer). The entire unit is composed of three digital computer cards that plug directly into a standard AT computer mother board. A single cable connection connects the controlling computer and the discrete peripheral transmitter/receiver/transceiver unit. This convenient set-up drastically reduces the amount of experimental space required over prior art conventional units.

Moreover, the 3-D tracking and imaging system allows the position of a device being tracked to be displayed in relation to the surrounding environment using a 3-D template.

BRIEF DESCRIPTION OF THE DRAWINGS

A detailed description of the preferred embodiment is provided herein below with reference to the following drawings, in which:

FIG. 2, comprising FIGS. 2A, 2B, 2C and 2D, is a schematic diagram of a computer interface architecture used on all digital cards or modules of the preferred embodiment;

FIG. 3, comprising FIGS. 3A, 3B, 3C, 3D, 3E, 3F, 3G, 3H, 3I, 3J, 3K, 3L, 3M, 3N, 3O, 3P and 3Q is a schematic diagram of a controller card architecture according to the preferred embodiment;

FIG. 4, comprising FIGS. 4A, 4B, 4C, 4D, 4E, 4F, 4G, 4H, 4I, 4J, 4K, 4L, 4M, 4N, 4O and 4P, is a schematic diagram of a counter card architecture according to the preferred embodiment;

FIG. 5, comprising FIGS. 5A, 5B, 5C, 5D, 5E, 5F, 5G, 5H, 5I, 5J, 5K, 5L, 5M and 5N is schematic diagram of an A/D card architecture according to the preferred embodiment;

FIG. 6, comprising

FIG. 7, comprising

FIG. 8, comprising

DETAILED DESCRIPTION OF THE PREFERRED EMBODIMENT

Figure 1:
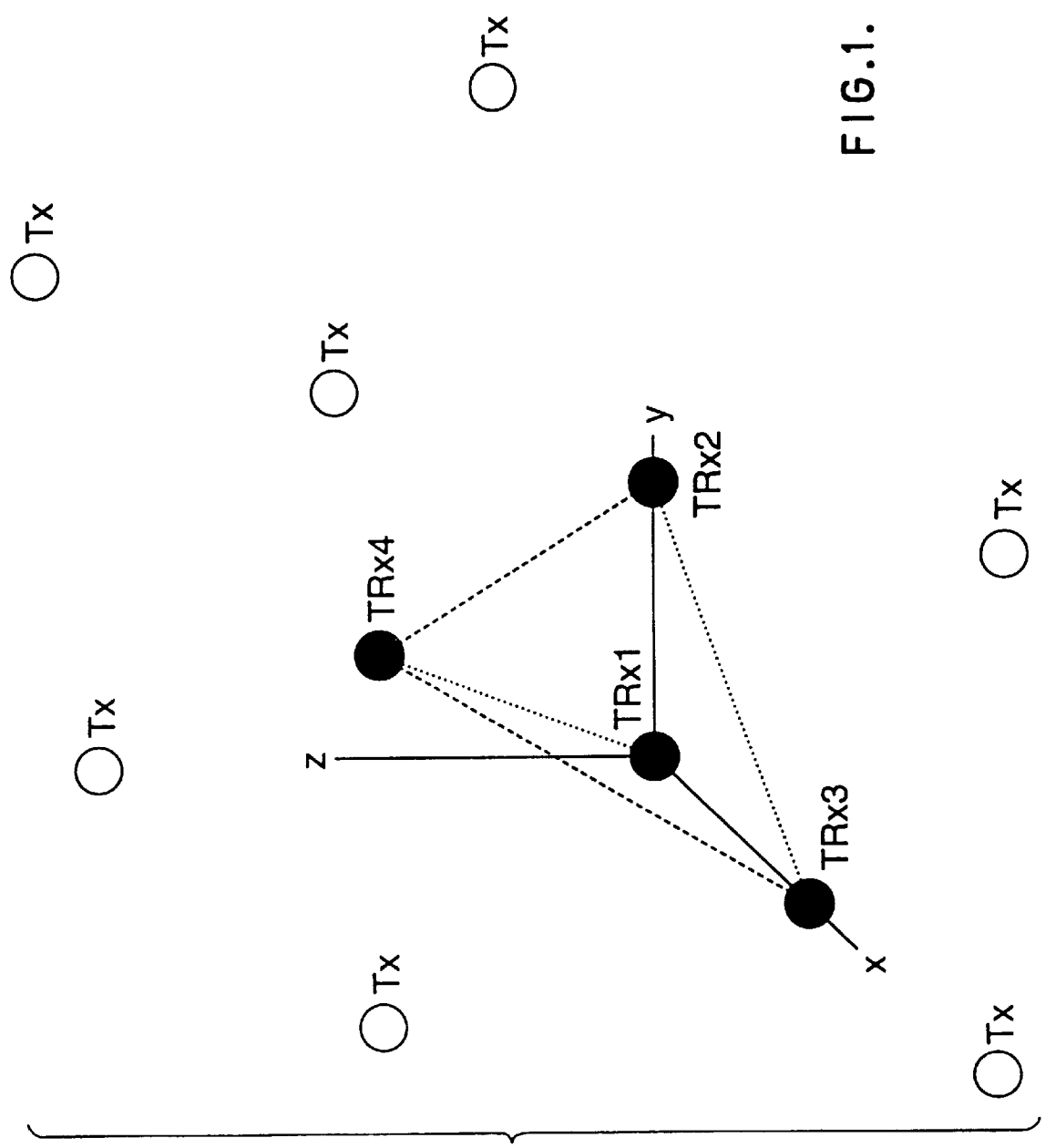
FIG. 1 is a schematic representation of four transducers in three-dimensional space, for tracking and triangulating the three-dimensional positions of each transducer, in accordance with the present invention.

As discussed above, the ultrasonic tracking system of the present invention utilizes a plurality of transceivers, each of which can be programmed to operate as a transmitter or a receiver. By utilizing four or more transceivers, full three-dimensional measurement capability is provided, as shown in FIG. 1. Any three transceivers (TRx1, TRx2 and TRx3) lay in a plane (i.e., the x,y plane). The fourth transceiver (TRx4) may then be used to determine the z coordinates of the surrounding transducers (i.e., multiple crystals Tx) by determining if an active one of the transmitter transducers lies above or below the reference plane established by transceivers TRx1, TRx2 and TRx3. Each of the many transmitters (Tx) attached to the specimens are sequentially fired, while all reference transceivers record the receiver signals. Since the distance from each transmitter to the reference plane created by the transceivers is known, the relative x, y, z, coordinates of the transmitters can be determined. This is done in real time on a personal computer (PC) with the use of triangulation. This method of networking the transducers is unique to the tracking system of the present invention, and permits the user to trace the three-dimensional motion of an object under investigation. Obviously, the greater the number of transmitters, the better is the reconstruction.

Specific applications of the ultrasonic tracking system which utilize three-dimensional tracking and triangulation, are discussed in greater detail below.

As indicated above, the ultrasonic 3-D tracking system according to the present invention is preferably fully integrated into the standard AT-style computer motherboard found in modern PCs. The three digital cards which comprise the majority of the hardware for the present invention, perform specific, modular functions in the overall operation of the unit. As such, each card is provided with a proper system interface structure in order to be compatible with the ISA architecture of the controlling processor.

Figure 2A:
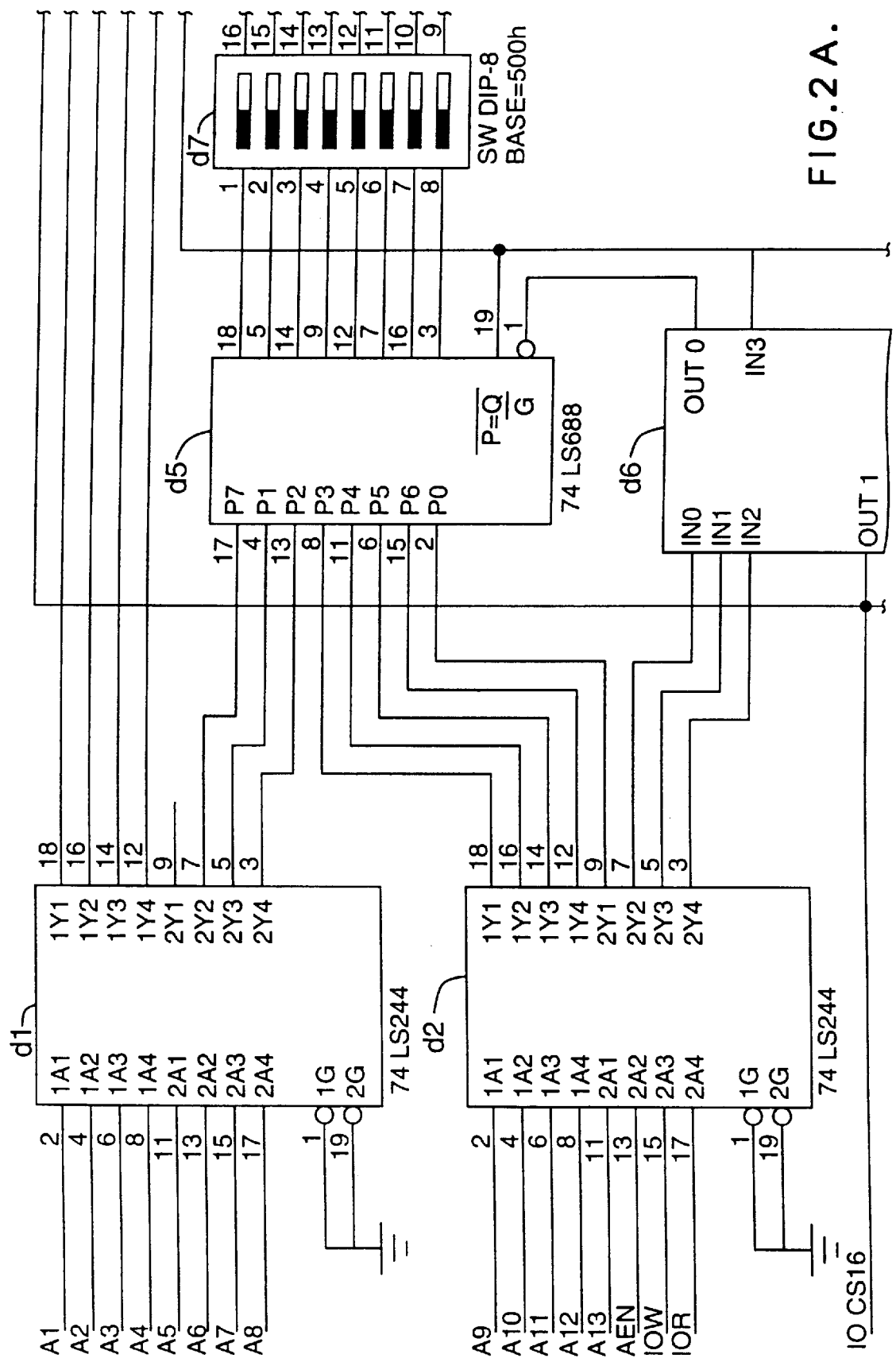
Figure 2B:
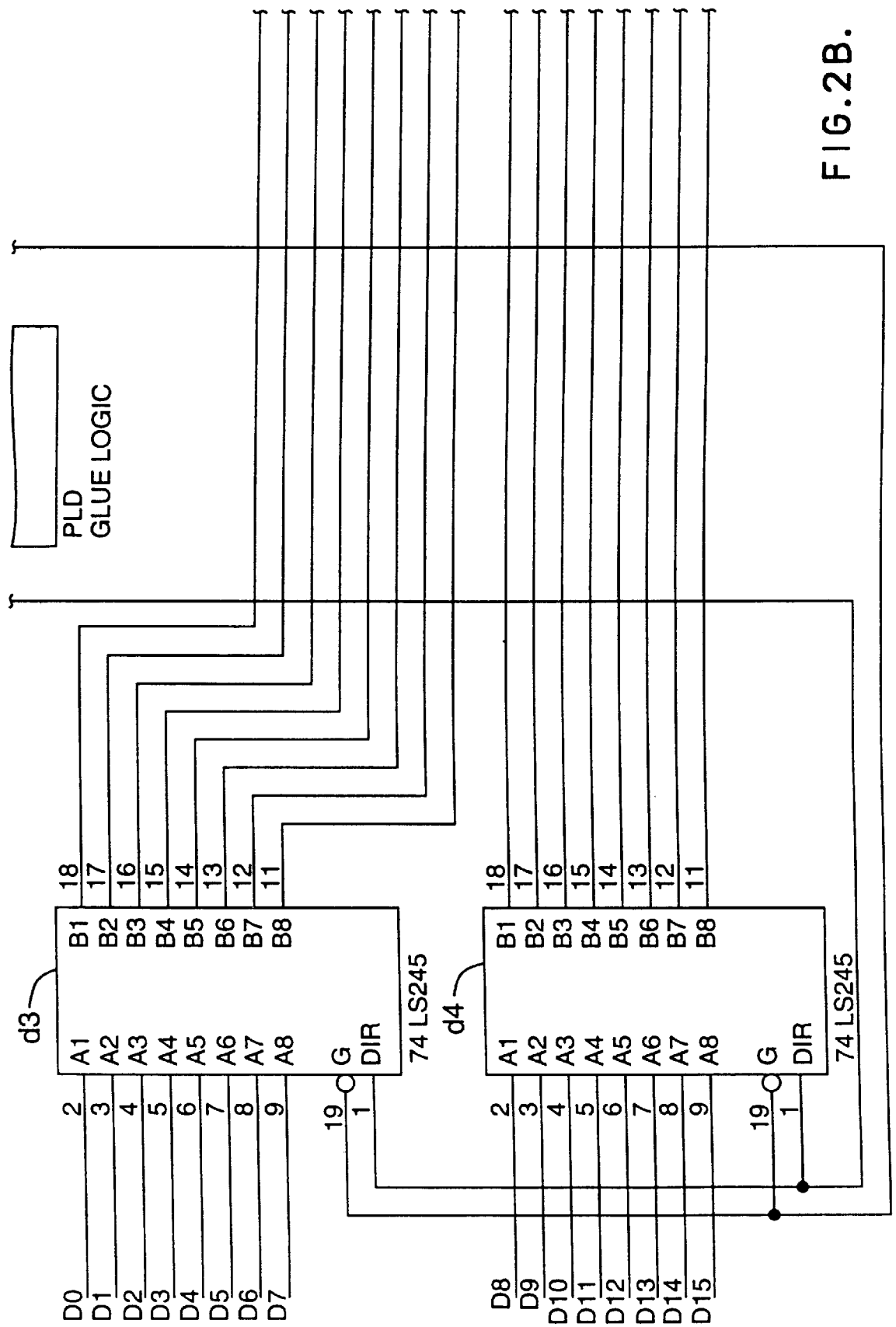
Figure 2D:
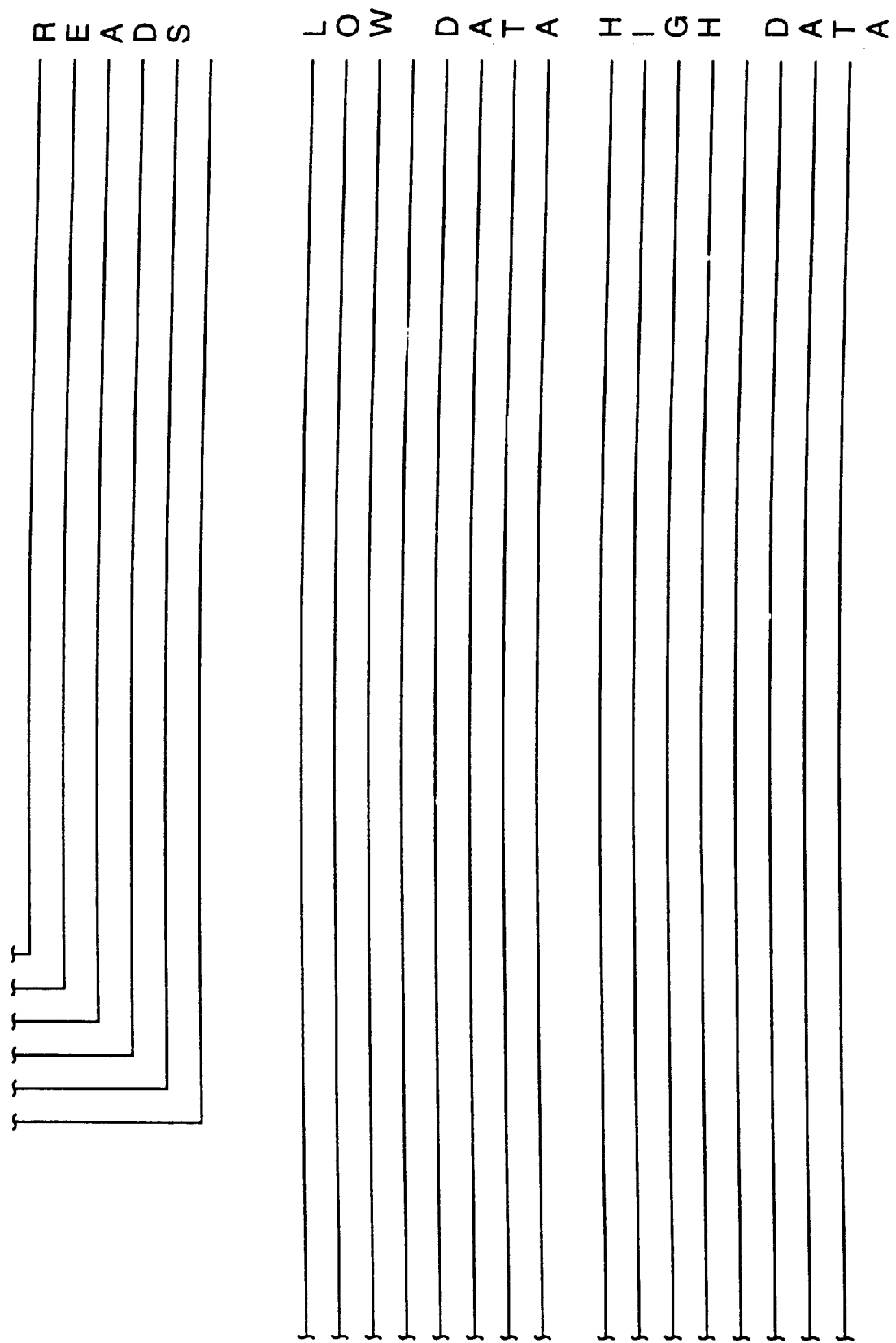
Figure 3B:
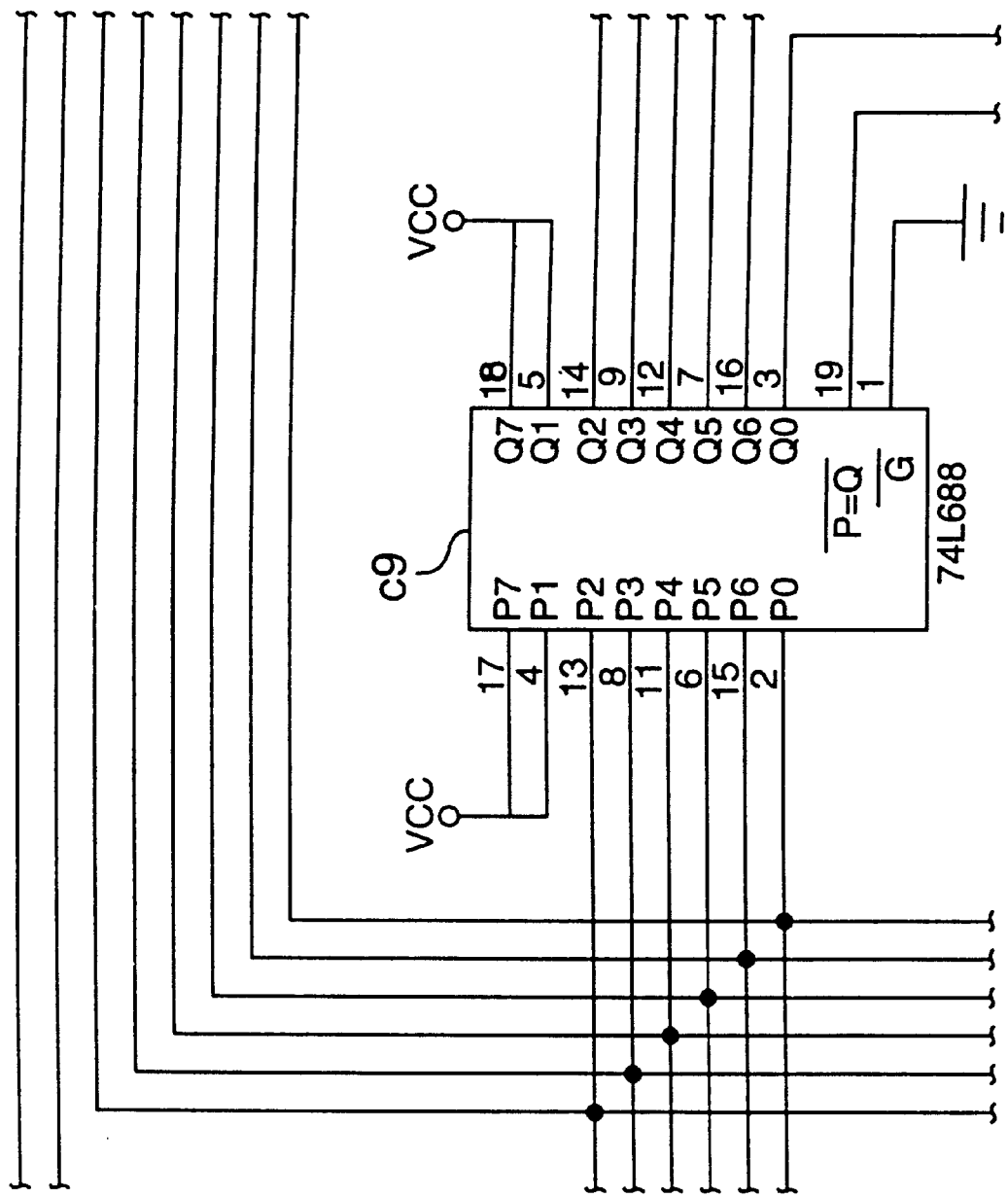
Figure 3E:
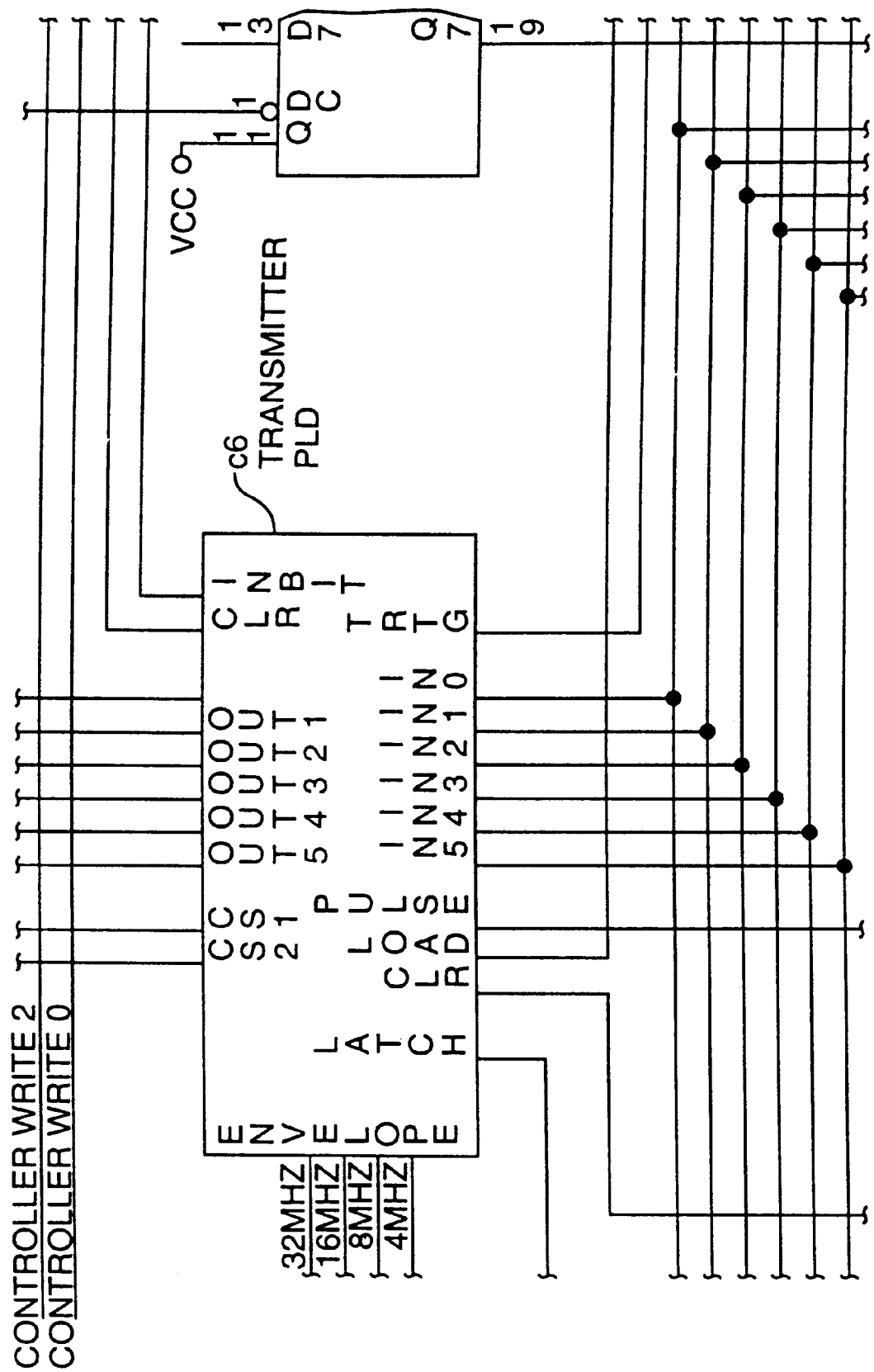
Figure 3F:
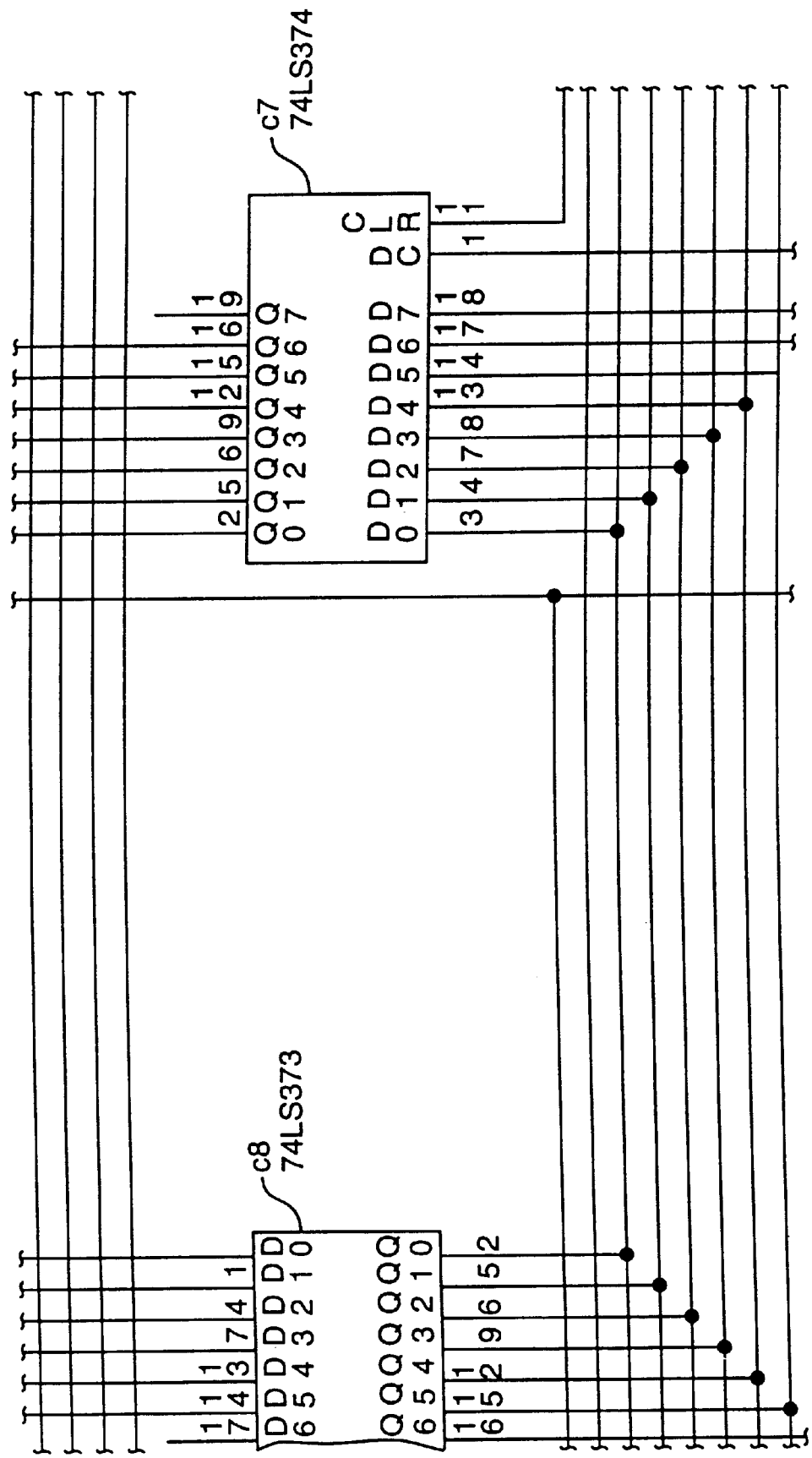
Figure 3H:
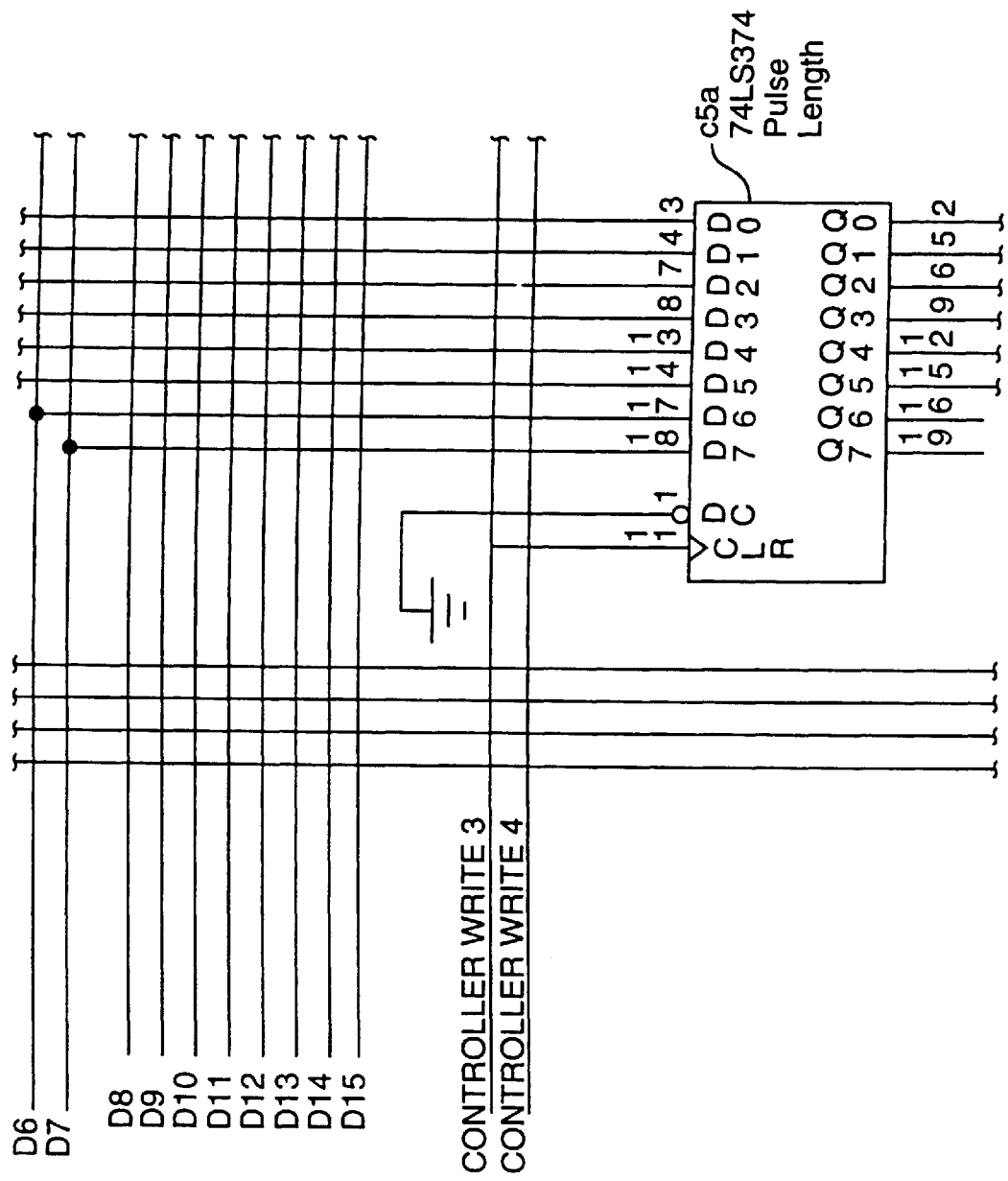
Figure 3I:
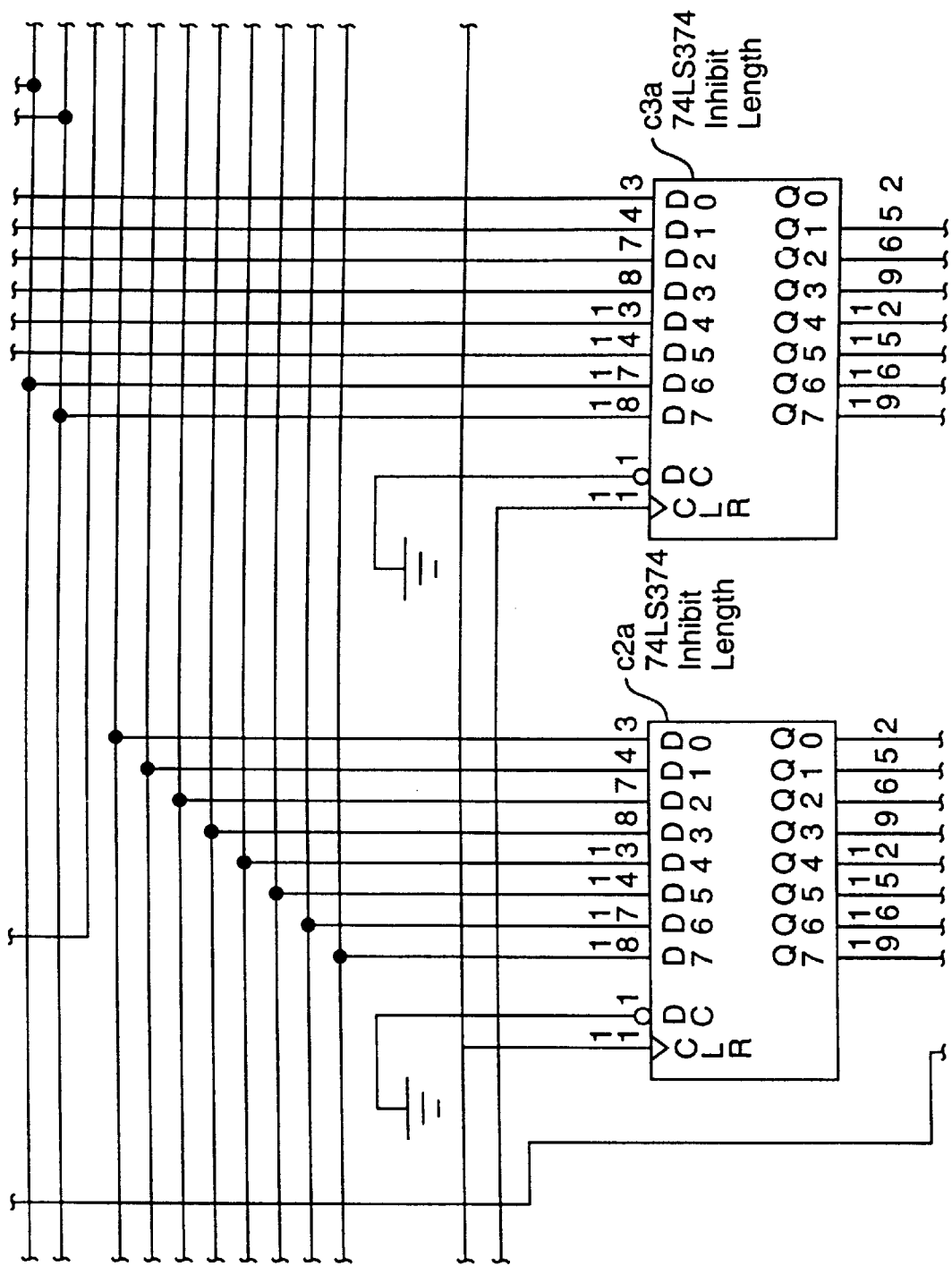
Figure 3J:
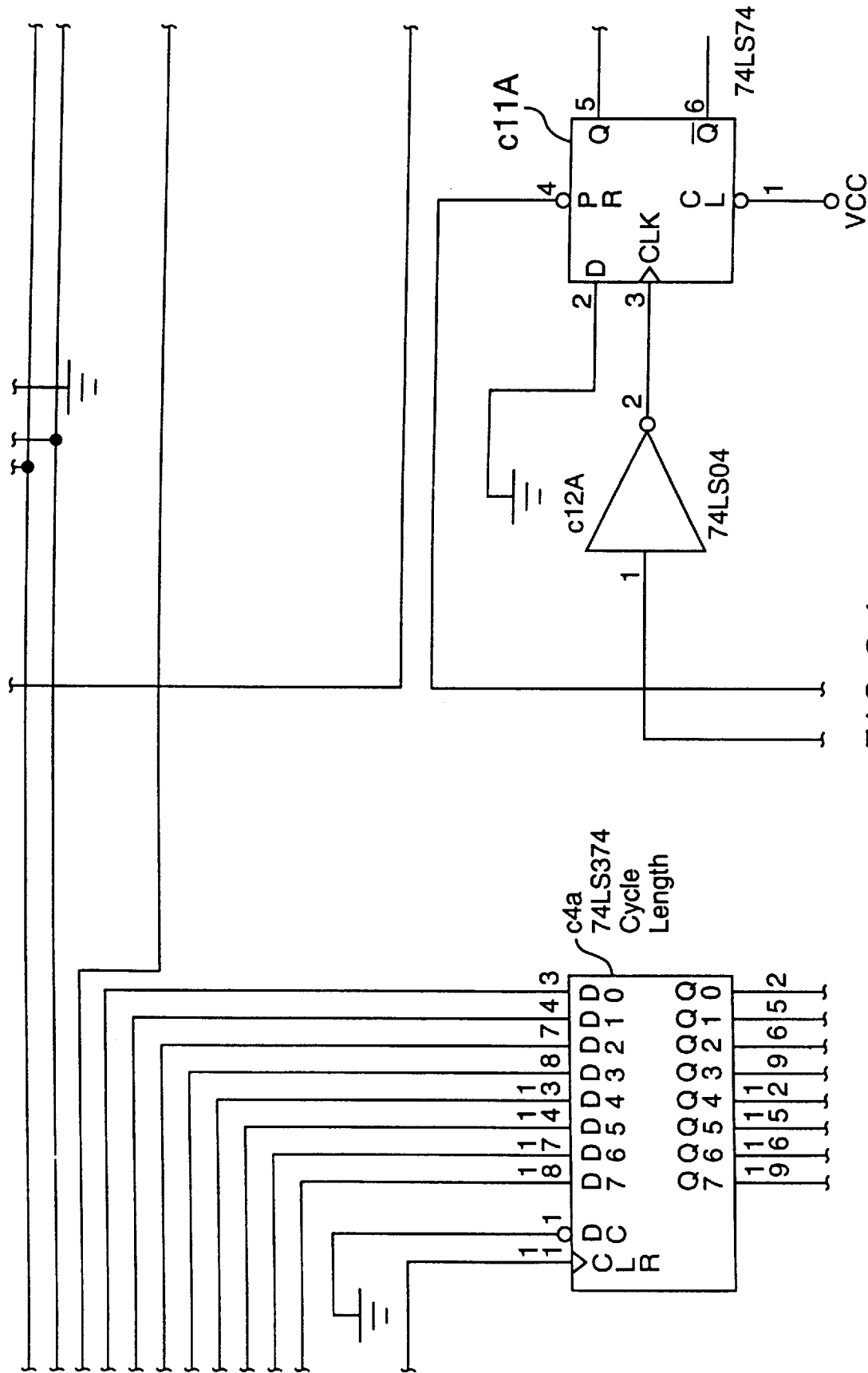
Figure 3L:
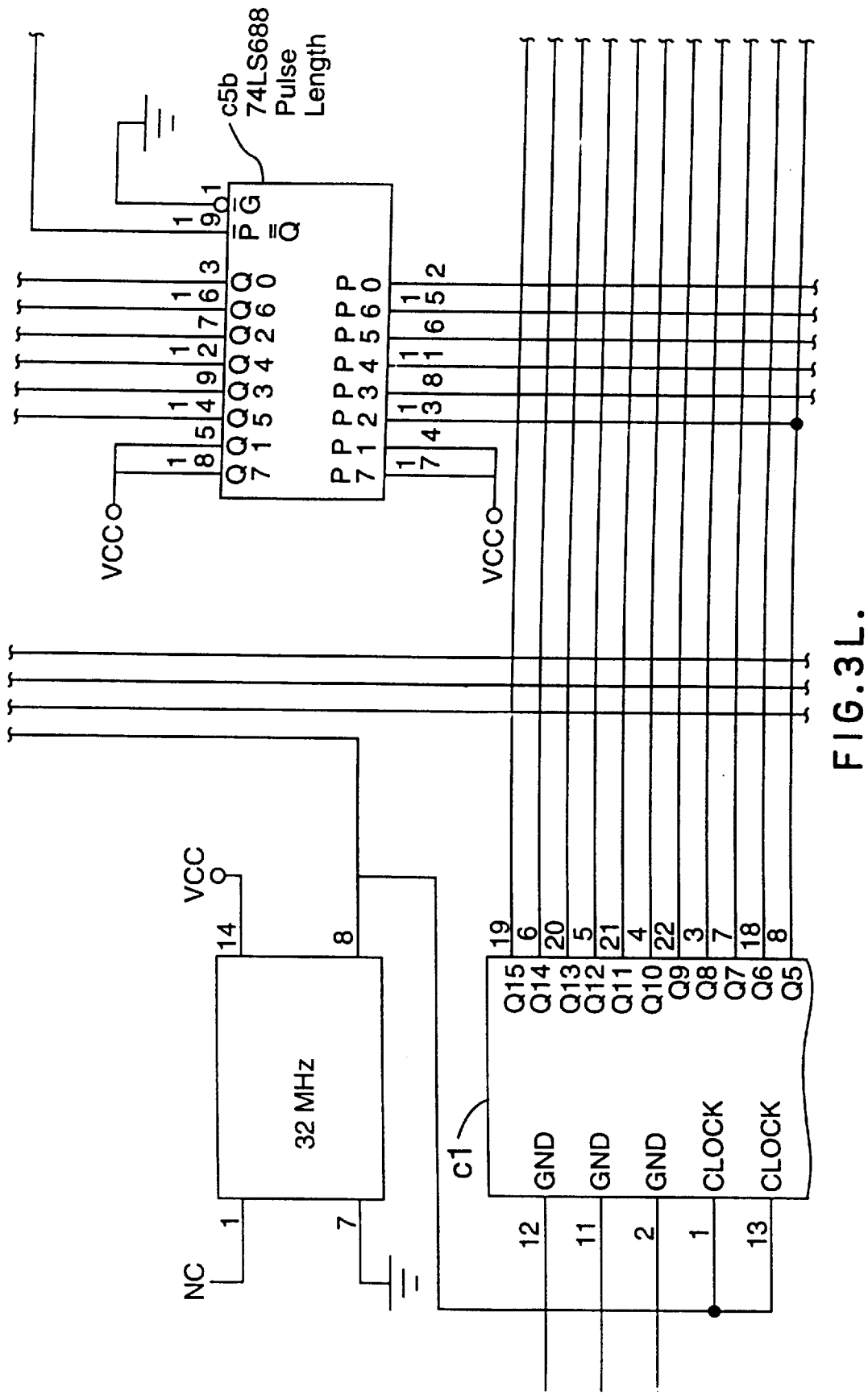
Figure 3M:
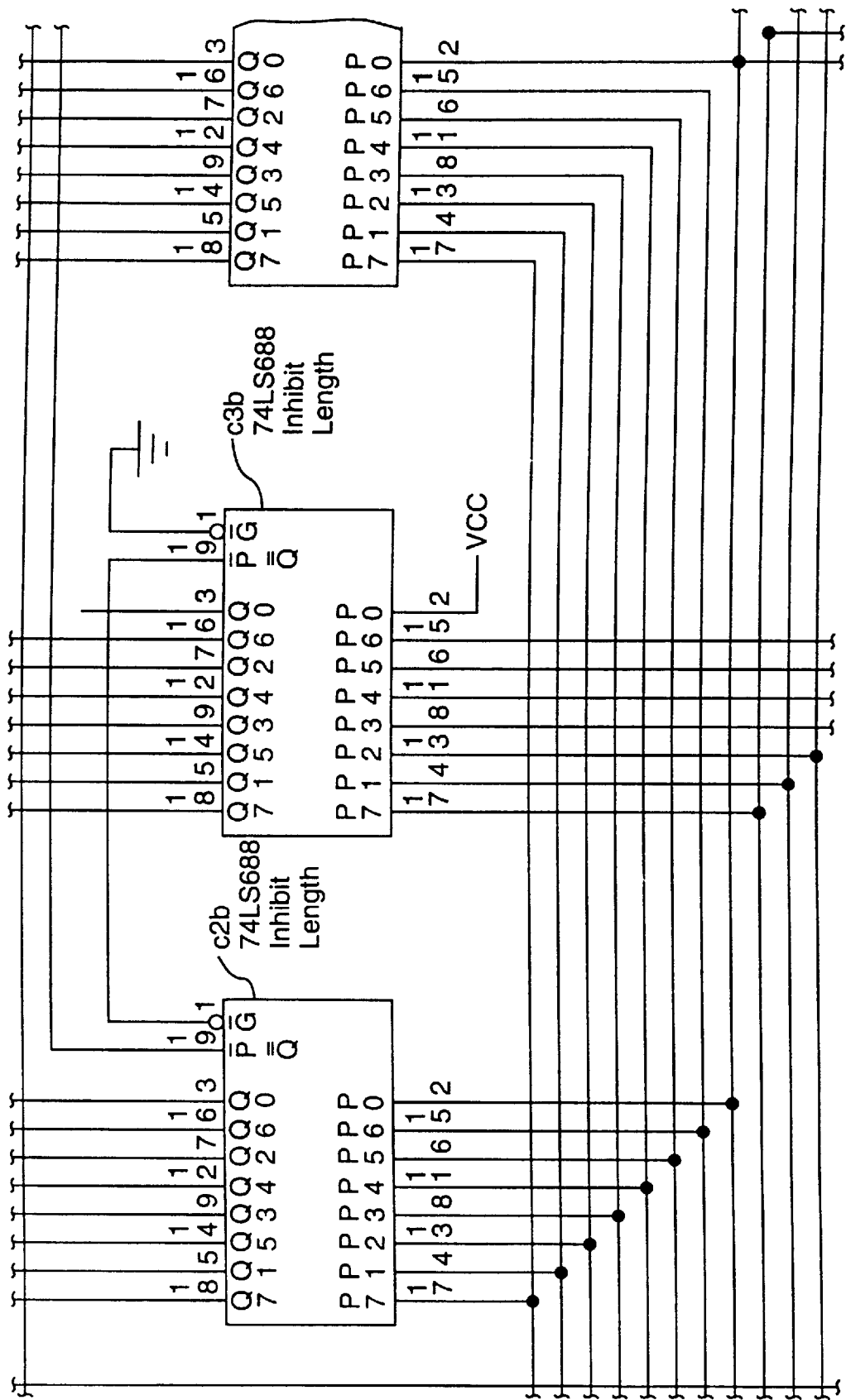
Figure 3N:
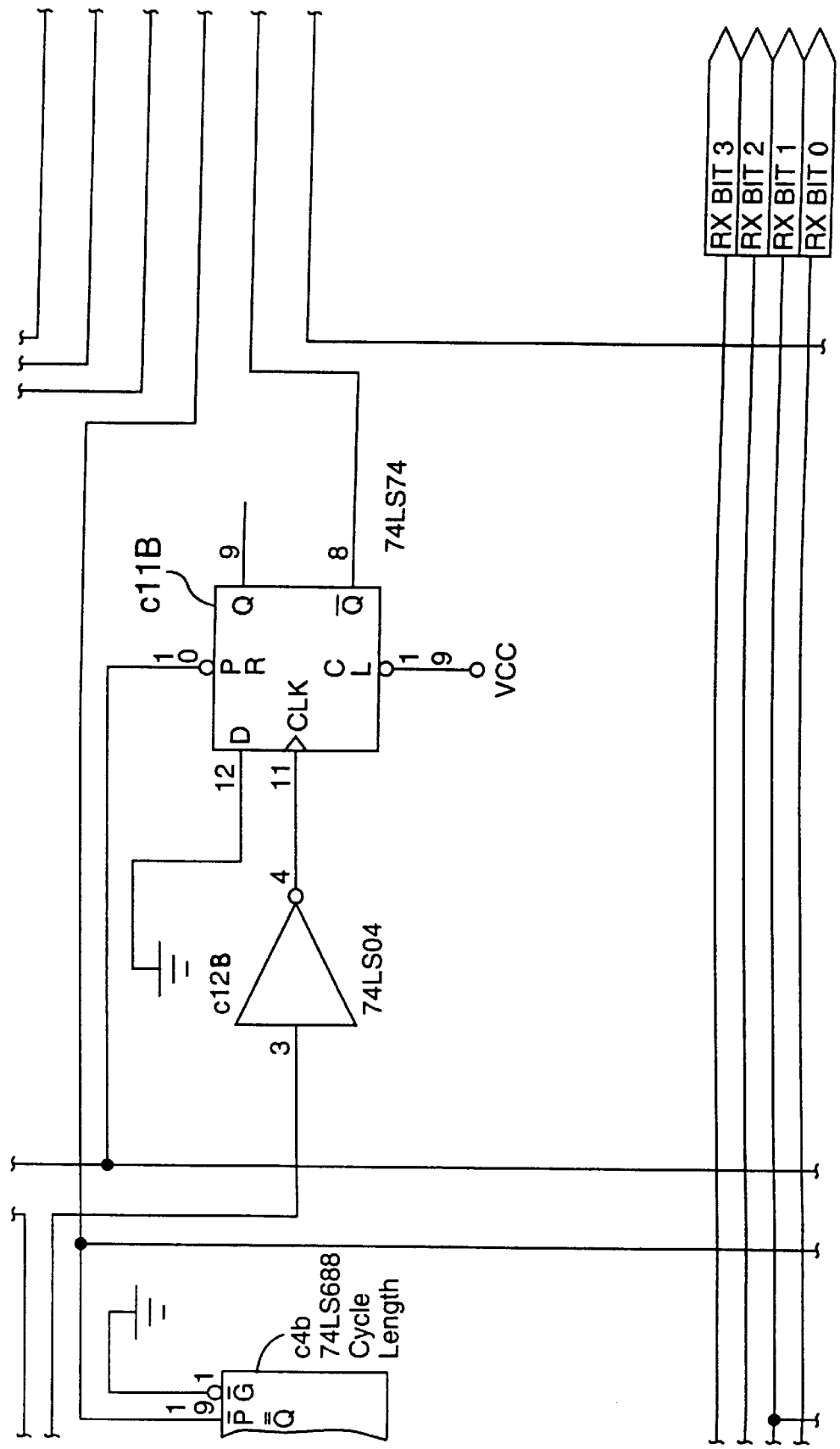
Figure 30:
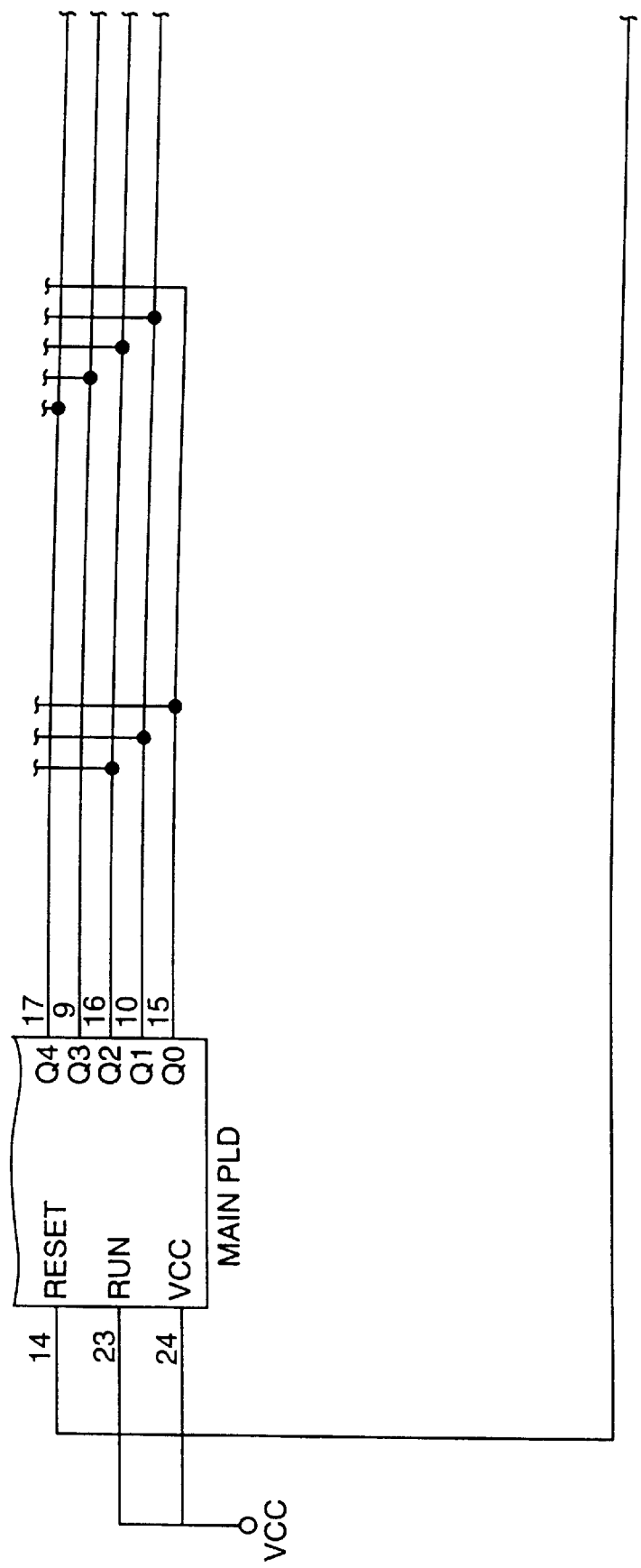
Figure 3P:
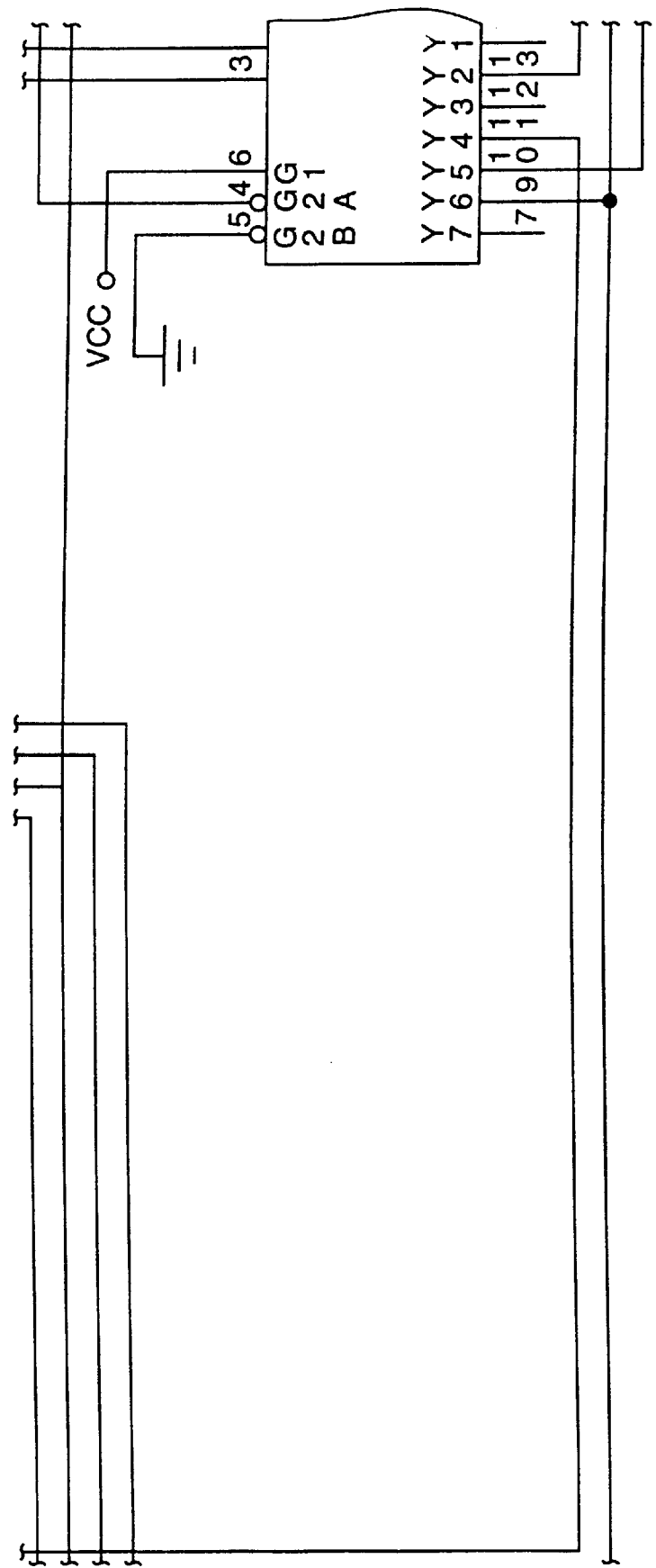
Figure 3Q:
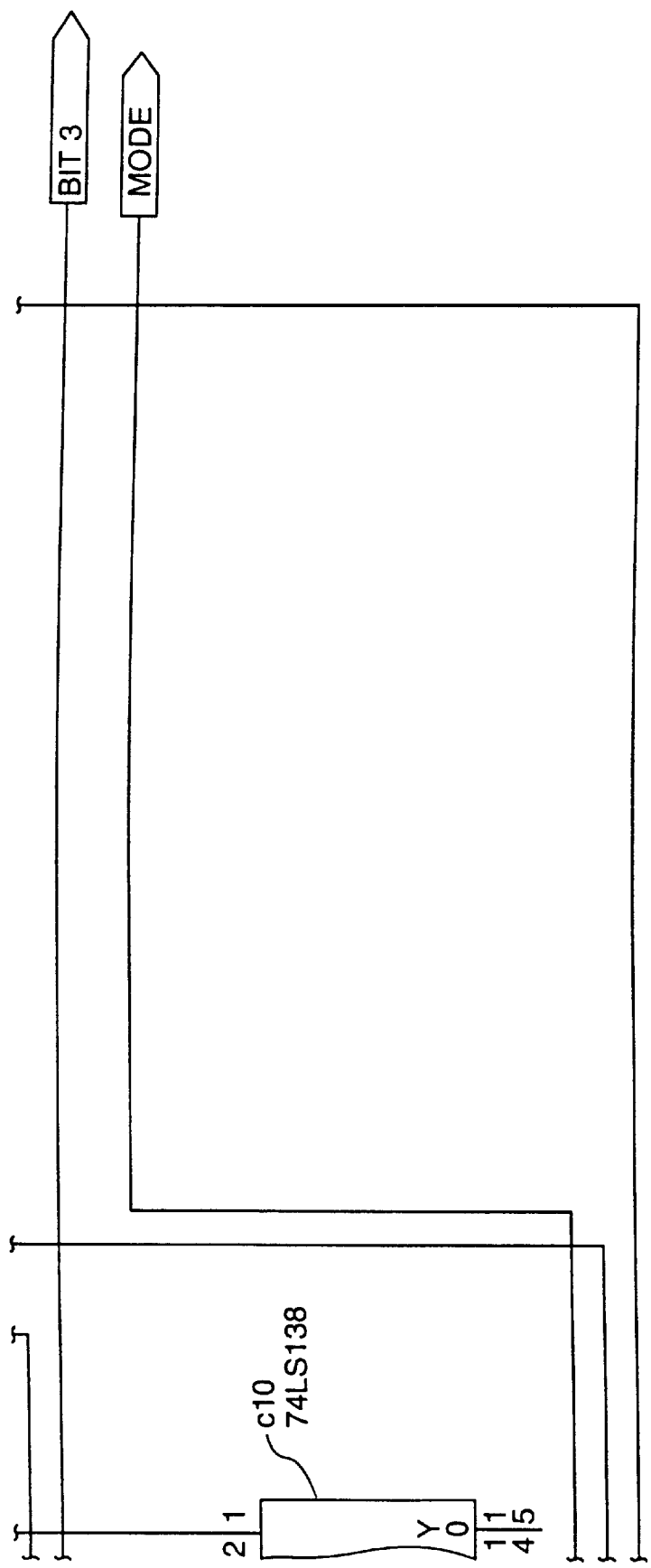
Figure 4A:
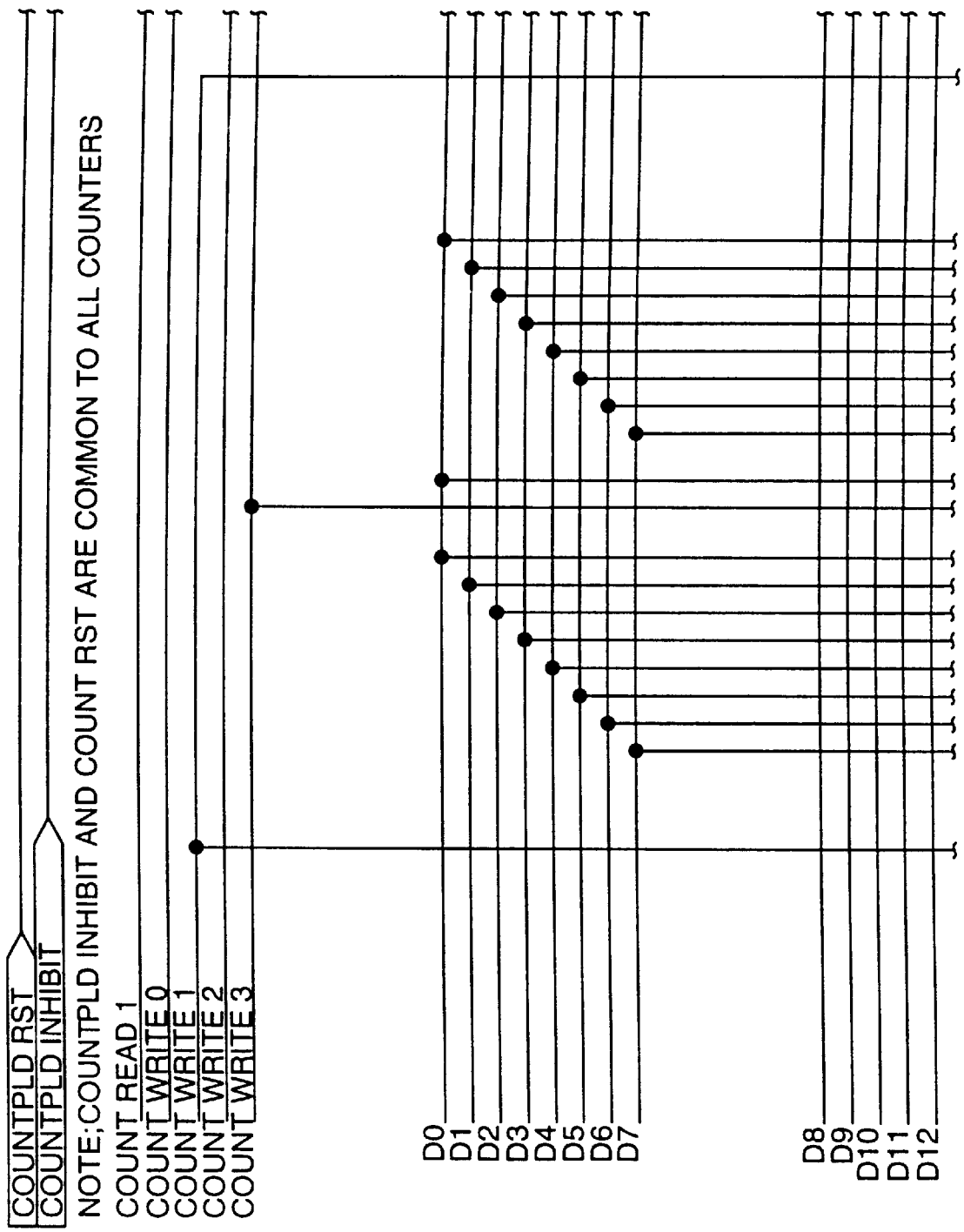
Figure 4B:
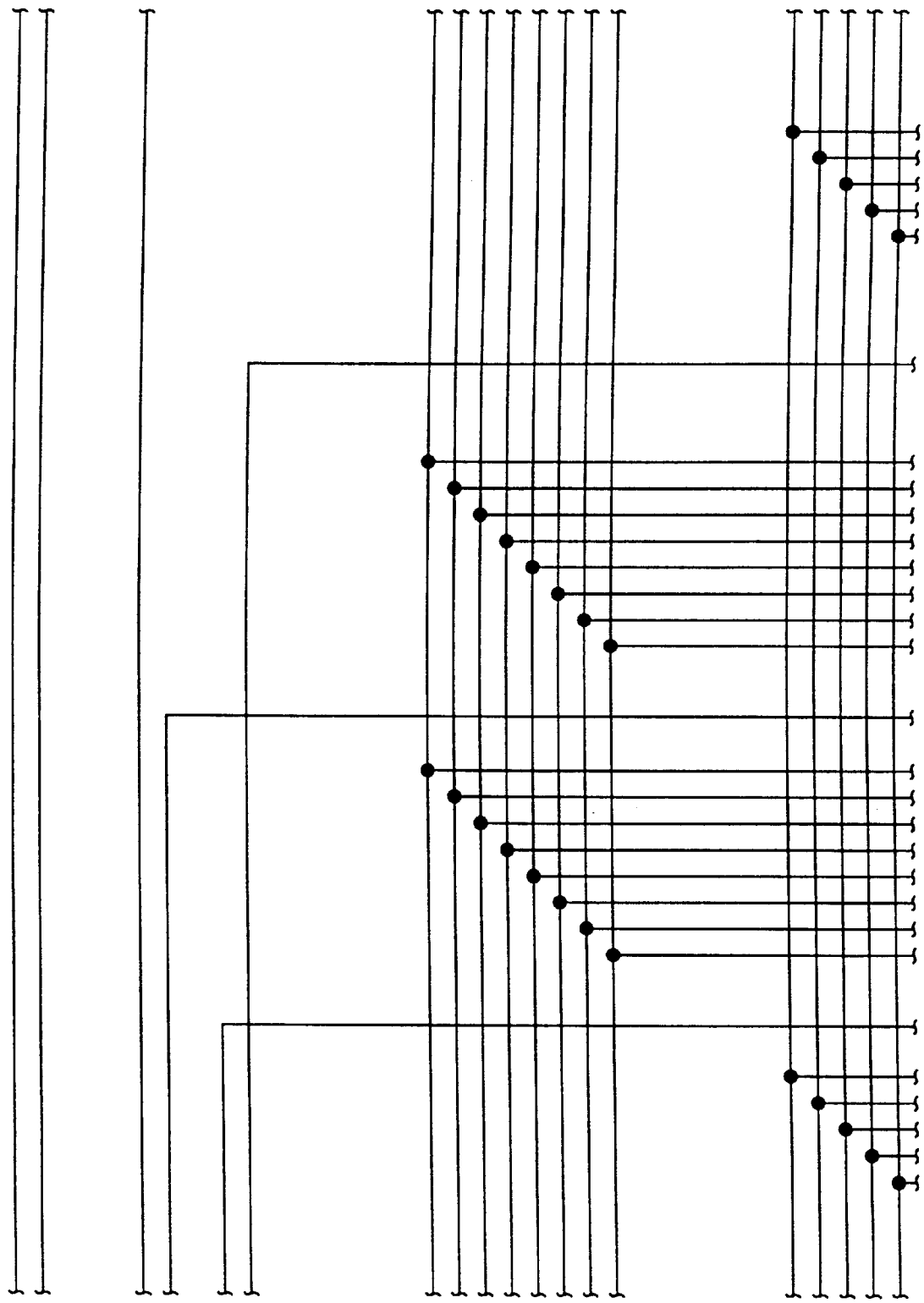
Figure 4C:
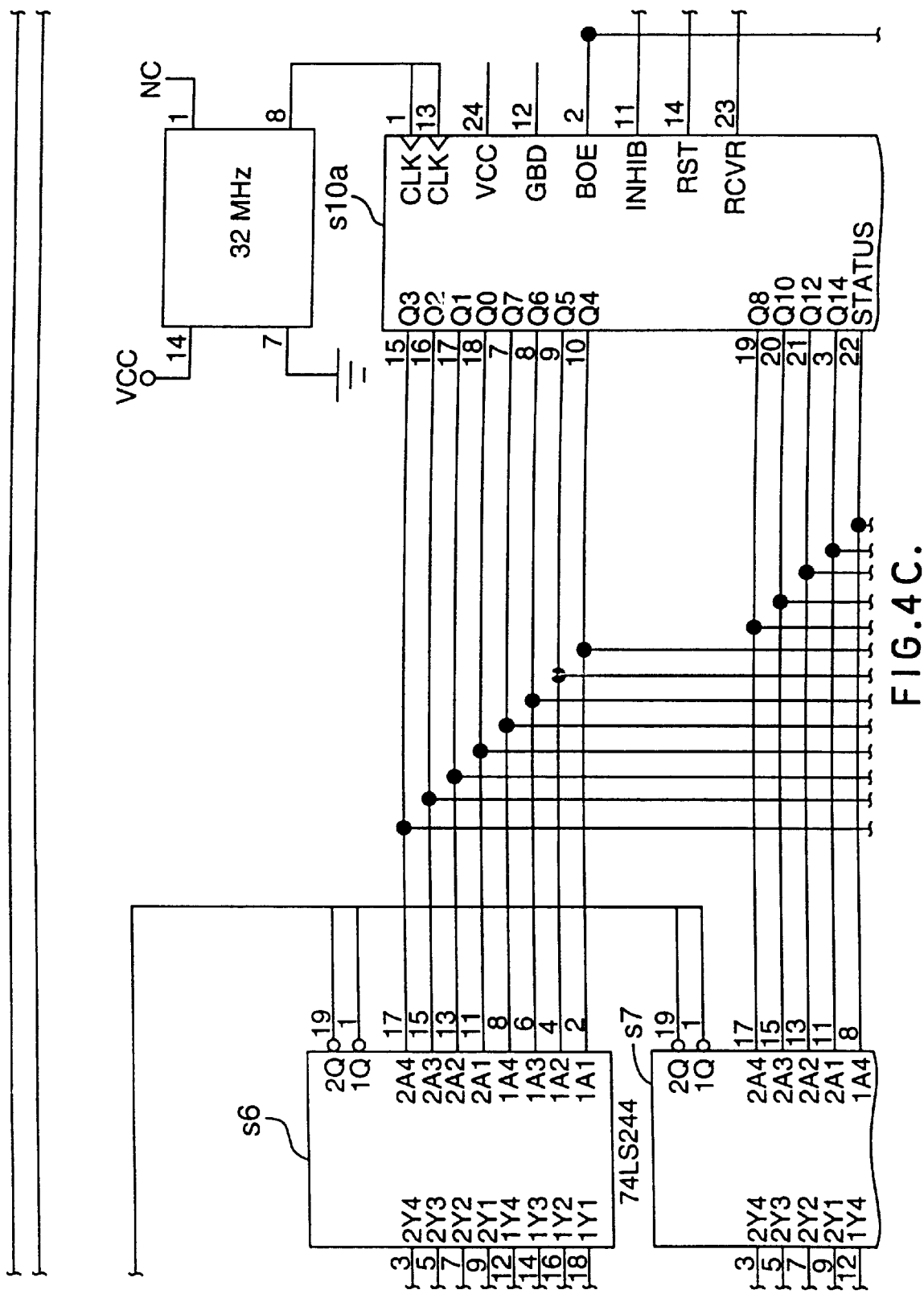
Figure 4E:
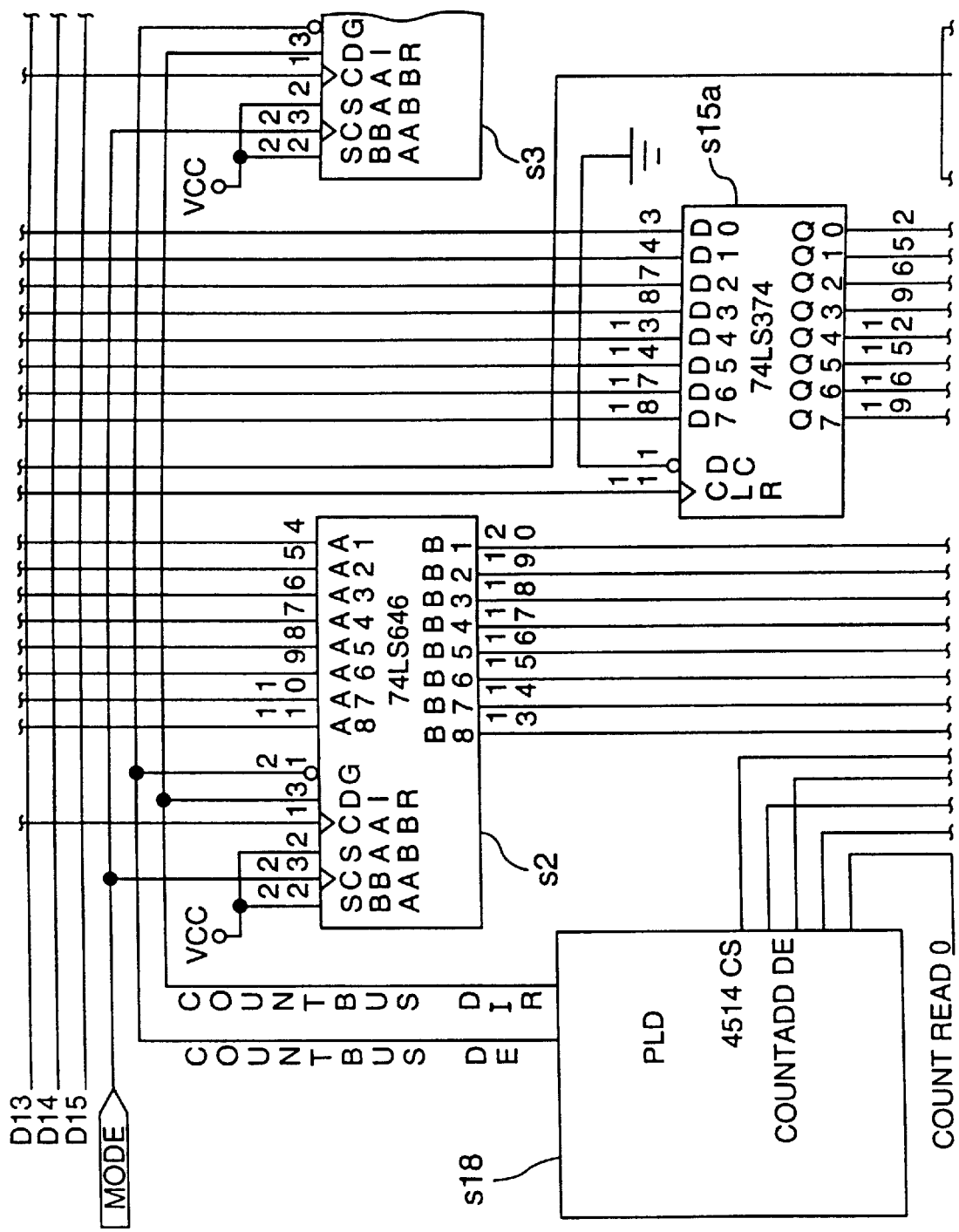
Figure 4F:
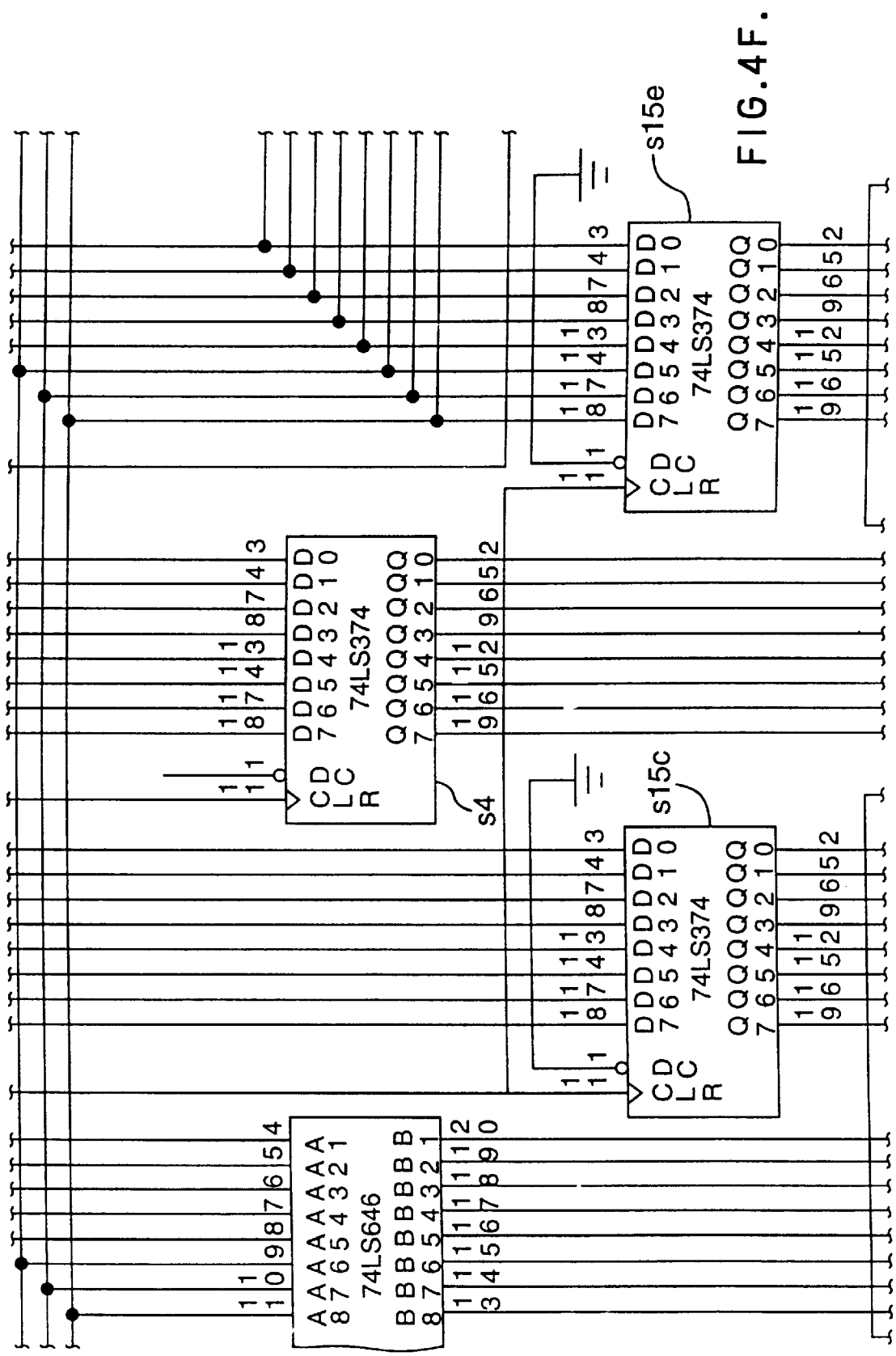
Figure 4G:
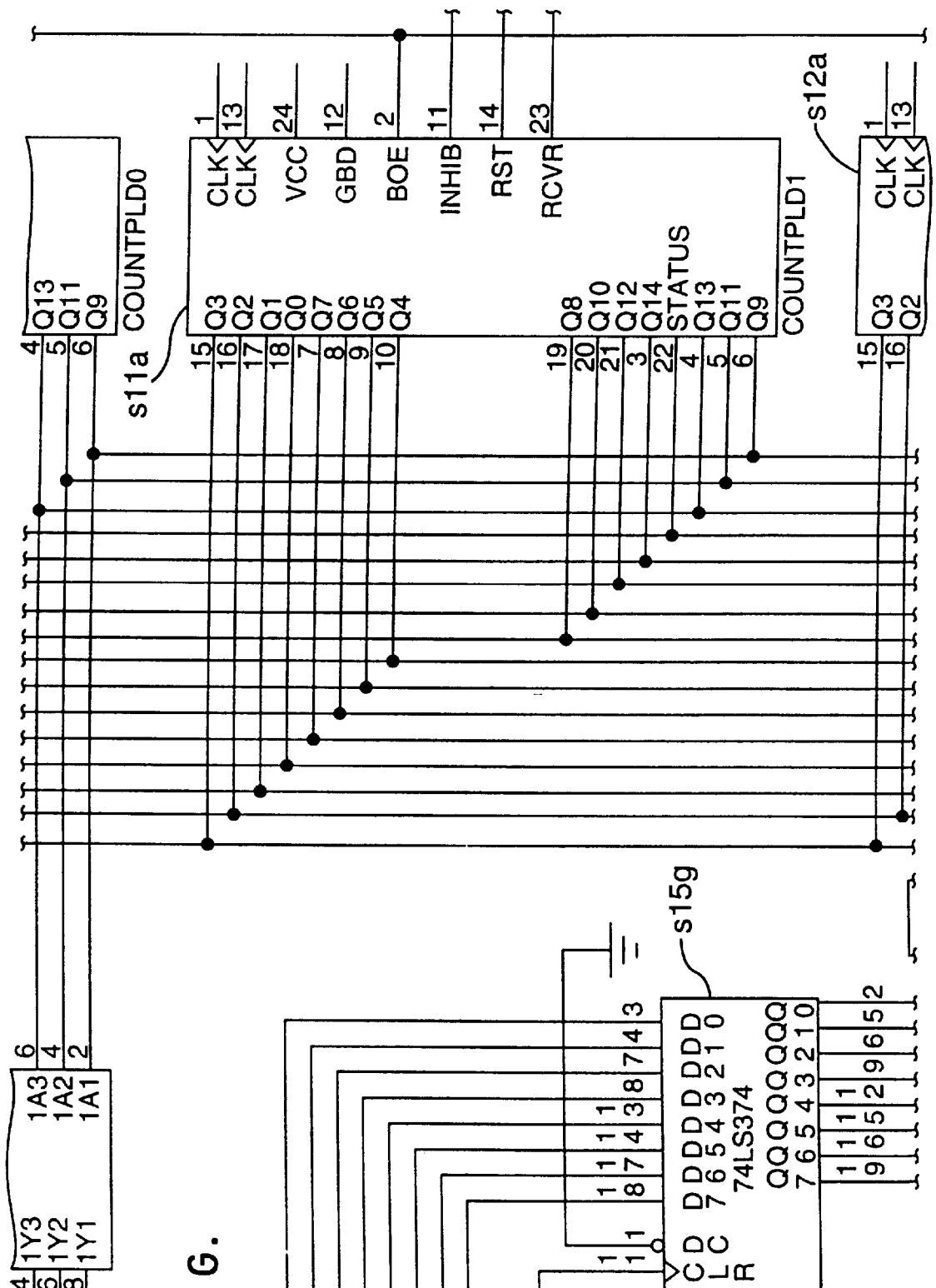
Figure 4H:
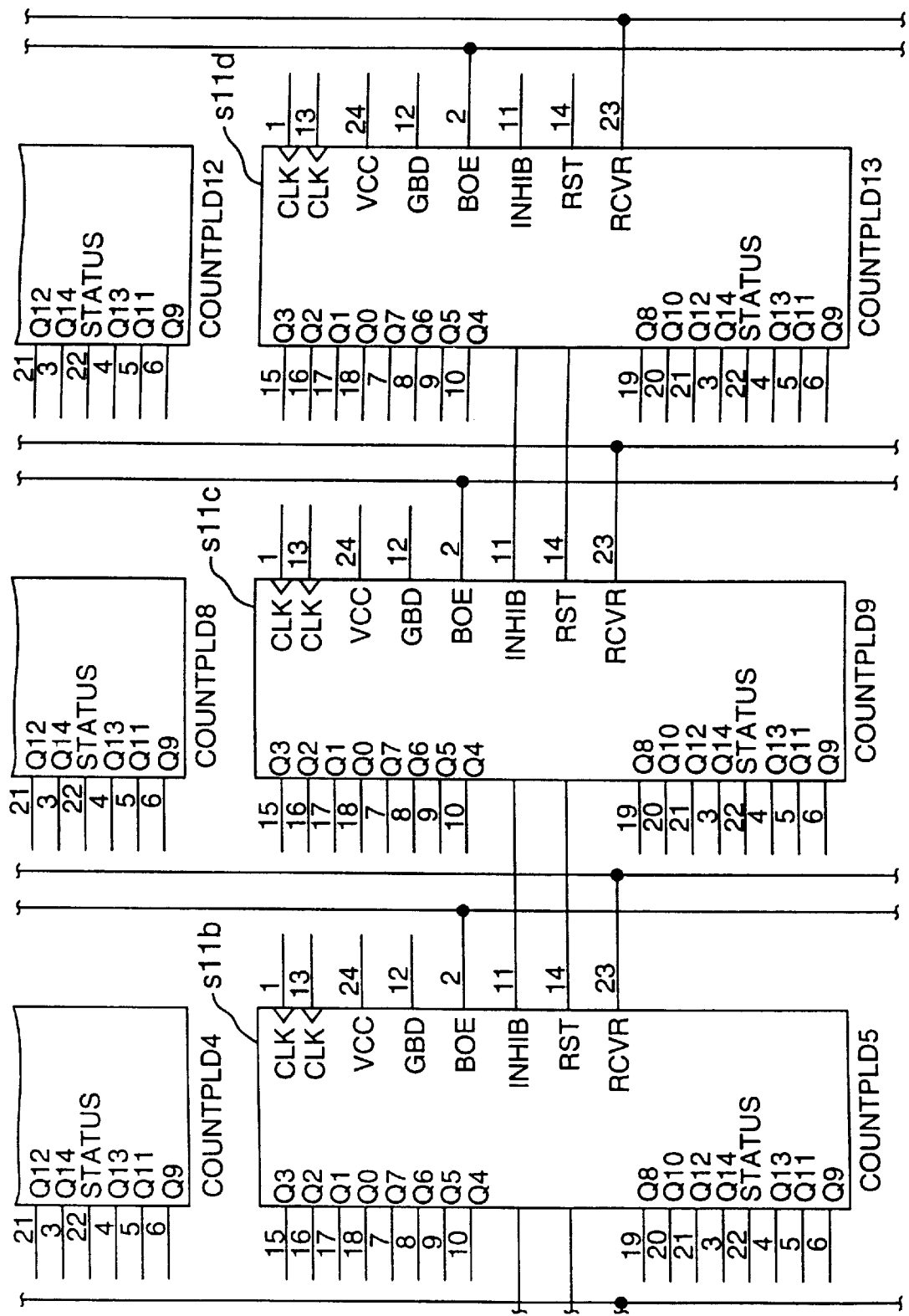
Figure 4I:
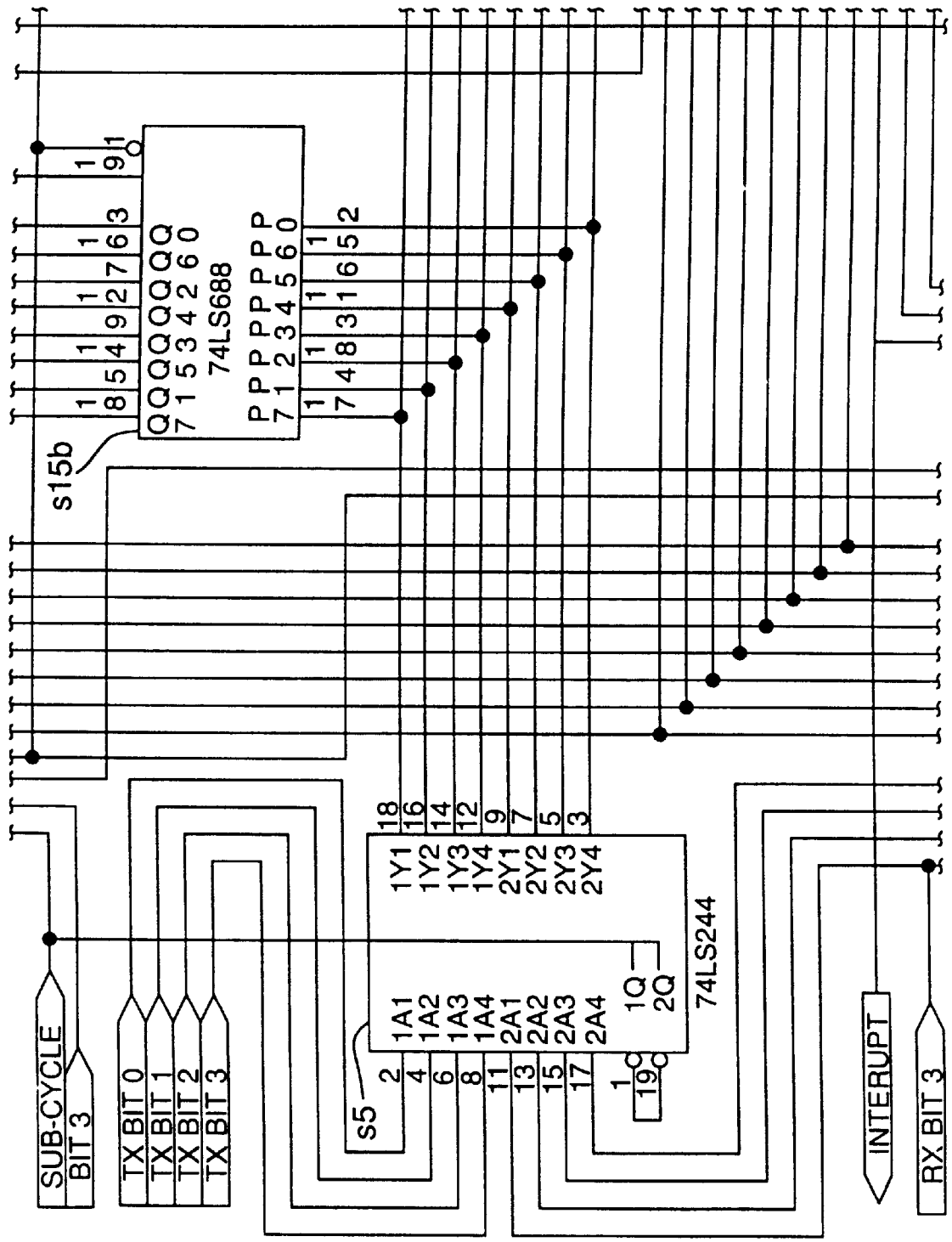
Figure 4J:
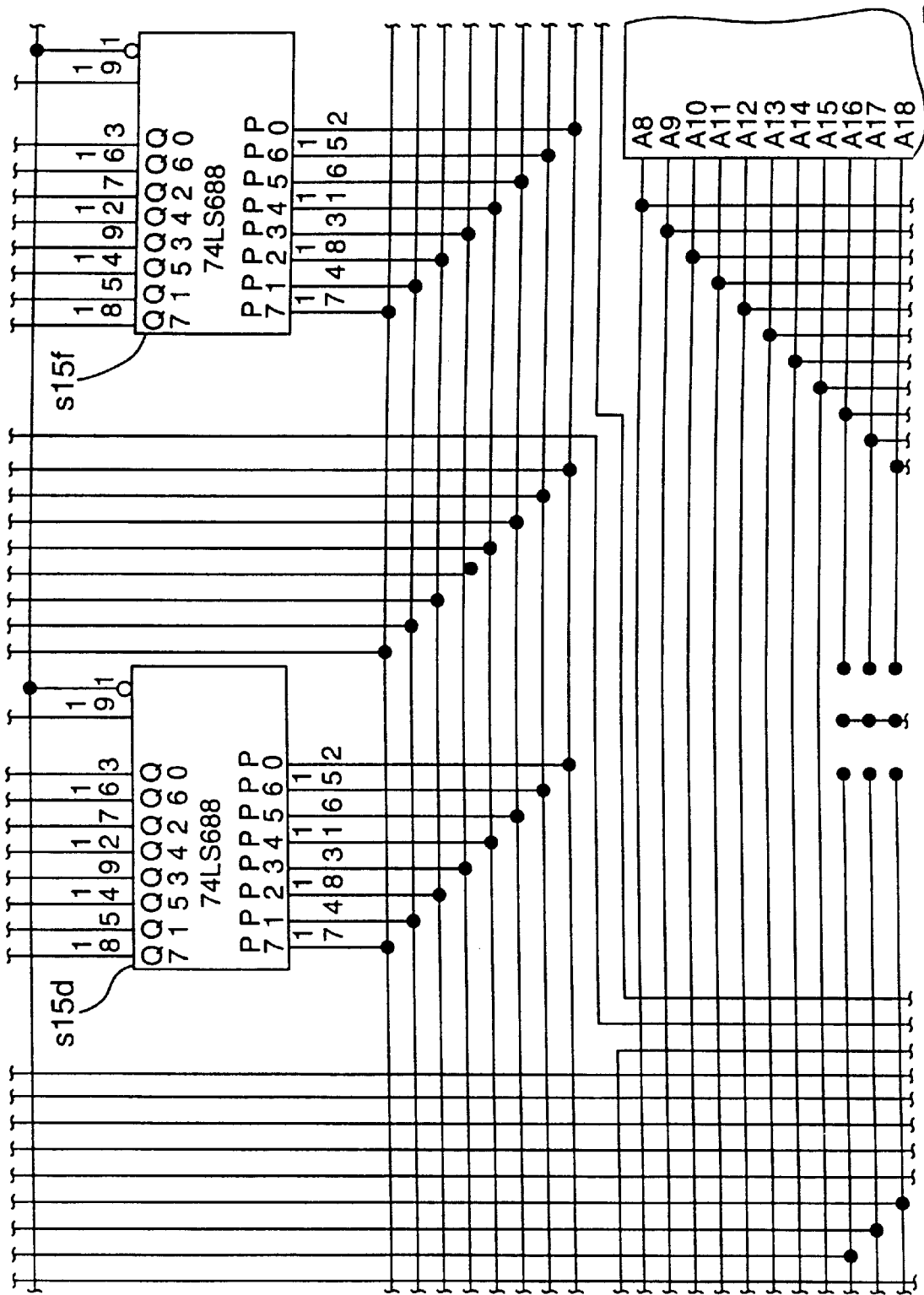
Figure 4K:
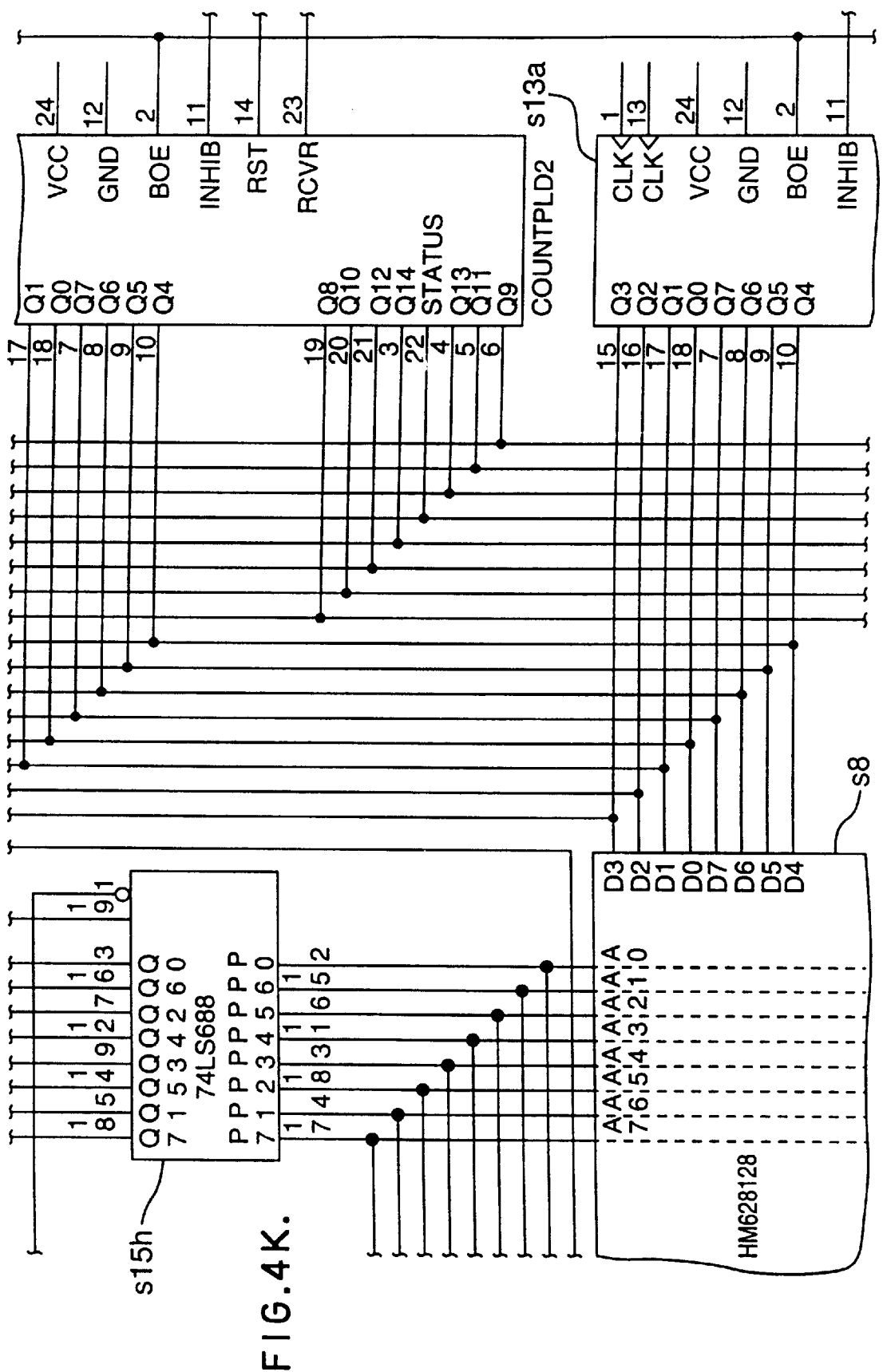
Figure 4L:
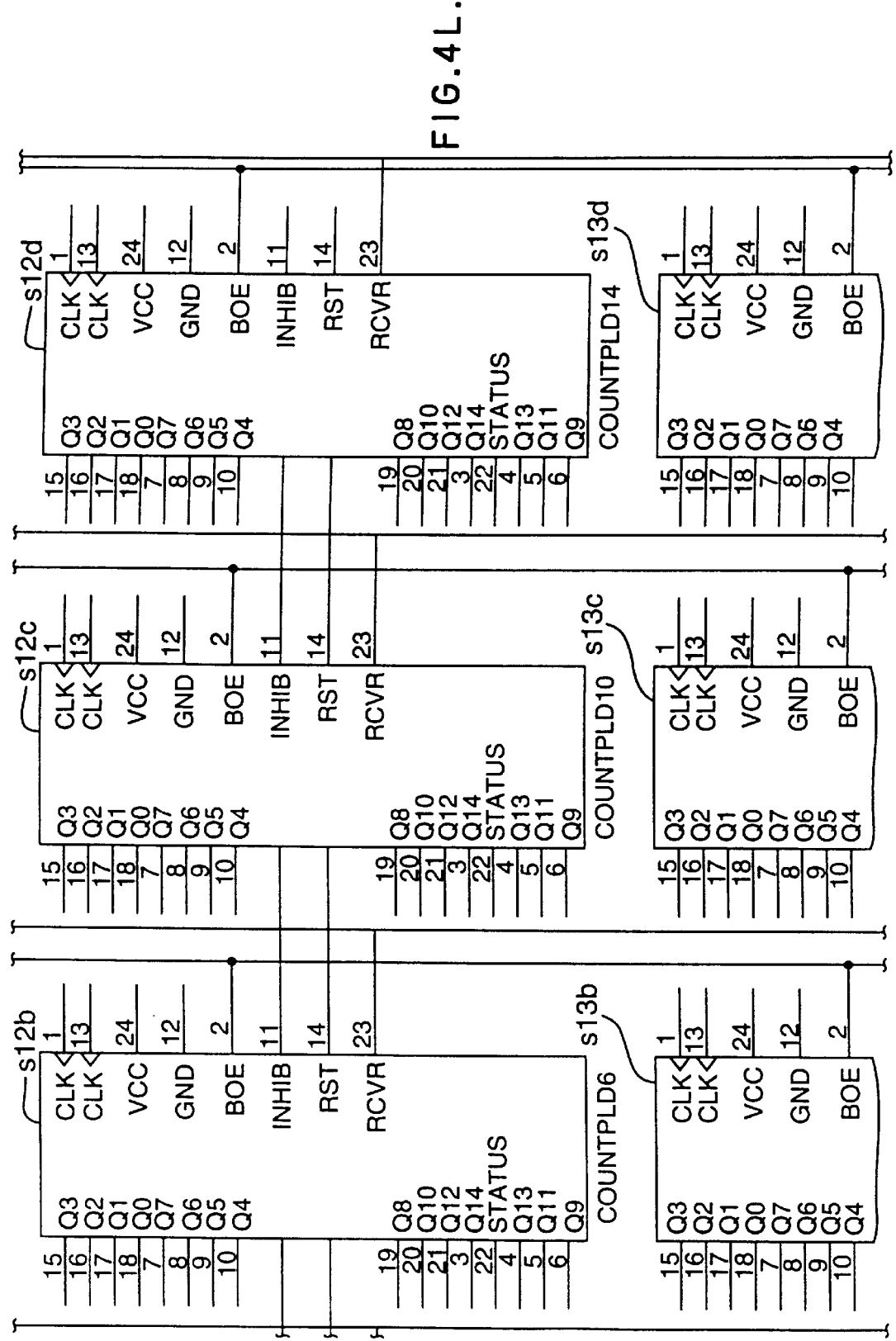
Figure 4M:
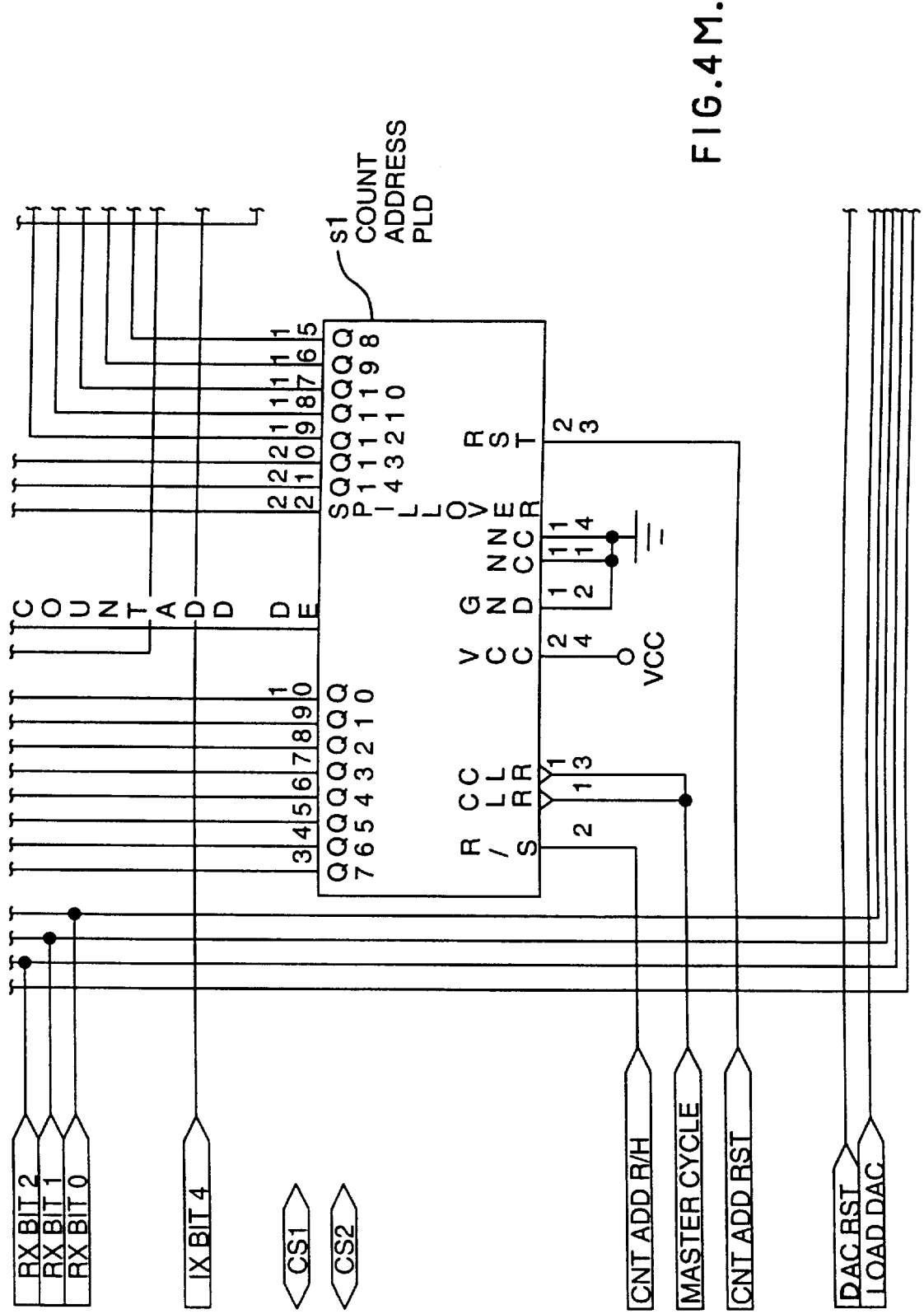
Figure 4N:
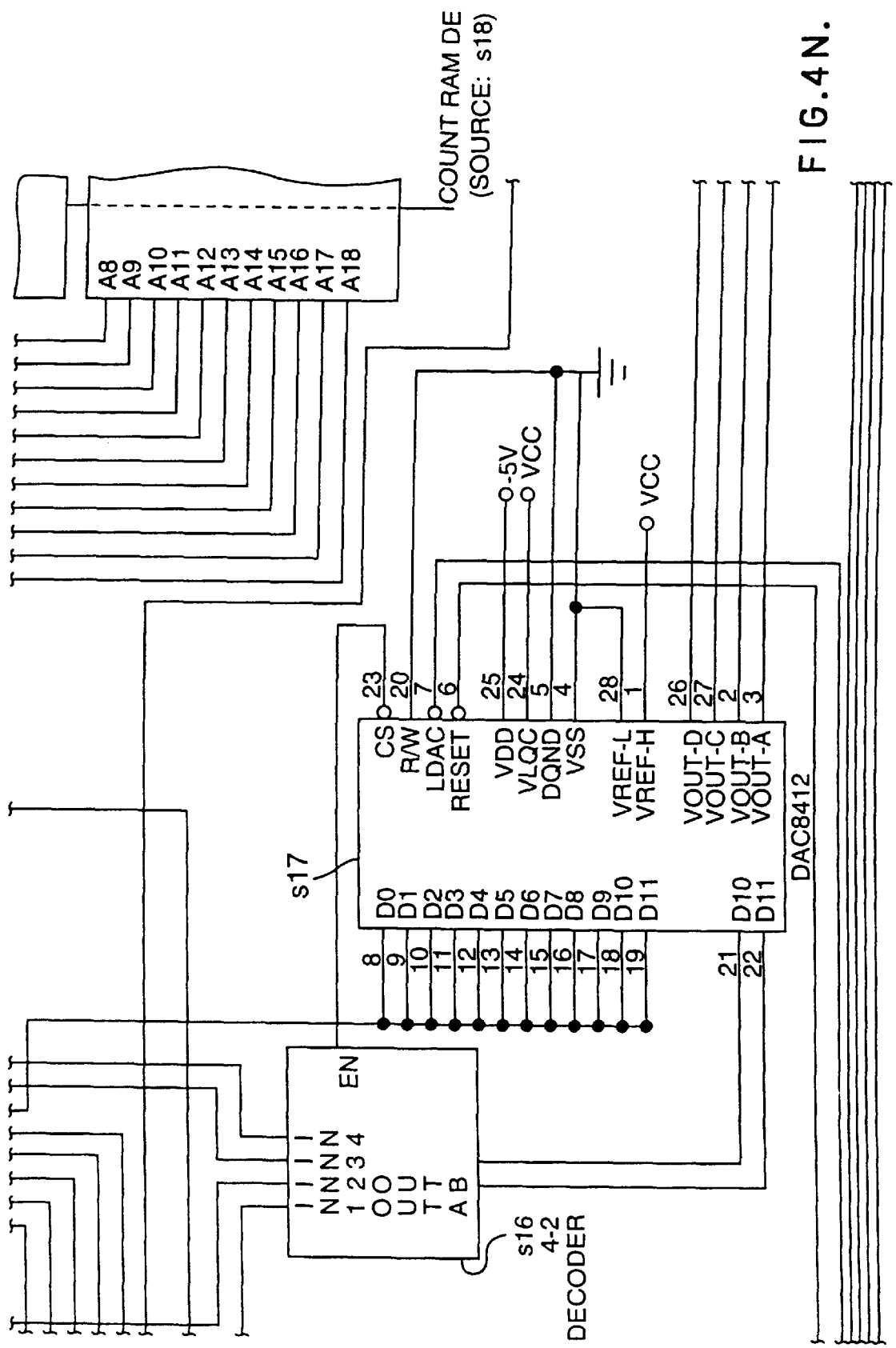
Figure 40:
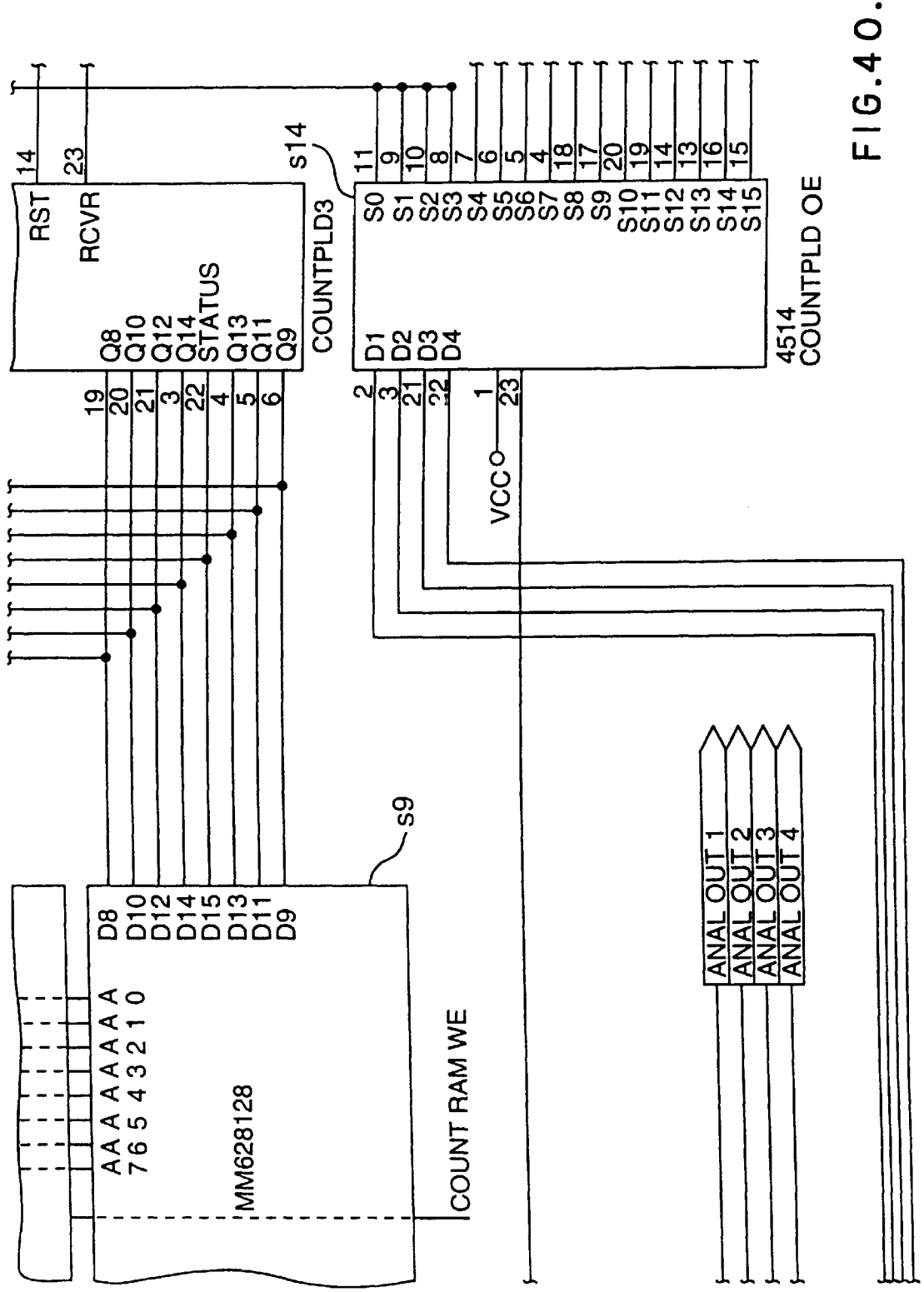
Figure 4P:
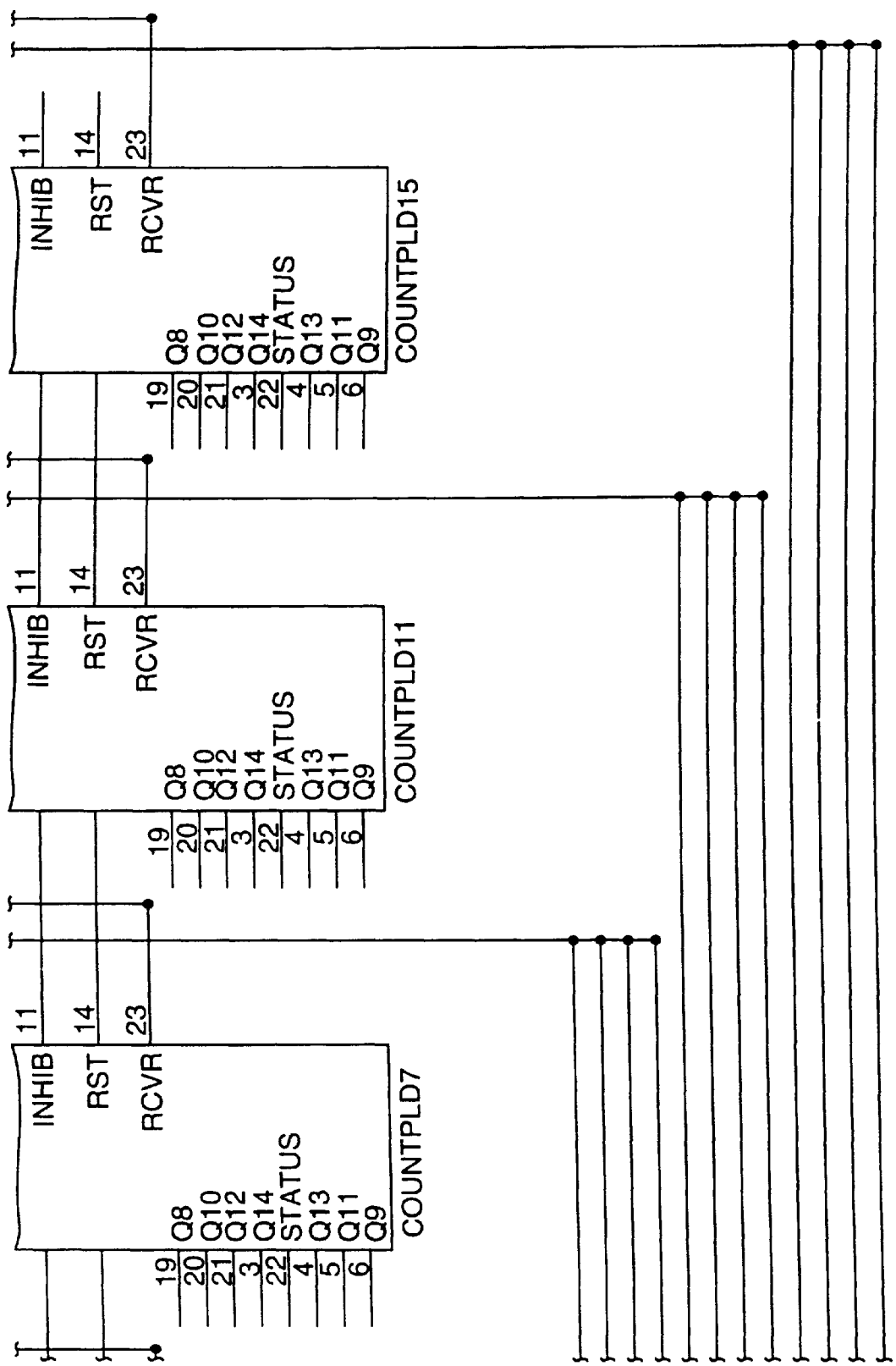
Figure 5A:
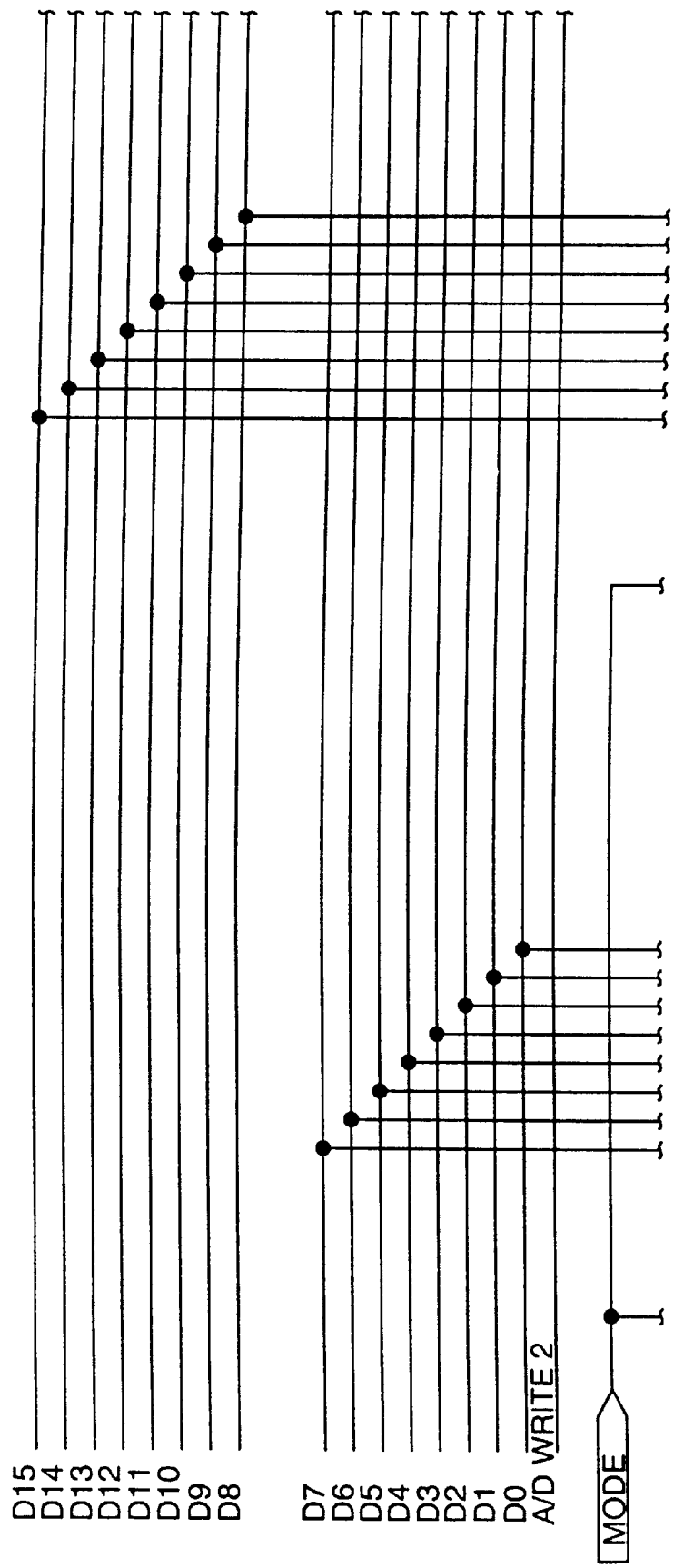
Figure 5B:
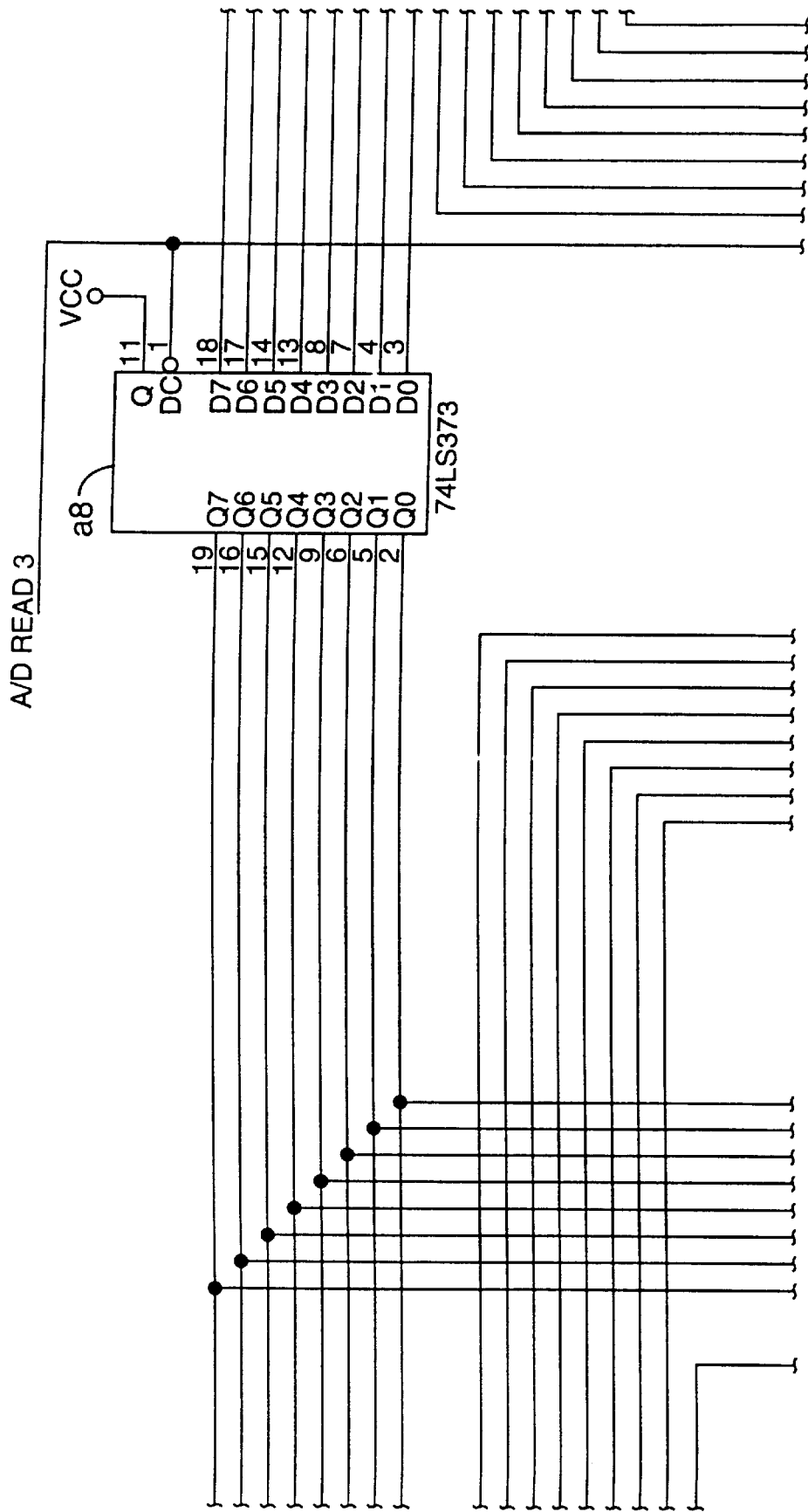
Figure 5C:
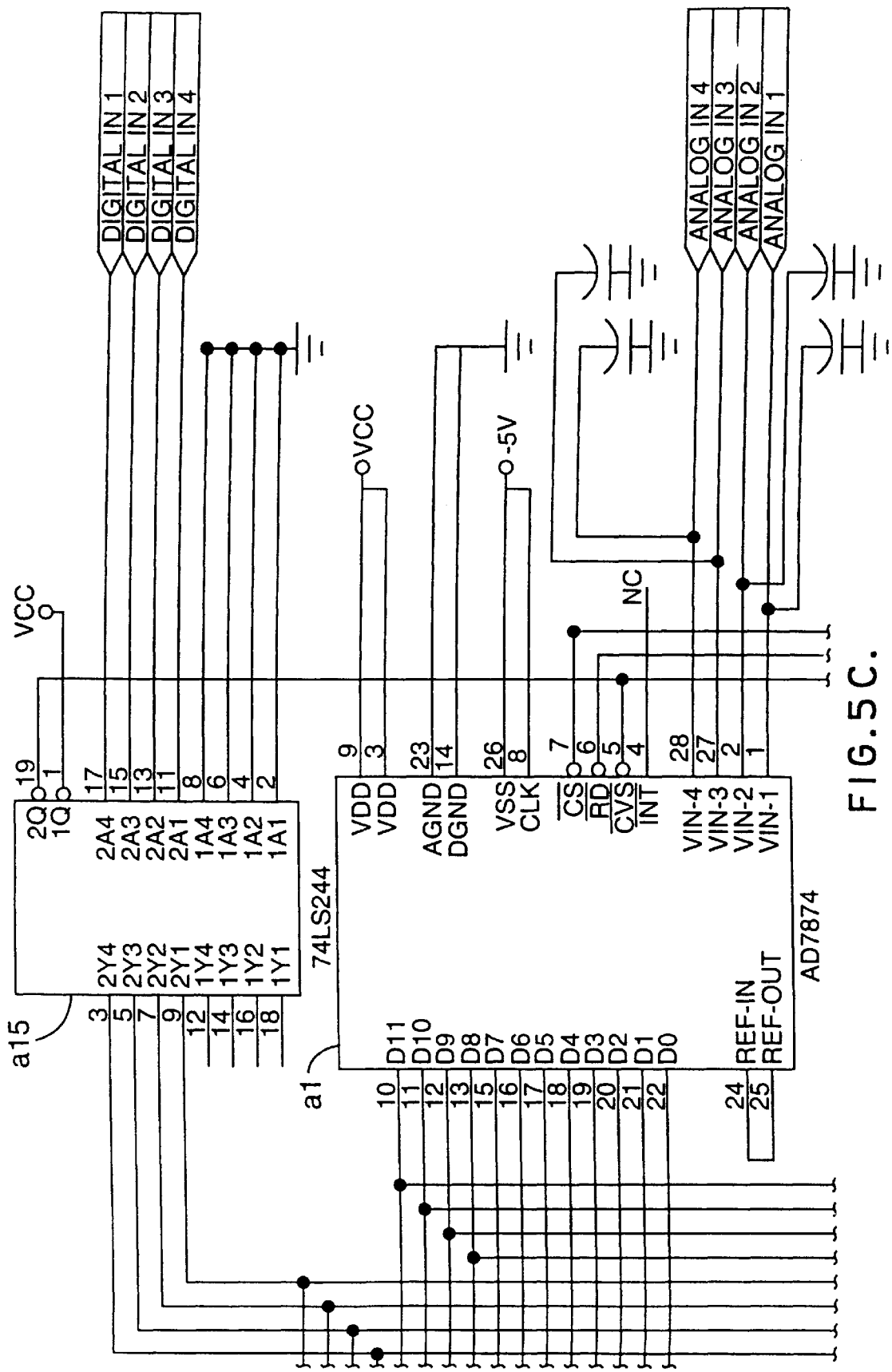
Figure 5F:
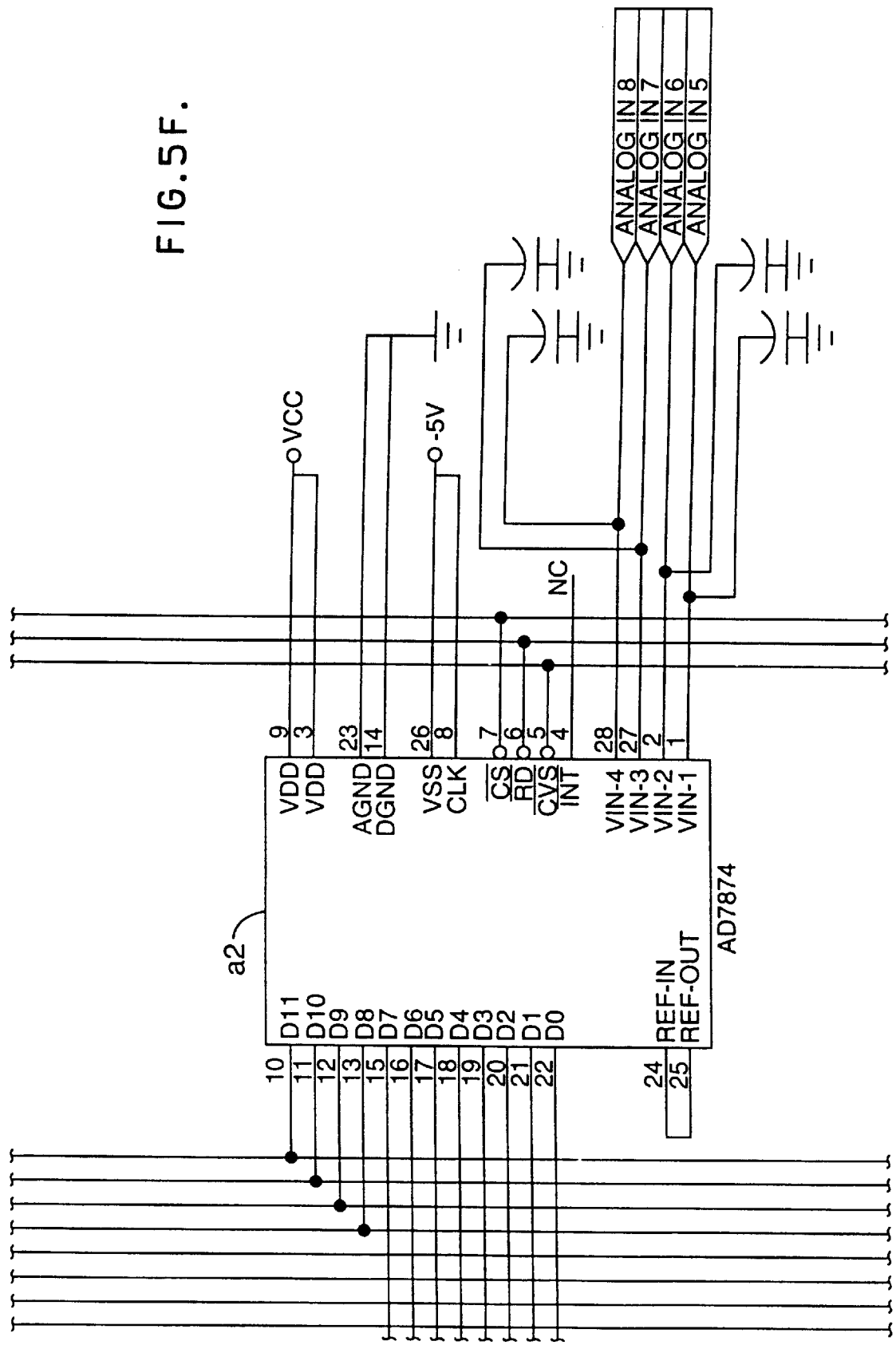
Figure 5G:
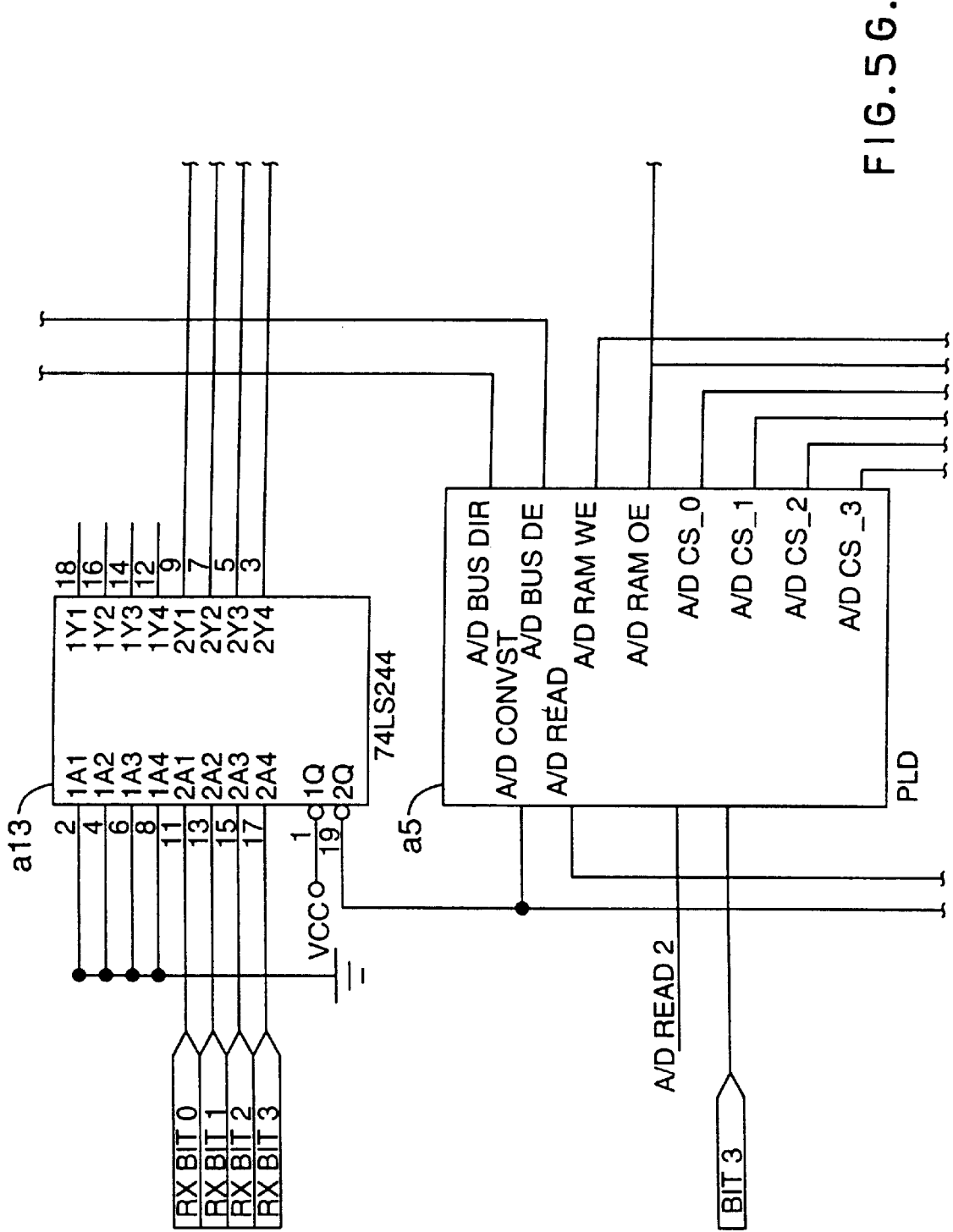
Figure 5H:
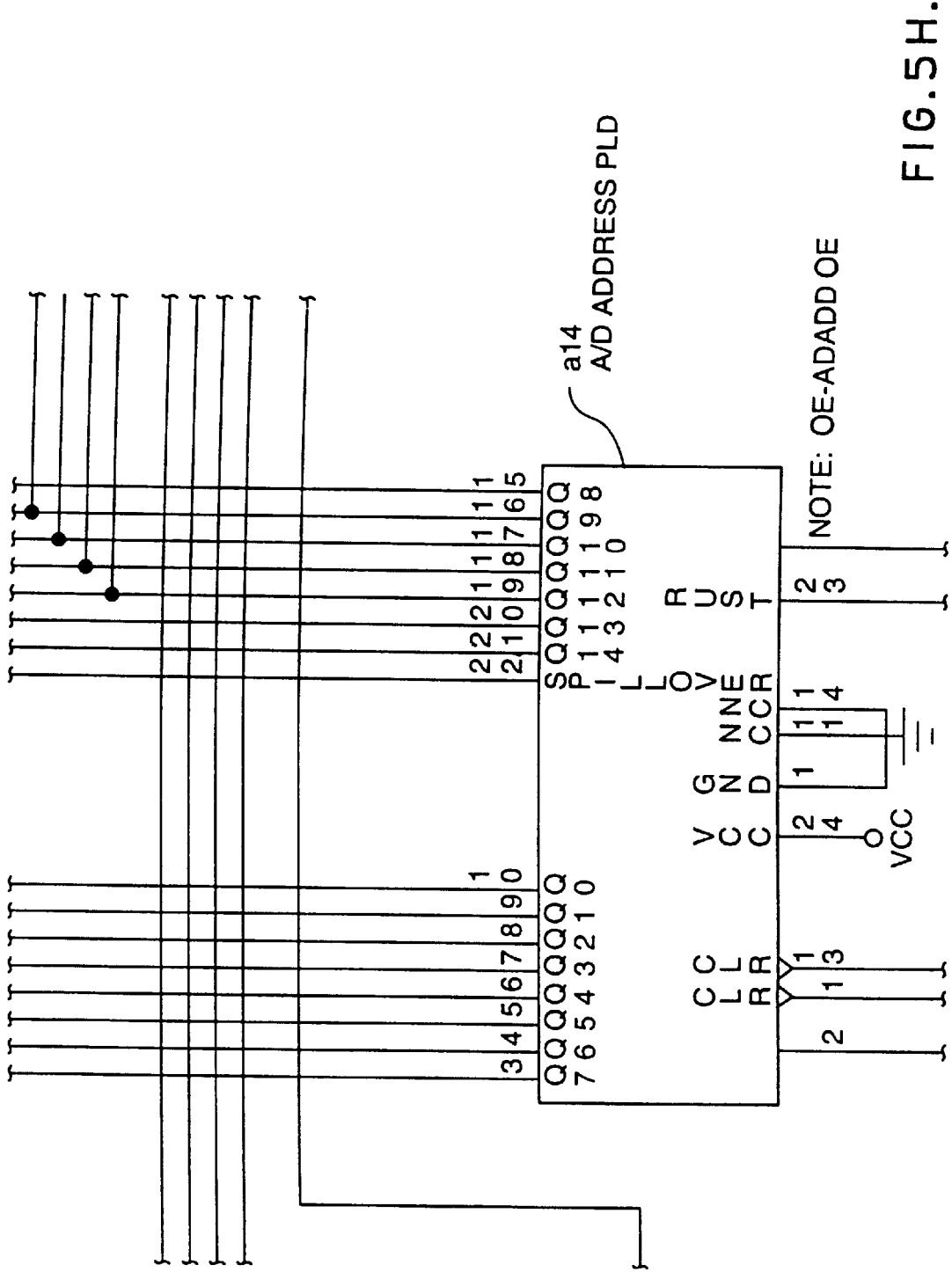
Figure 5I:
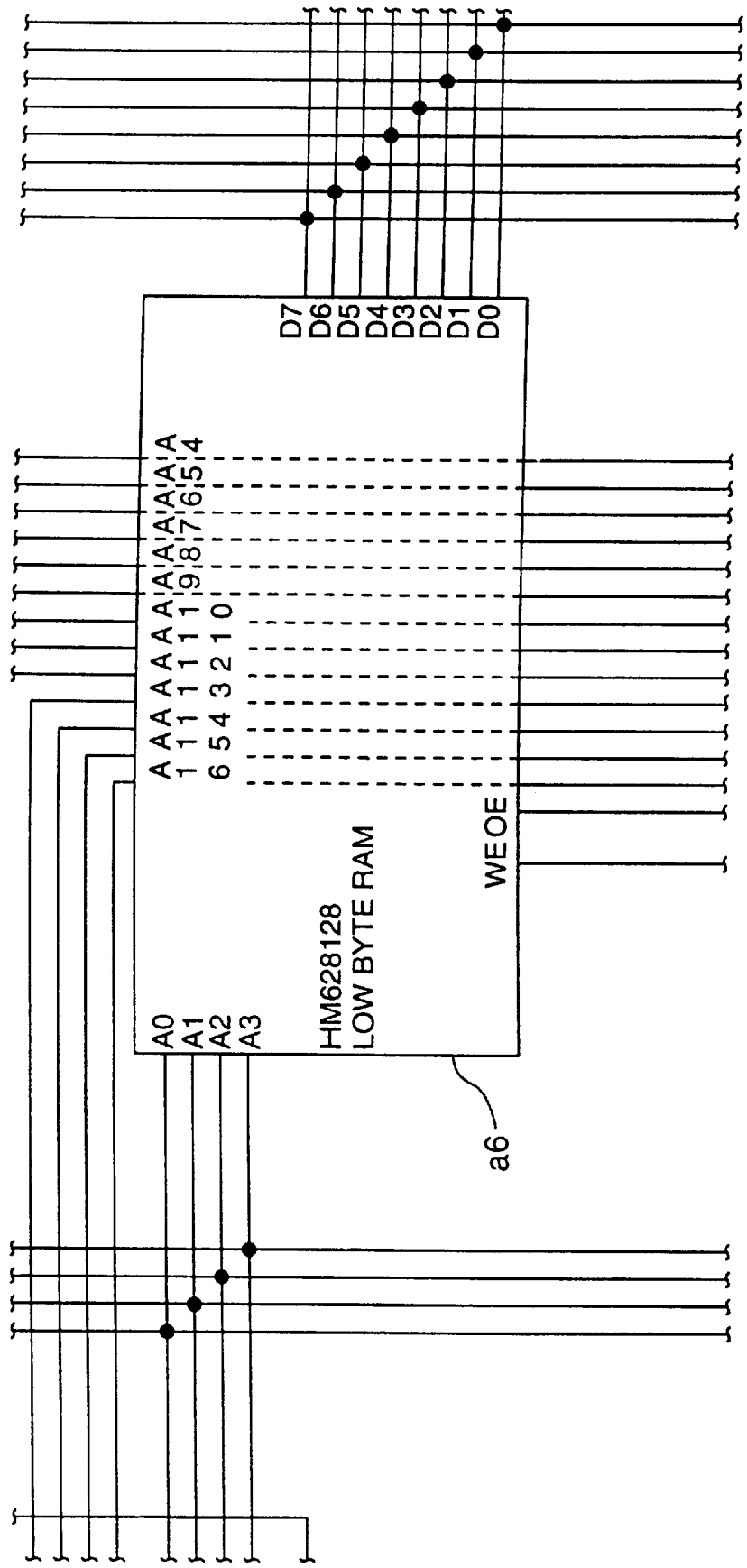
Figure 5J:
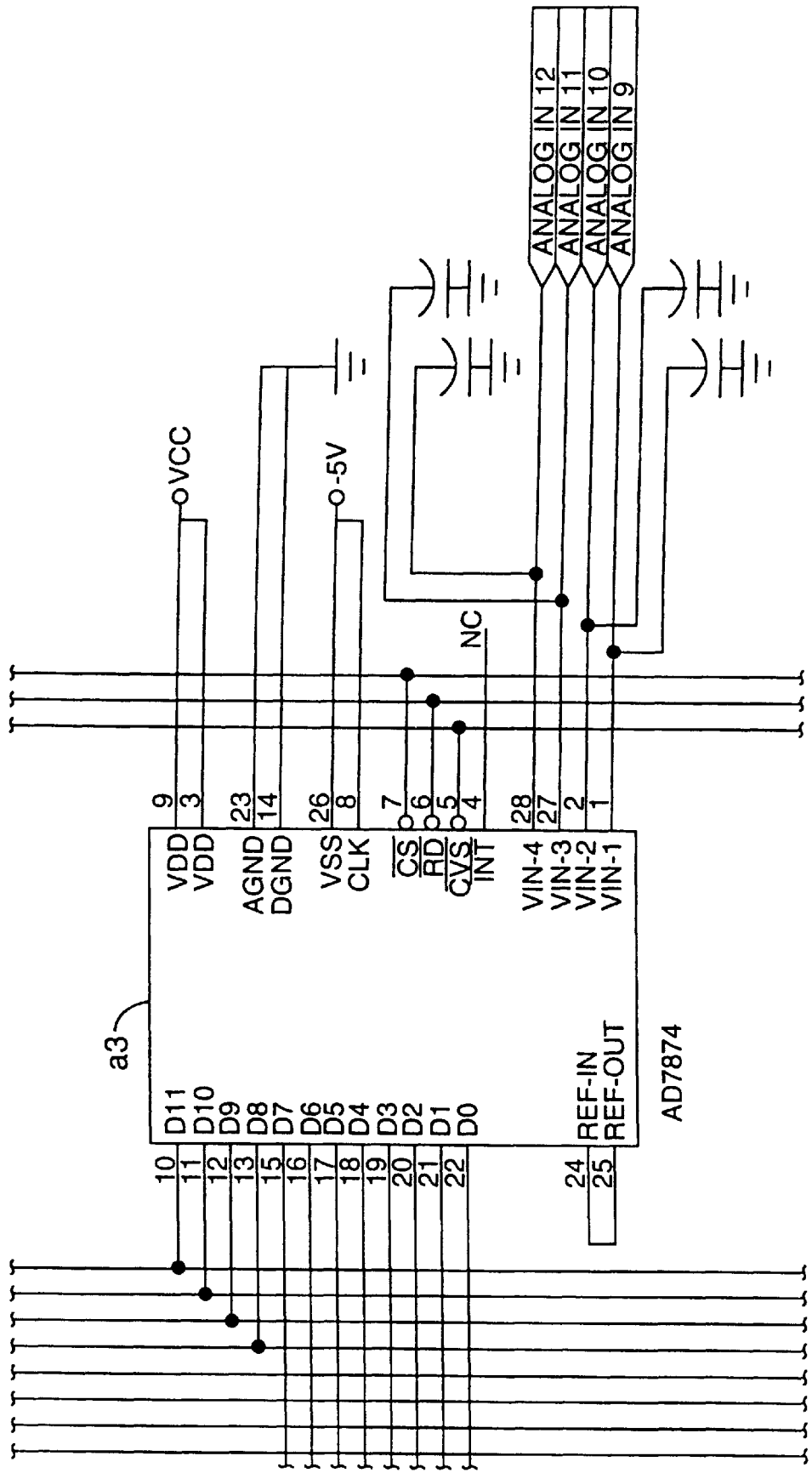
Figure 5K:
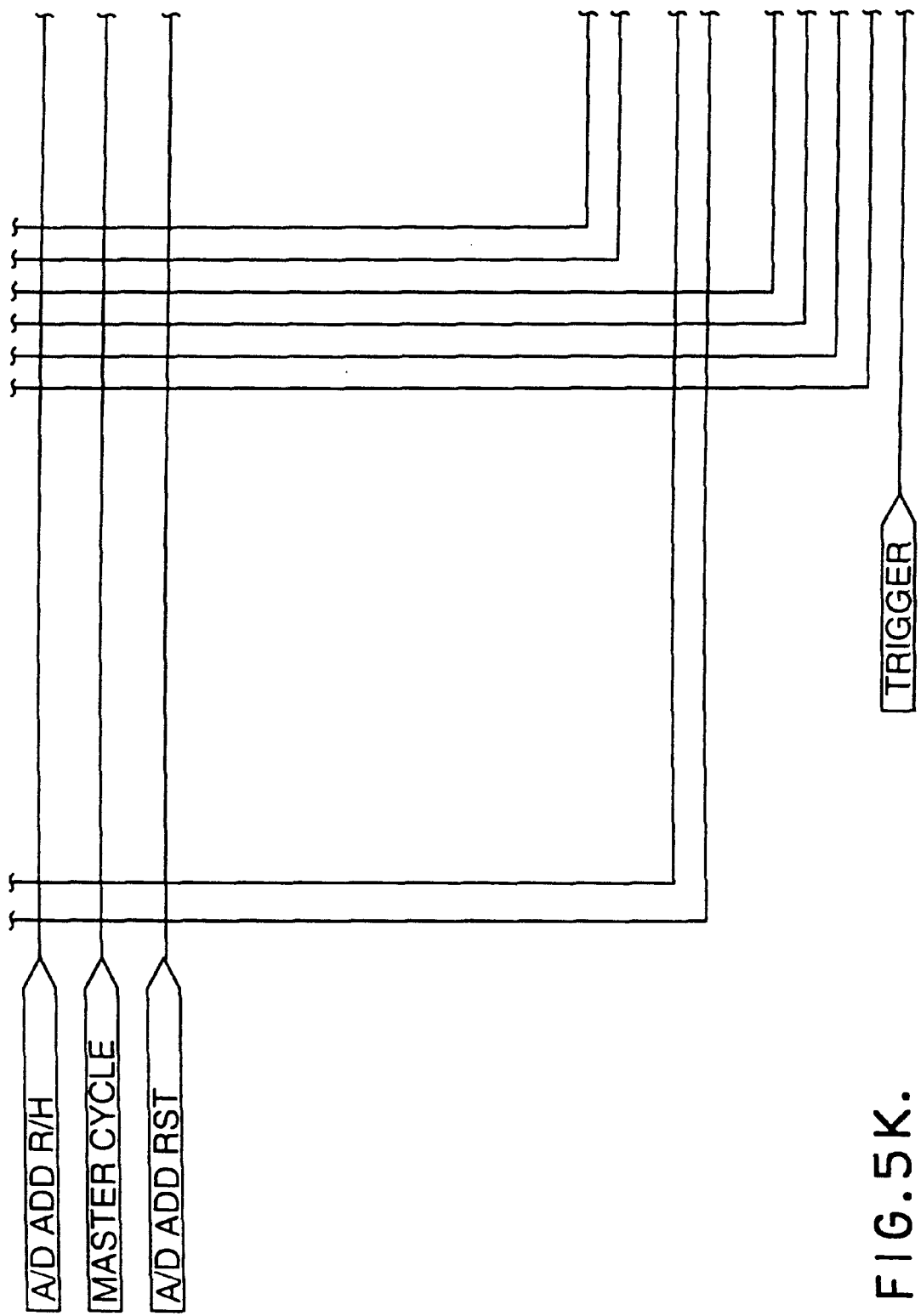
Figure 5L:
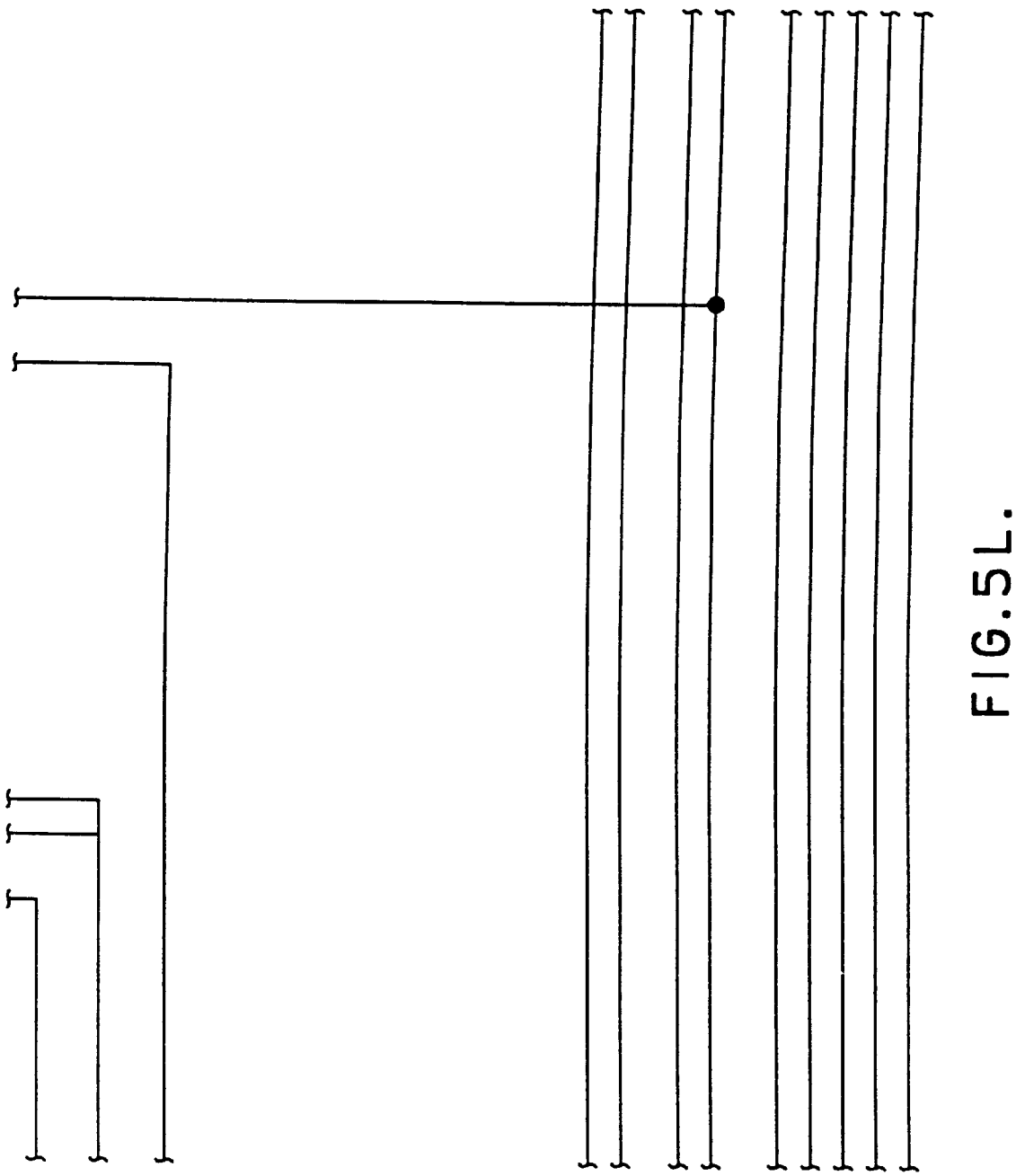
Figure 5M:
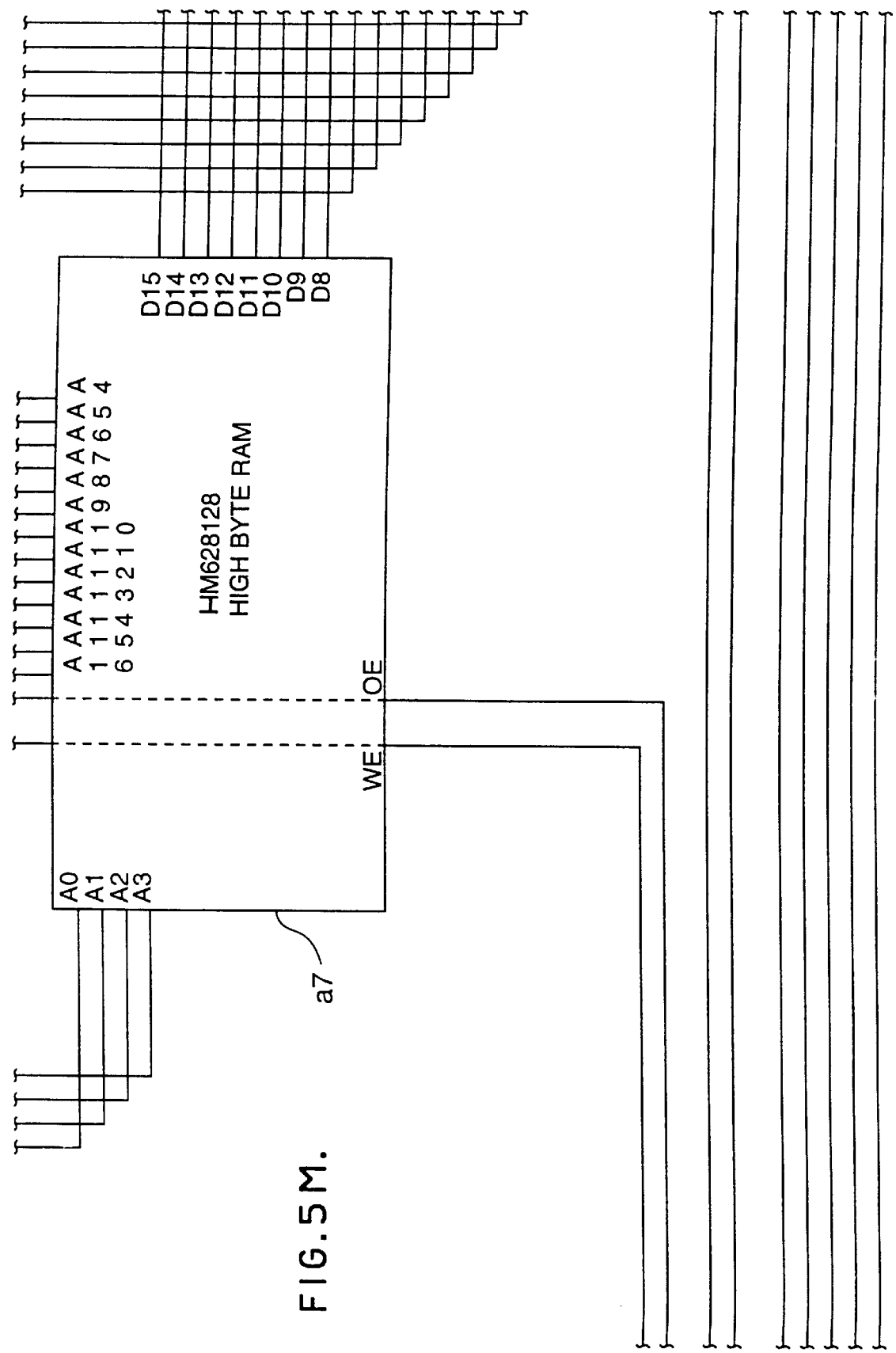
Figure 5N:
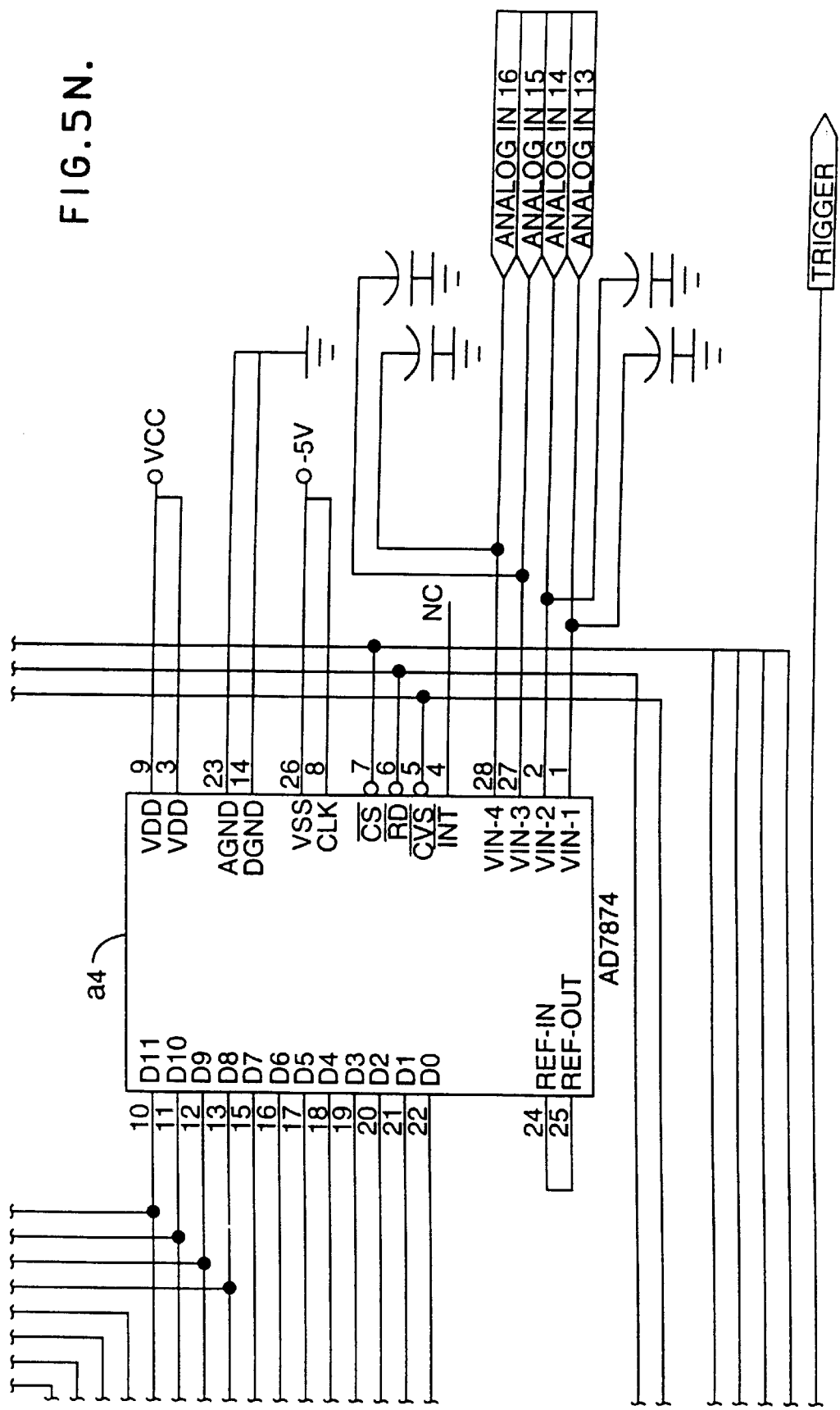
Figure 6A:
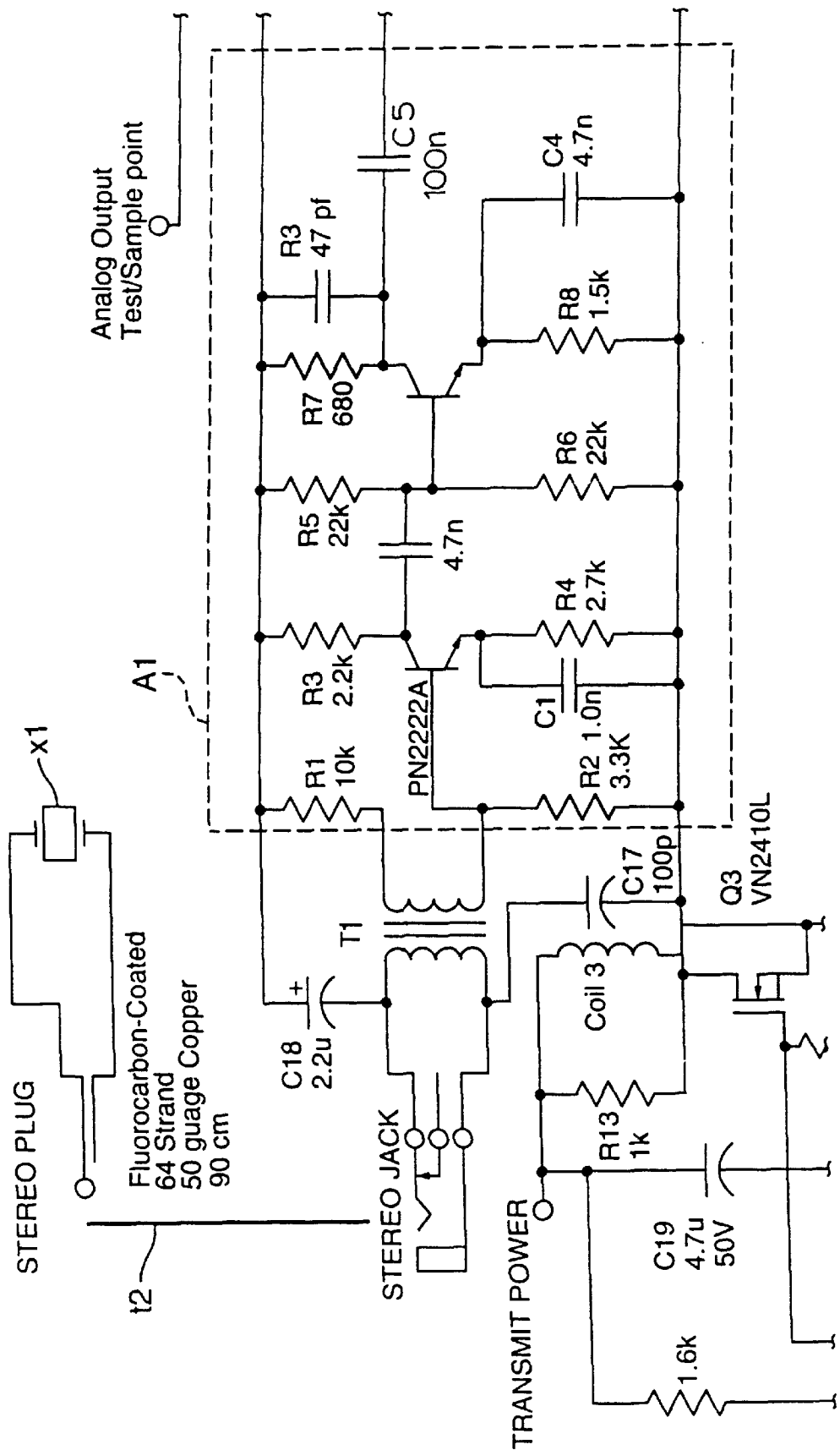
FIGS. 6A, 6B, 6C and 6D, is a schematic diagram of a transmitter/receiver/transceiver architecture according to the preferred embodiment.
Figure 6B:
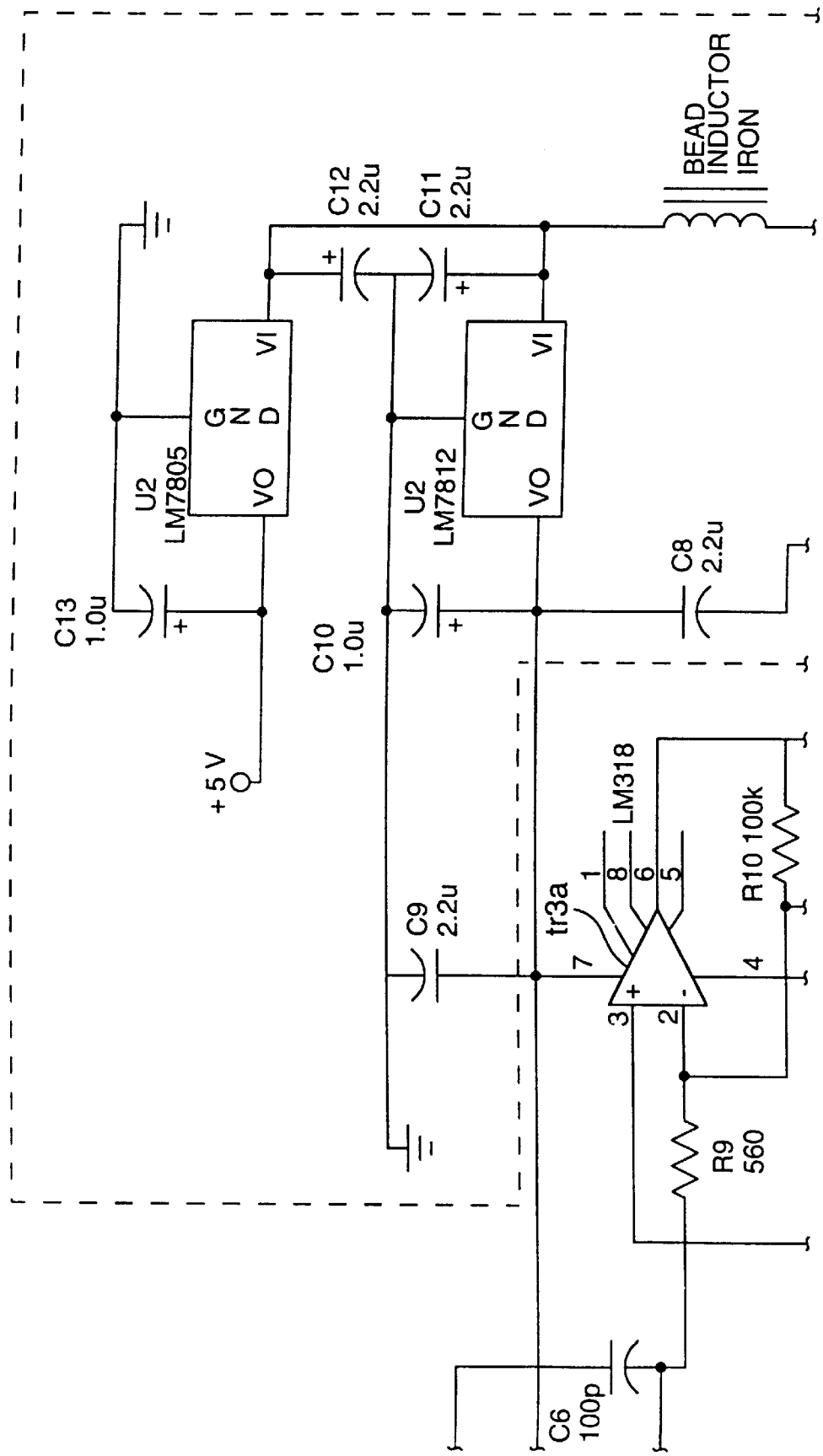
Figure 6C:
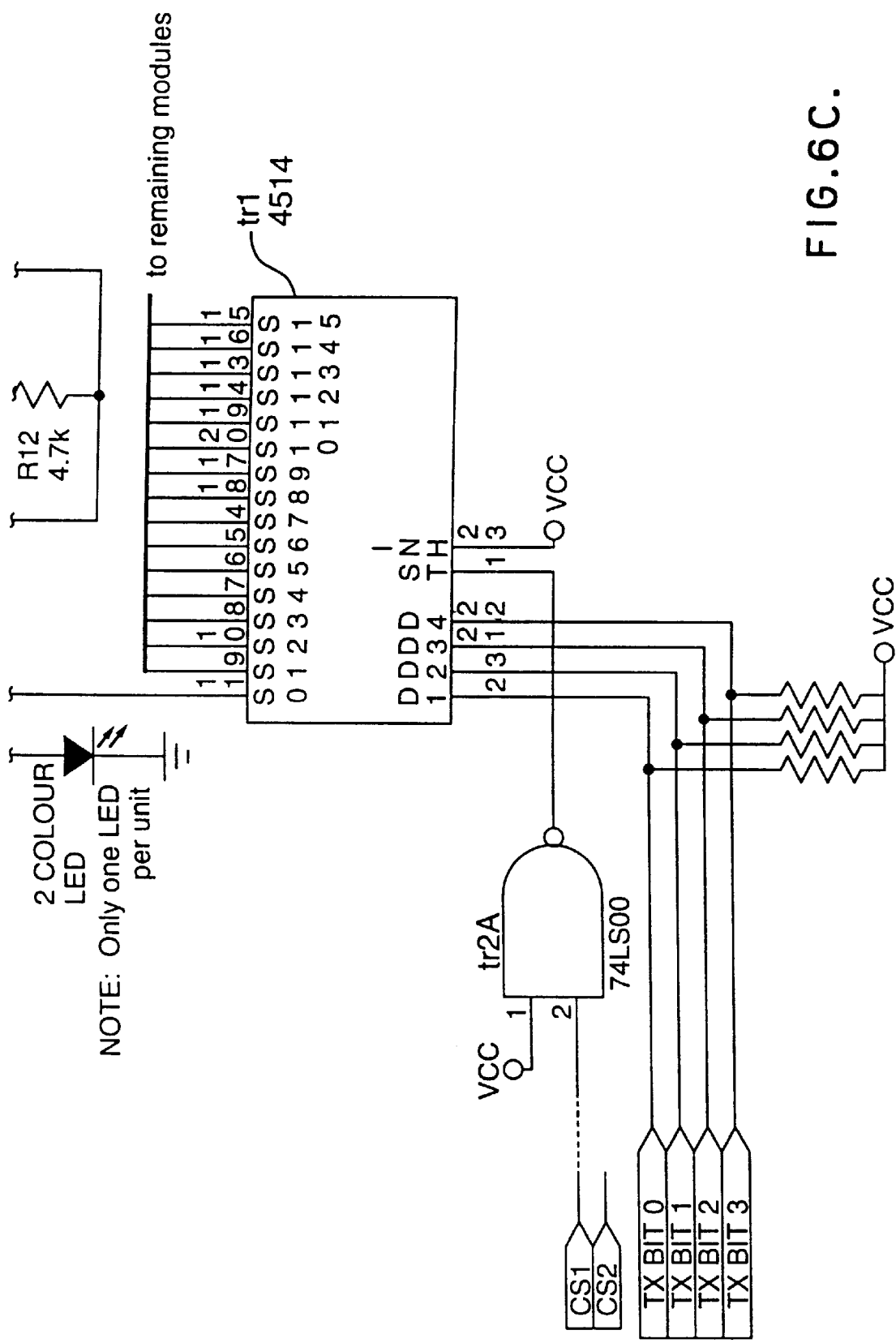
Figure 6D:
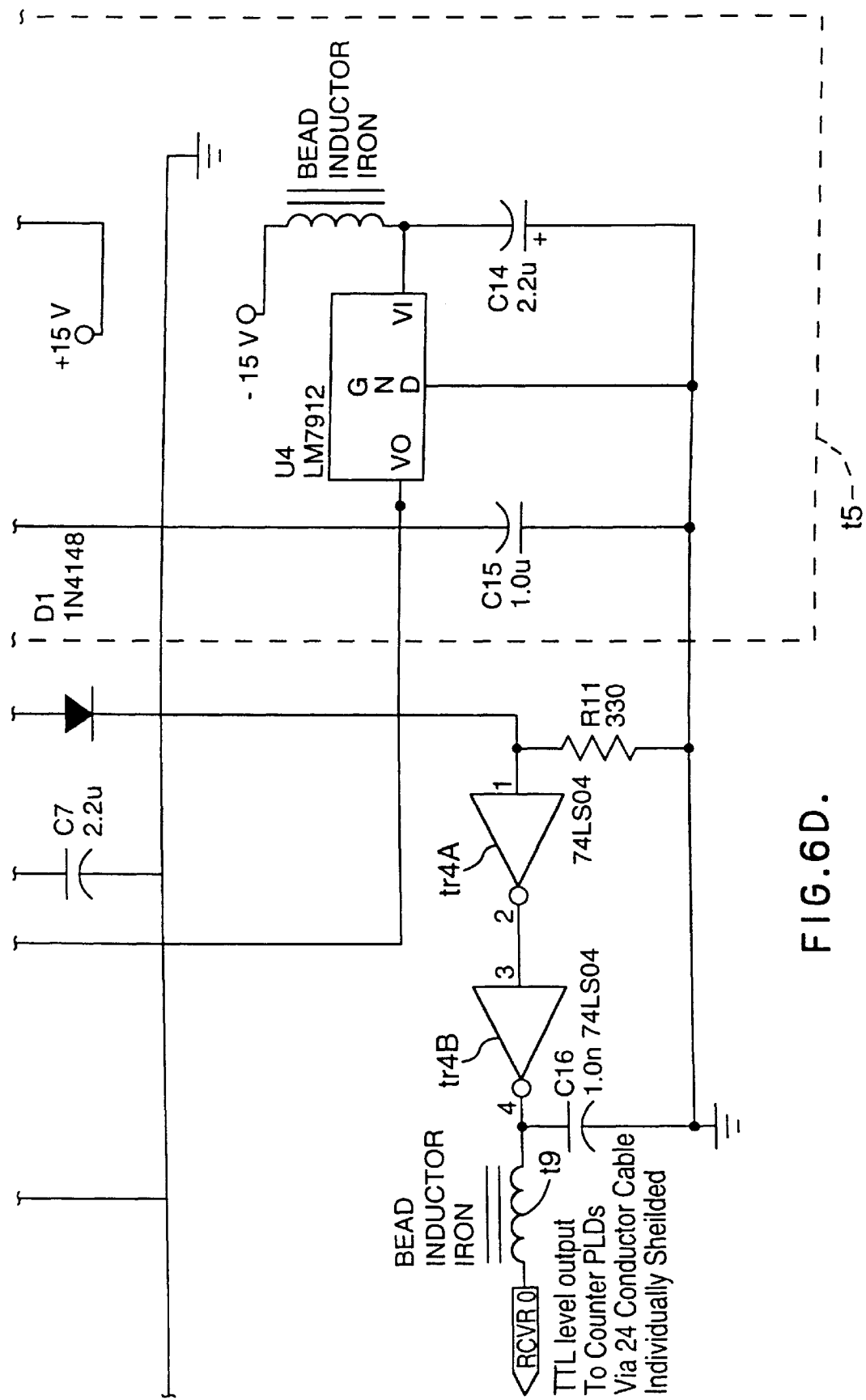

FIG. 2 is a block diagram of the computer interface and addressing scheme common to all three digital cards. It should be noted that the system is classified as an I/O mapping device as opposed to memory mapping device. Consequently, dedicated I/O registers within the controlling processor are responsible for all data throughput.

As illustrated in FIG. 2, the system computer interface architecture features a full two byte data transfer (D0–D15), as well as partial address decoding (A1–A13). Full two byte address decoding is not required. All signals sent to, or taken from the AT bus are buffered using octal buffers (d1 & d2) for both address and control lines, and transceivers (d3 & d4) for the data lines. In terms of decoding, each board features an eight position dip switch (d7) or equivalent for address selection. Address lines A6–A13 are used for this function, thus providing 256 distinct addressing locations, each with a resolution of 40 (hex) (i.e., 26). It should be noted that A0 is not used for address decoding.

An 8-bit magnitude comparator (d5) is used to equate the manually set dip switch with address lines polled by the computer mother board. When a match is found, a signal is generated which gates demultiplexes d8 and d9, each of which is a 1-of-8 demultiplexes. The lower three address lines (A1–A3) are used as inputs to both of these Read and Write demultiplexes. To distinguish their functionality, the buffered IOR signal is sent to opposite polarity enables on each demultiplexer. Thus if IOR is in a high state, the system computer interface is in a Write mode. To avoid Reading and Writing from the I/O address ports, A4 is also used as an opposite polarity input to do and do. This has the effect of offsetting the Reads from the Writes by precisely 10 (hex) (i.e., 24). The result of this is two controllable ranges of eight data bits used for gating "reads" from the digital boards, and "writes" to the digital boards. A single PLD (d6) serves to handle the glue logic between the other components of the decoder circuitry.

Due to the architecture of the x86 family of microprocessors, there are only a finite amount of I/O registers. These registers can be partitioned into either 65535 8-bit registers, or 32767 16-bit registers. Due to the nature of the data transfers to and from the boards, and by selection of an active low signal to the I/O CS16 input of the AT bus, only 16-bit data transfers are employed by the system.

The only remaining control line extending to the digital circuit card is the Address Enable (EN). This signal is used in conjunction with the I/O Read and I/O Write signals to gate the magnitude comparator (d5). By doing so, Direct Memory Access (IQMA) conflicts are avoided between the tracking system and other internal computer modules of the PC.

The first functional module in the ultrasonic 3-D tracking system of the present invention is the controller card. A functional diagram is provided in FIG. 3, which comprises FIGS. 3A, 3B, 3C, 3D, 3E, 3F, 3G, 3H, 3I, 3J, 3K, 3L, 3M, 3N, 3O, 3P and 3Q. The controller card employs the identical bus decoding scheme described above with reference to FIG. 2, to govern and pace the functionality of the overall system. As with all of the digital cards, the controller is preferably a four layer Printed Circuit Board, (PCB), with the embedded layers being the power and the ground planes, respectively.

The operation of the card is as follows: A single Programmable Logic Device (PLD), c1, is programmed to cycle through a full two byte count at 32 Mhz. The output registers of c1 are always active, so that the counter is constantly outputting a count value between 065535. These outputs are used for both comparative and timing purposes throughout the system. For this reason, a highly reliable, fast-response PLD is required. Functional blocks c2–c5 latch predetermined values from the decoding circuitry, and compare them to the output of c1. Thus, upon system start-up, specific values are written to the registers of c2–c5, and once those values are matched by the output of c1, respective signals are generated to govern such features as Pulse Length (6-bit), Cycle Length (8-bit), and Inhibit (15-bit). As illustrated, the "equating" outputs of the low data byte comparison (c2 & c5) require an edge triggering flip-flop (c11) to hold their equated state. The Output of the high data byte comparator (c4) is of sufficient duration to feed directly to c10 and c12. Using a 80 MHz clock, the Pulse Length signal is variable between 0 $\mu s$ and 2.00 $\mu s$ at 31.25 ns increments, the Inhibit signal between 0 $\mu s$ and 2.048 ms and 62.5 ns increments, and the Sub-Cycle Length signal is variable between 0 μs and 2.048 ms at 16 μs increments. Typical values are loaded into the registers of c2–c5 to best suit a given application, as discussed in greater detail below.

A second function of the c1 counter is to generate signals to a resetting 1-of-8 demultiplexes (c10) which in turn generates signals for application to c1 and c11 for resetting important system parameters. As can be seen in FIG. 3, one of these parameters is the Mode function which governs the direction of data flow in the octal transceivers located on the remaining system cards discussed in greater detail below. Four c1 outputs are also used to cycle through the RCVR lines of the system, thereby providing a default of 16 receiver modules.

A second major role of the controller card is to manage the performance of the transmitter activation bits. Using a transmitter PLD (c6) as a preloadable up counter, a value indicative of the start transmitter is latched to its input registers. Using an output of the c10 multiplexer as a clocking signal, c6 increments the six transmitter bits and outputs them both to a transparent buffer (c13), and to a 6-bit comparator (c9). Since the transmitter bits are sent to all three digital boards, as well as to the computer peripheral, the transparent buffer is required to avoid capacitive loading.

The ending transmit value is sent to the second side of the 6-bit comparator after it has been latched by c7. The octal latch (c8) is used simply to read the status of the transmitter bits by the controlling software. Once the 6-bit comparison is made and equated, a value is sent out to the local bus to clock the address incrementors on the remaining two digital cards. Although 6-bits are used for equating the transmitter increment bits, the default system allows for a 4-bit transmit value, corresponding to 16 possible transmitter channels. However, higher tier models of the ultrasonic tracking system of the present invention may employ up to 32 transmit cycles, corresponding to a 5-bit transmit value.

An 8-bit latch (c14) is also used by the system to generate and gate signals used to control address counters, interrupt controls, and trigger toggles.

Before most of the signals reach the local bus connecting the digital cards, they pass through c12, which is a simple "glue logic" PLD that ensures correct timing and signal polarity. This circuit module is also responsible for generating such parameters as the external system trigger for pacing and gating additional laboratory equipment.

Unlike the controller card which generates signals, the counter card (FIG. 4) receives signals to consolidate the ultrasonic distance information. The counter card features an external db25 connection to the transmitter/receiver/transceiver peripheral unit (FIG. 6). This twenty-four conductor, individually shielded connection between the counter card and the peripheral transmit/receive unit carries the 4-bit transmitter increment signals (TX BITS), the transmitter Pulse Length signals (CS1 and CS2) as well as the sixteen default receive lines accommodating 16 transmitter channels (upgradable to 32). Again it should be noted that not all embodiments of the ultrasonic 3-D tracking systems according to the present invention, employ the full range of sixteen receivers. Therefore, where a receive line is unused, it is grounded so as to avoid interfering with the desired signals.

A functional diagram of the counter card or module is provided in FIG. 4. The functionality of the counter module is best described in two stages, data writing and data reading. Examining the data writing stage, at precisely the moment when a valid signal is sent out by the external peripheral unit (FIG. 6) to activate a transmitting transducer, the expandable bank of receiver PLDs (s10–s13) are reset, to zero. These counters then count up from a zero value in accordance with respective internal 32 MHz clocks. Each PLD (s10–s13) is connected to an individual receive transducer (FIG. 6). As the 15-bit digital count in each PLD (s10–s13) is incremented past a predetermined value, an internal register within the PLD is activated which permits the reception of a receive signal. This predetermined value is used to implement the inhibit feature of the system and is designed to block out the electromagnetic interference caused by activating a transmit transducer. Once the mechanical vibration of the transmitted ultrasound is detected by a receive transducer it is converted to an electrical signal, amplified, filtered, and sent back to the appropriate counter PLD. This has the effect of stopping the digital count within the chip.

Next, a 1-of-16 multiplexer (s14) is activated for causing the output enable feature of the counters to be sequentially activated. The captured digital, value corresponding to the separation distance between the active transmitter and each connected receiver is then output in two bytes to the on-board RAM modules (s8 & s9) for temporary storage. Each time the RAM modules are activated, a default of sixteen locations are written to, according to the sixteen default receive signals. This cycle is then repeated for the next transmitter in the system. The incrementing of the RAM addresses is handled by s5, an octal buffer that outputs the 8-bit quantity representing the receiver/transmitter value at any time. Once all the transmitters in the system have been sequentially activated and recorded, the master cycle signal from the controller module triggers s1, the counter address incrementor PLD. This module then increments the RAM addresses to the next major block for the next transmit/receive master cycle.

Typically, the on-board RAM modules s8 & s9 are 8-bit by 131,072. Thus, in the-default configuration of sixteen transmitters and sixteen receivers, the RAM is cycled through 512 times before reaching its capacity. Options exist for upgrading the on-board RAM to 8-bit by 524,288, so as to allow for 2048 complete transmitter/receive cycles. It should be noted that for most biological investigations, a repetition frequency of 200 Hz is demanded. Thus, even with 256 kB of storage capacity (128kX2), the on-board RAM can be completely filled in as little as 2.56 seconds. Consequently, the system of the present invention includes software functionality for downloading the stored information. This process is described in greater detail below.

To successfully realize the data reading stage, the counter card or module monitors the addresses that are automatically incremented to the RAM, and writes values to those addresses. This task is carried out by the octal transceivers (s2 & s3). Using the Mode function generated by the controller card, the addressing data shifts from a reading to a writing state in accordance with the system timing. This gives the software the ability to activate any address in the RAM by simply writing out a 16-bit value to s2 and s3. Since the incrementing of the transmitter and receiver bits is automatic, there is no need to monitor their value. Thus, s4 can be simply an octal D-type flip-flop rather than an octal transceiver.

Once an address is written to the RAM for data output, the octal buffers s6 and s7 are opened to permit the PLD distance data to be passed along the low and high byte data paths into the I/O registers of the motherboard processor, then to the computer RAM, and finally to the hard disk for permanent storage. As can be seen in the system timing diagrams (FIGS. 7 & 8), the system is in a data output mode for the majority of each system cycle. Data input to the RAM occurs regularly, but only for 8 µs intervals.

A second major function of the counter module or card is to provide an analog signal output. Despite the fact that digital data acquisition is superior in many ways to conventional analog circuitry, many users are required to work with analog signals. The Digital-to-Analog (DAC) converter (s17) is thereby provided as an option on the standard tracking units of the preferred embodiment. The DAC of the present invention operates as follows. Successive 8-bit values are latched into one side of the one of four magnitude comparator (s15b, d, f & h). These values are selectable through the software to permit any combination of transmitter/receiver output signals to be transferred to the four analog outputs. The opposite side of each comparator (s15b, d, f & h), is directly connected to the constantly cycling transmitter and receiver bits. When the value applied to both sides of a comparator are equal, the output is passed to a 4-to-2 line encoder (s16), before being passed to a DAC (s17). Under this configuration, four distinct, 12-bit analog channels can be connected to an output port from the computer.

Finally the counter card or module also employ a "glue logic" PLD (s18) to coordinate the timing of the output enable signals, as well as the handling of thirty-two versus sixteen transmit channel capability.

It should be noted that the foregoing counter card is suitably replaced by other types of well known timer modules which are configured to measure transit time.

The final digital card or module in the ultrasonic 3-D tracking system of the present invention is a synchronized Analog to Digital (A/D) converter card or module. During typical experiments, a user may wish to acquire more than the networked distance measurements. For example, in a cardiac investigation, analog signals such as pressure, ECG, and blood flow are also important. For this reason, an expandable A/D card is integrated into the tracking system of the preferred embodiment. The basic system is perfectly provided with four A/D channels. However, up to sixteen independent, 12-bit channels may also be provided ranging from ±10V.

As illustrated in FIG. 5, the A/D module functions in virtually the same fashion as the counter card. Analog channels are fed in via a db25 cable connection (RGB174U coax connectors) to a1–a4. During the data input mode, all analog channels are internally converted fed into two 8-bit by 131,072 RAM modules (a6 & a7). The RAM is automatically incremented using the four gated receiver bits (a13). An incrementing address PLD (a14), which receives the same clock as the counter address incrementor, is used to provide the remaining thirteen address lines to the RAM. Thus, every time a complete transmit receive cycle is performed, both the A/D RAM and the counter RAM registers are increased. During the write, or data output mode, an address is written to the respective octal D-type flip-flop (a12) and transceivers (a10 & a11) to access the proper RAM location. The octal buffers a8 and a9 are opened allowing the converted analog information to be transmitted along the high and low byte data buses to the computer storage device. Finally, a controlling PLD (a5) is used to coordinate the timing signals on the A/D module. By congruously activating the A/D and counter information, it is possible to synchronize the digital distance information with the converted analog data.

A second function of the A/D card is to provide for direct digital inputs. Thus, up to four digital input channels may be received via latch a15 and monitored via octal buffer a8 during an experiment in the same fashion as the analog data.

The final hardware component in the ultrasonic 3-D tracking system of the present invention is the peripheral transmitter/receiver/transceiver unit, shown in FIG. 6. Each peripheral board of the preferred embodiment possesses the capacity to support sixteen transmitters with eight receivers, or eight transceivers. These components are mounted onto a two-layer printed circuit board and connected to the host computer system by means of the twenty-four conductor, individually shielded computer cable discussed above. The external peripheral unit receives its transmit voltage level and biasing voltages from an independent power supply (t5). The unit also possesses a two color LED to indicate whether the unit is in active or standby mode.

The peripheral unit works as follows. The digital signals from the computer to the unit are passed through pull up resistors to a CMS 1-of-16 decoder (try). The decoded signals are then transmitted to selectable transmitters or transceivers. The variable duration Pulse Length signal is sent via filtering and biasing elements to the gate of an N-Channel Enhancement Mode VMS transistor (Q). The gate signal bridges the transmit voltage level to ground. This signal is then passed through a step-up isolation transformer (TO) and out of the peripheral unit via a coated, 32 gauge, multi stranded wire (t2) to the transducer (x1).

The transducer (x1) is preferably a cylindrical piezoelectric ceramic crystal, encapsulated with an electrically insulating sealant.

Using a network of similar receivers, the mechanical vibration from a transmitter crystal is detected and converted to an electrical signal. Each individual receiver circuit consists of step-up isolation transformer (T1), a two stage amplifier (A1) collectively providing a 48 dB gain, a linear operational amplifier (tr3), a half-wave rectifier (D1) and a TTL level inverter (tr4A and tr4B). The digital waveform output from the TTL inverter is further isolated using an RF choke (t9) before it is transmitted back through the shielded cable to the appropriate LLDS.

According to the best mode of implementing the receiver, the single-ended amplifiers A1 may be replaced by a differential amplifier.

Figure 7A:
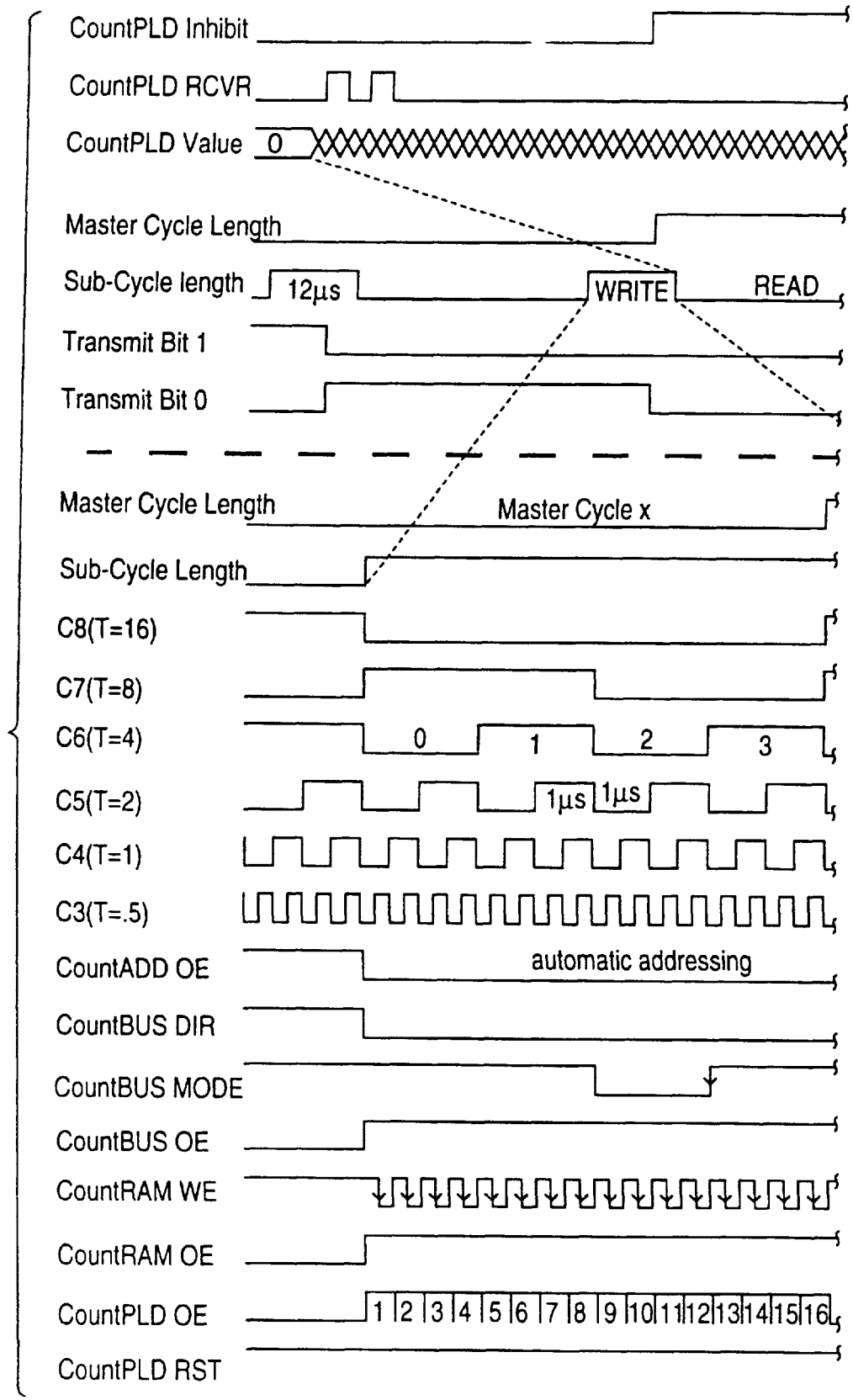
FIGS. 7A and 7B, is a timing diagram showing operation of the counter module according to the preferred embodiment.
Figure 7B:
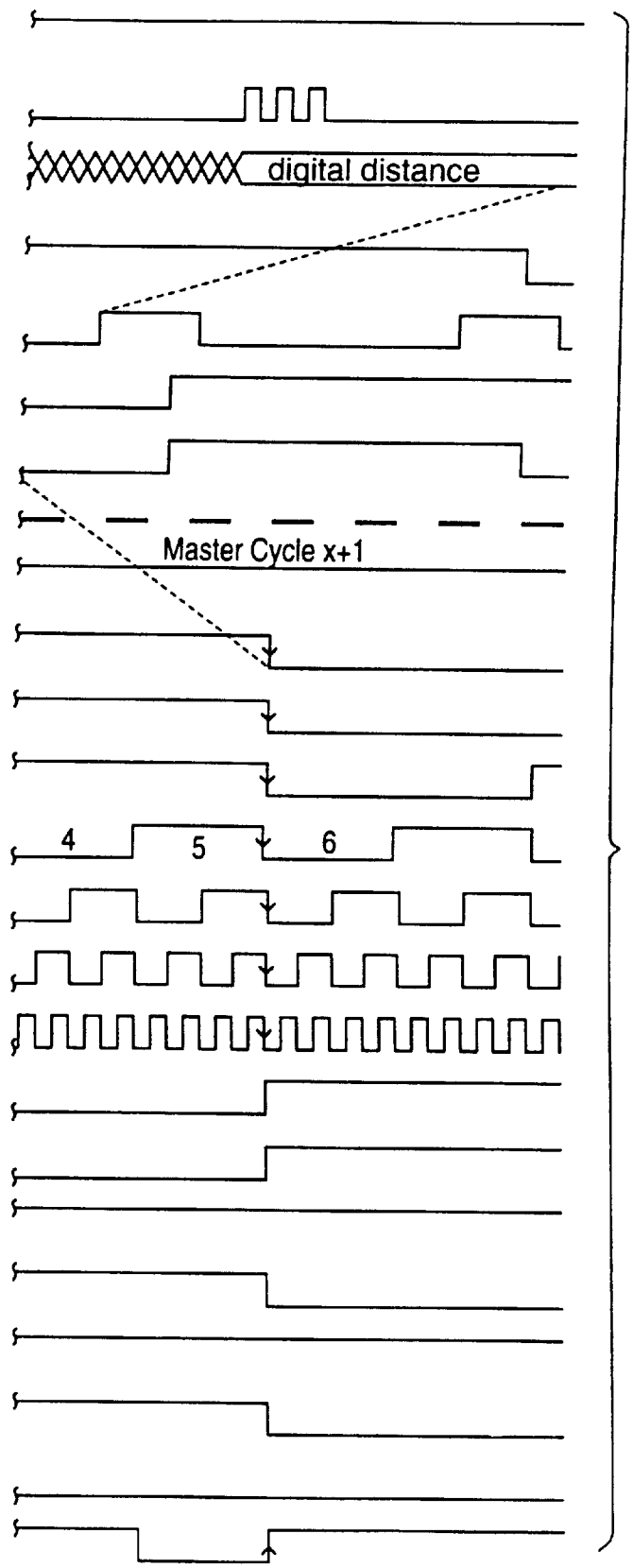
Figure 8A:
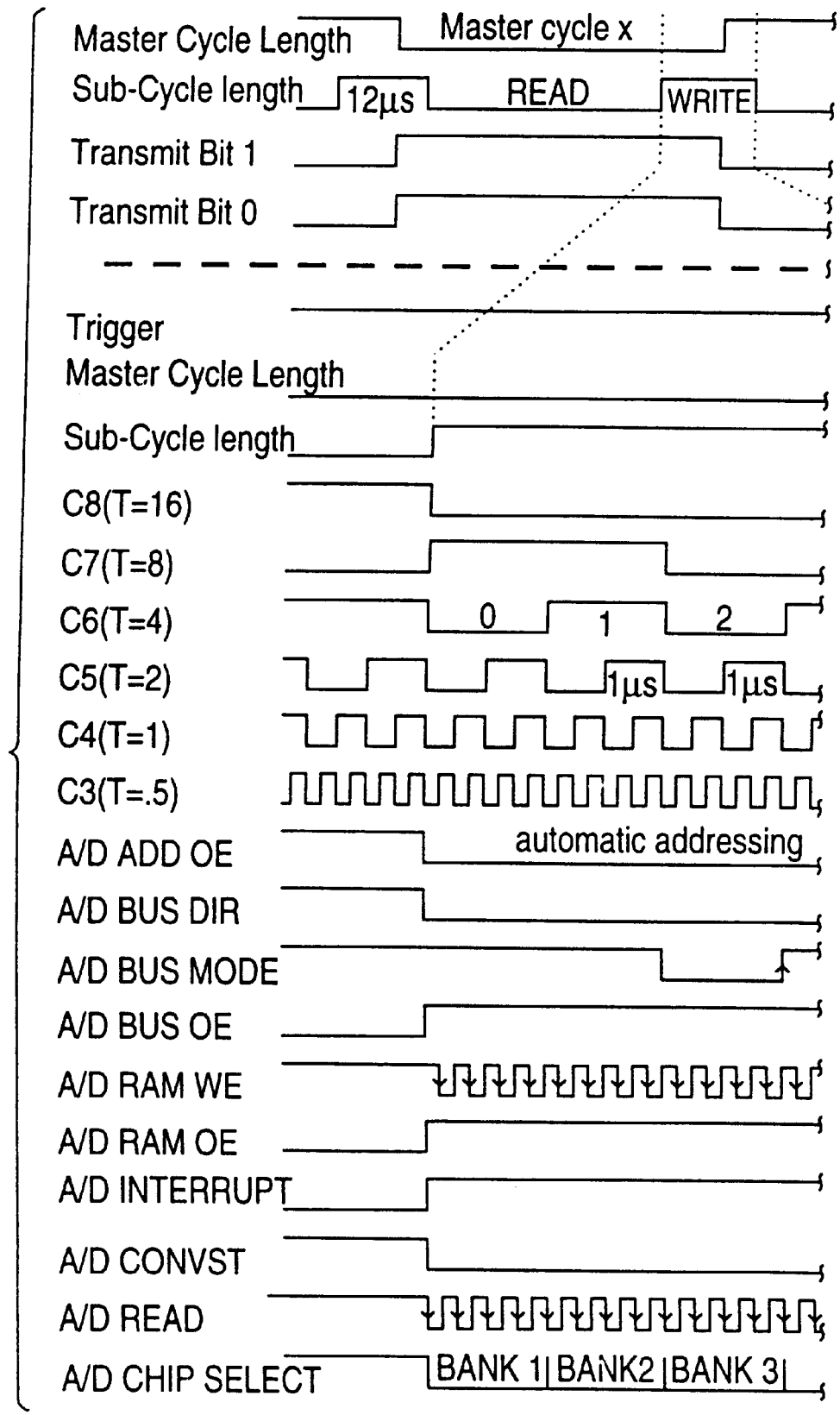
FIGS. 8A and 8B, is a timing diagram showing operation of the A/D module according to the preferred embodiment.
Figure 8B:
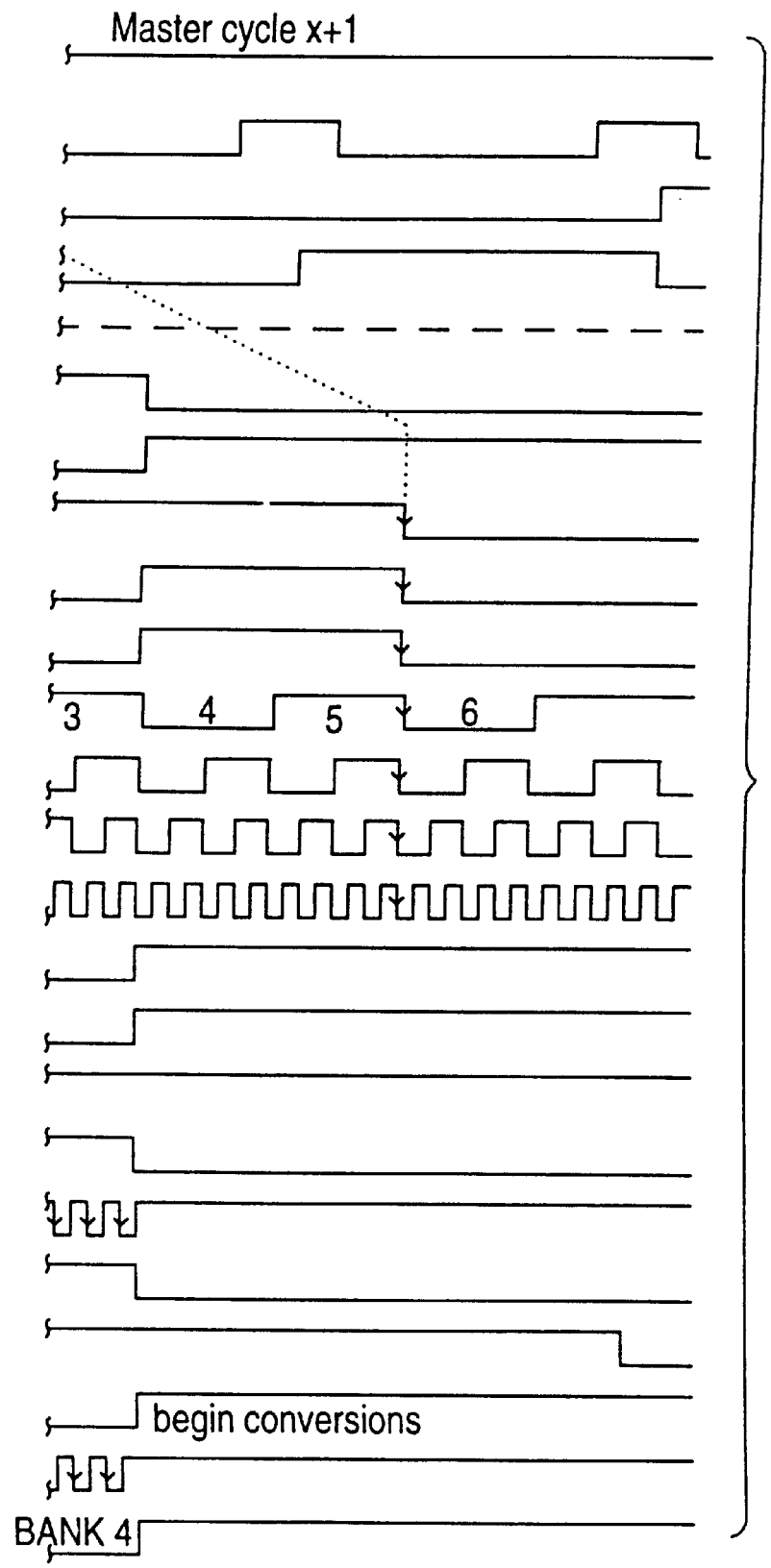

For a further understanding of the operation of the 3-D tracking system according to the present invention, a set of timing diagrams are provided in FIGS. 7 and 8. These figures illustrate the operation of the counter module (FIG. 4) and the A/D module (FIG. 5), respectively, during both the read and the write phases of operation. By default, the counter module actively acquires data for sixteen receivers during every Sub-Cycle Length. Conversely, the A/D data acquisition occurs only once during the same time interval, or once every Master Cycle Length. For simplicity, both timing diagrams are based on a transition from a transmitter "x" to a transmitter "x+1". Despite the apparent equal time-sharing between read and write cycles, in actual fact, the read cycle is significantly longer. More particularly, in the preferred embodiment the write cycle is limited to a 12 µs window per sub-cycle.

Referring to FIG. 7, the counter module (FIG. 4) operates as follows. At the beginning of the read cycle, an impulse signal is sent out to the VMS transistor (to in FIG. 6) to activate a transmit crystal (x1). At precisely the same time, the associated counter PLD (s10a–d, s13a–d) is released from its count of zero and begins counting up at a clock speed of 32 MHz. As discussed above, assertion of the CountPLD Inhibit signal prohibits electromagnetic interference between crystal leads by remaining at a logic low level. After a user-adjustable delay, the CountPLD signal changes state, thereby permitting the reception of a valid signal on the associated CountPLD RCVR line (RCVRO-3).

Once the first valid ultrasonic signal is detected and processed, the digital counter value is held on the PLD's output registers. The period of time for this distance count to occur is also variable in duration according to the user's specification. During this time, the transceivers which govern the read/write state of the system permit the downloading of the previously acquired digital distance values from the system RAM (s8, s9) (CountADD OE in a high state). By constantly monitoring the RAM addressing values using s2–s4 (FIG. 4) the computer is able to keep track of the RAM status. As the RAM (s8, s9, FIG. 4) approaches its capacity, a downloading is carried out during this read window.

The write window of operating the counter module is delimited by the 12 $\mu$s active high Sub-cycle length signal. At the moment this signal is asserted, the following conditions occur: the CountADD OE signal changes state, indicating that the automatic addressing mode has been invoked, the CountBUS DIR signal changes states to allow the opposite flow of data through the transceivers, the CountBUS OE signal is invoked to activate the output registers of the addressing PLD (s1) the CountRAM OE signal is disabled to prepare the RAM (s8, s9) for data storage, the CountPLD OE signal enables cycling through each of the sixteen individual counters, and the CountRAM WE signal toggles to store each digital count value in RAM (s8, s9). The signals used to control these functions are generated by various Boolean combinations of the control module counter (C.). As the default 4-bit receiver values are cycled through to produce the automatic RAM addressing, the CountBUS MODE signal is toggled to sample the current addressing value generated by the addressing PLD (s1, FIG. 4). This value is stored in memory for proper downloading of data during the next write window. These functions are carried out during the first 8 $\mu$s of the 12 $\mu$s sub-cycle window.

Once all sixteen receivers (FIG. 6) have downloaded their distance data to the RAM (s8, s9), the Master Cycle length value is incremented to indicate the next major cycle. At the same moment, the CountRAM WE signal is disabled along with the polling of the receiver distance values.

Finally the remaining 4, as expire putting the counter module back into its read mode, while resetting the receiver chips (COUNTPLD RST), and each of the incrementing counter bits from the controller card (FIG. 3).

Using FIG. 8 as a guide, the A/D module of the ultrasonic 3-D tracking system works in an identical fashion as the counter module, with one major exception. Write modes occur only during transition of the Master Cycle Length signal. When such occur, the default sixteen converted analog channels are cycled through and written to their respective RAM locations. The same A/D BUS MODE sampling occurs to ensure individual RAM chips are provided in banks of four channels, each chip is given a 2 $\mu$s window in which the A/D CHIP SELECT signal is toggled low for data throughput. At the end of 8 $\mu$s, the A/D parameters are reset to their write state while sampling of the analog channels begins once again. once the transition has occurred to activate the next array of transmitters, the AD INTERRUPT signal drops to a logic low value to indicate that the conversions of the active channels are complete.

The machine language codes that carry proper collection and processing of data acquired by the peripheral unit (FIG. 6) are all preferably based around a x86 processor. The transfer of information through the system is both quick and seamless. Given a typical system with sixteen transmitters and sixteen receivers, or sixteen transceivers, 256 2-byte distance data saves are carried out every cycle of the Master Cycle length signal. Since the on-board RAM (s8, s9) in a typical unit is 128 kB, the RAM has the capacity to save 512 Master Cycles before overwriting occurs. Since most clinical experiments typically demand a 200 Hz data saving rate to sufficiently track biological motion, only 2.56 seconds of data saving can be correctly obtained.

Since this is clearly unsatisfactory for a typical data run, software routines have been written for the system of the present invention to periodically download the RAM modules during the read cycles of the system.

The transfer of information out of the system is as follows: each time the digital boards (FIGS. 3–5) are accessed, a total of 1024 bytes of data are secured. This 1 kB is written to a dedicated 64 kB buffer in the mother board RAM of the resident PC. Provided that the computer is not responsible for carrying out any additional tasks, the machine language code implemented thereon, also shunts this information to the display. This function can be performed 64 times before the RAM buffer of the mother board RAM is full. Once this happens, the system software performs a binary save of the data held by the 64 kB buffer. At this stage, a standard disk-cache such as DOS's smartdrv.exe is activated to accept all of the 64 kB binary files and commit them to the hard disk drive of the PC at the end of a data save command. Under this scenario, the only limit to the duration of a data save is the capacity of the disk cache. In this manner, the ultrasonic 3-D tracking system of the present invention can be tailored to meet the specific needs of customers simply by providing additional memory to the base PC computer.

In addition to data saving and display software, the units according to the present invention preferably also utilize post-processing software routines to manipulate and visualize the saved binary data files.

Figure 16:
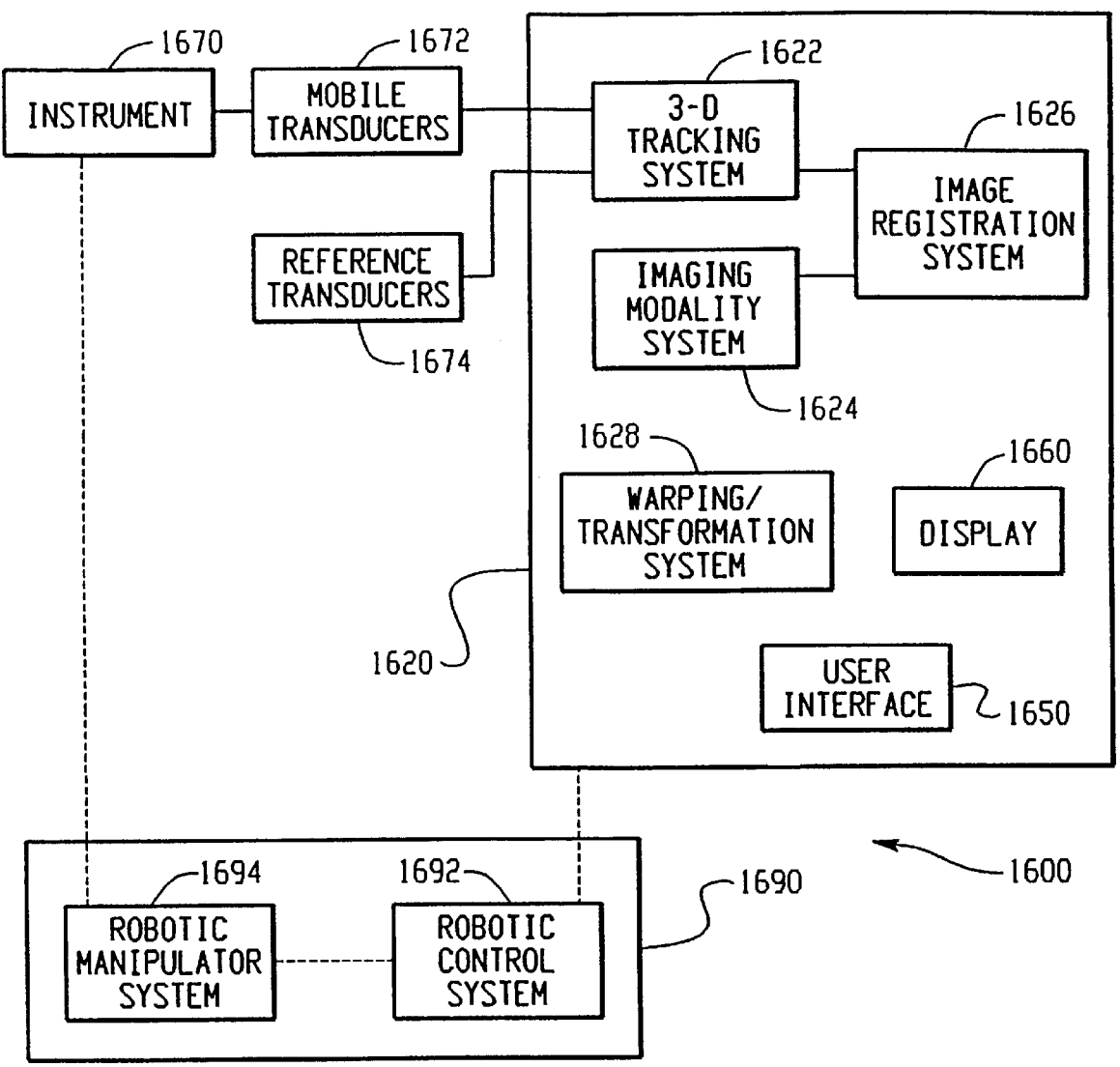
FIG. 16 is a block diagram of the 3-D tracking and imaging system according to a preferred embodiment of the present invention.

A three-dimensional (3-D) tracking and imaging system applicable for use in connection with a variety of procedures, including those described in detail below, will now be described with reference to FIG. 16. 3-D tracking and imaging system 1600 is generally comprised of a computer system 1620, mobile transducers 1672, reference transducers 1674, an instrument 1670 and an optional robotics subsystem 1690.

Computer system 1620 is generally comprised of a 3-D tracking system 1622, an imaging modality system 1624, an image registration system 1626, an image warping and geometry transformation system 1628 ("warp system"), a user interface 1650 and a display 1660. It should be appreciated that 3-D tracking system 1622 may take the form of a sound-based system or an electromagnetic-based system. Both time of flight and phase relationships may be used to determine distance.

Instrument 1670 may take the form of a catheter (e.g., see FIG. 10), a probe, a sensor, a needle, a scalpel, a forcep or other device used in a surgical or diagnostic procedure. Mobile transducers 1672 and reference transducers 1674 may take the form of an ultrasonic transducer or an electronic transducer. However, for purpose of illustrating a preferred embodiment of the present invention, transducers 1672 and 1674 will take the form of ultrasonic transducers (i.e., piezoelectric crystals) described above.

A plurality of mobile transducers 1672 are fitted to instrument 1670. One or more reference transducers 1674 provide a reference position relative to mobile transducers 1672. In this respect, reference transducers 1674 may be located to provide an internal reference frame inside a patient's body or on the surface of a patient body to provide an external reference frame.

As indicated above, reference transducers 1674 may be transmitters, transceivers or receivers that can generate ultrasound or electromagnetic radiation, that can be detected by mobile transducers 1672.

For the purpose of illustrating a preferred embodiment of the present invention, 3-D tracking system 1622 will take the form of the ultrasonic 3-D tracking system described in detail above. 3-D tracking system 1622 transforms the multiple distance measurements between all of the transducers 1672, 1674 into XYZ coordinates relative to a referenced axis, as described in detail above. It should be appreciated that the reference frame provided by reference transducers 1674 must be self-determining, that is, if the reference frame becomes distorted, this distortion needs to be detected by reference transducers 1674. Detection is typically done by using transceivers that can determine the distance between any combination of two transducers, and hence their relative spacial coordinates in 3-D space. In this regard, the position of the transducers is obtained in 3-D from the images acquired of the bodily structure (e.g., tissue/organ) that show "dots" where the transducers are located, and also from the transducers themselves when they are in the bodily structure. If there is some discrepancy in the distances between all combinations of transducers, then the bodily structure must have deformed (i.e., "warped") after the images were acquired. A mathematical coordinate transformation can be used to specify exactly how to correct the image set and account for the warping. The distance between any combination of two transducers is determined by having each transducer send a signal to all other transducers. In this way, all the distances between the transducers is known. From these distances, XYZ coordinates can be calculated, in reference to some transducer as the origin.

Imaging modality system 1624 acquires 2-D, 3-D or 4-D image data sets from an imaging source, such as fluoroscopy, an MRI (magnetic resonance imaging), CT (computerized tomography) or 2-D or 3-D ultrasound device, to provide a "template" through or against which the shape, position and movement of instrument 1670 being tracked can be displayed. The template typically takes the form of an image of the environment surrounding the instrument (e.g., a bodily structure). It should be noted that if multiple (3-D) volumes are acquired at different time intervals, a 4-D image is obtained (i.e., 3-D image changing over time).

Image registration system 1626 registers the position of instrument 1570 within the spatial coordinates of the image data set provided by imaging modality system 1624. The position of instrument 1670 is provided by the 3-D tracking system 1622. Image registration system 1626 will provide a display of instrument 1670 at its proper 3-D location inside the bodily structure and orientation relative to the bodily structure itself. It should be appreciated that registration system 1626 may be user assisted, or completely automated if image processing algorithms are implemented to automatically detect the spacial locations of the transducers (typically the reference transducers) in the image data set.

Warp system 1628 is a software-based system that transforms or "warps" the image data sets by the appropriate values to correspond to a deformation that has occurred in the reference frame between the time that the image data set were acquired and the time that the procedure is to be implemented during surgery. Accordingly, warp system 1628 is typically comprised of a matrix transformation routine that maps the deformed geometry onto the original image data set, and distorts it appropriately.

User interface 1650 enables a user to interact with computer system 1620, including programming computer system 1620 to perform a desired function. For example, a particular view for display can be selected. Instruments 1670 (e.g., probes or catheters) can be activated using user interface 1650. Display 1660 displays to the user registered images provided by image registration system 1626.

Optional robotics system 1690 is generally comprised of a robotics control system 1692 and a robotic manipulator system 1694. Robotics control system 1692 controls robotic manipulator system 1694 to follow a programmed path that can be appropriately changed, based on shifting, warping or changes in the shape of a bodily structure at the time of surgery. Robotic manipulator system 1694 physically moves instrument 1670 as instructed by robotic control system 1692.

As discussed above, 3-D tracking and imaging system 1600 can display existing or user acquired image data sets as a template through which, or against which the position, shape or motion of an instrument can be referenced inside the body or organ. The algorithm for carrying out this feature will now be described with reference to FIG. 11. It should be appreciated that portions of the "Path 1" algorithm can run both on the PC that houses the circuit boards embodying FIGS. 2–6 ("PC"), and/or in a separate computer (not shown) or workstation ("WS") with additional processing power and 3-D visualization capability.

The process begins with the PC that houses the digital circuit boards. The PC completes a data acquisition cycle and has many numbers in memory, each corresponding to a time that the ultrasound pulse took to travel the distance between all combinations of transducers within the measuring volume (module 1100). Within this volume, there exist a number of mobile transducers mounted on the instruments being tracked(see FIG. 9), as well as reference transducers located on the patient in strategic reference locations (see FIG. 15). The reference transducers may be mounted internal to the patient to provide an internal reference frame, or mounted external to provide an external reference frame. This propagation delay measure, or "signal", can be corrupted with noise, accordingly some signal processing may be need to be performed to recover the likely values of the original signal (module 1102). This can be done by testing for the range of the signal, and by smoothing or predictive fitting to previous trajectories of the data signal.

Following signal processing, the improved "signal" is converted in the PC, according to the methodology discussed in detail above with reference to FIGS. 2–8, into "data" that correspond to real measurements of distance between pairs of transducers. This is done by converting the propagation delay into a distance measurement by taking into account the speed of sound in the particular medium. This conversion can be a simple linear process, or can be scaled non-linearly, depending on the likely medium through which the sound is propagating. The output of this conversion is distance measurement "data" (module 1104).

It should be appreciated that the distance measurement data may be corrupted due to signal dropouts resulting from poor signal propagation throughout the measurement volume. However, there usually are more than enough individual distance measurements available to reconstruct the 3-D location of the transducers, since many extra distances between transducer pairs are obtained. A process of "data filling" can be performed to fill in the missing data, based on the many combinations of other distance measurements that are available. "Data filling" can be done using a multidimensional scaling algorithm, or variants of it. "Data filling" is an iterative process and is typically done on the computer workstation ("WS"). The output of the "data filling" preprocessing step is more complete data.

The data output from module 1106 is then converted (in a well known manner using geometric algorithms) into 3-D coordinates of the points that are being tracked (module 1108). These 3-D coordinates are passed to a 3-D scene relationship and evaluation module that takes the 3-D coordinates, and based on previously obtained information from user input or a library database, arranges the coordinates in the correct sequence to construct 3-D structures (module 1110). For example, it would be known in advance that, for example, transducers numbered 3, 5, 6 and 9 are mounted on a predetermined one of the instruments (e.g., a catheter), so the coordinates of the transducers mounted to the instrument would be connected together. The scene relationship and evaluation module would then construct a 3-D image that would represent the position, size and shape of the instrument, based on the 3-D coordinates of the individual transducers mounted to the instrument body.

In a similar manner, the transducers mounted to the instrument can be located in such a way as to build up a 3-D surface patch image of a bodily structure, such as an organ. For example, transducers mounted to a catheter can be located in such a way as to build up a 3-D surface patch image of the inside of a beating ventricle, by simply dragging the catheter along the wall of the ventricle in the area of interest.

Figure 15:
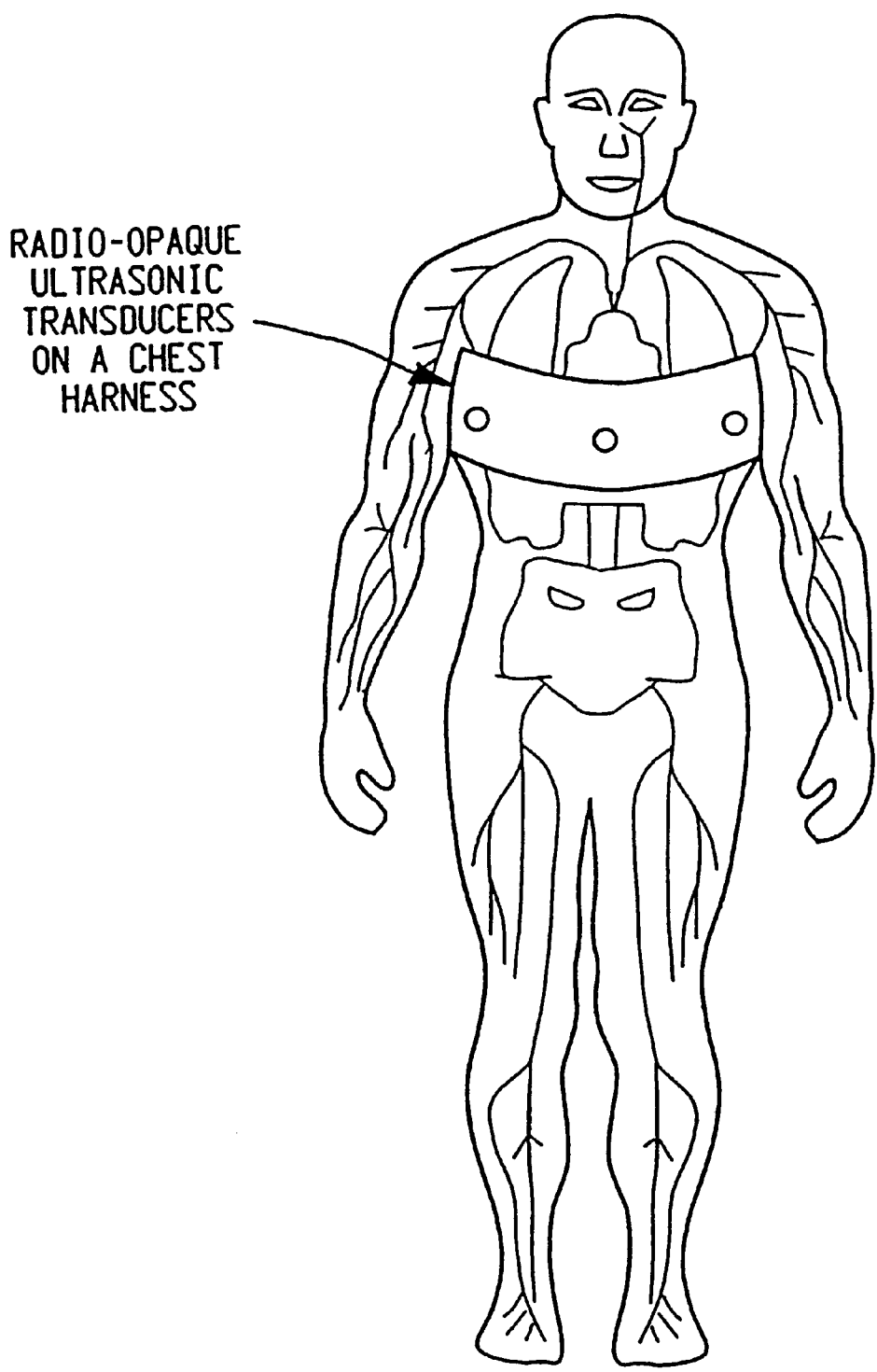
FIG. 15 is a schematic illustration of a chest harness having reference transducers mounted thereon to provide an external reference frame according to the catheter guidance system shown in implementation of FIG. 9.

The output of module 1110 is a '3-D scene' that contains many of the elements being processed, some of which represent the instrument and the individual transducers affixed to the patient (FIG. 15). The 3-D scene is then rendered by a 3-D graphics subsystem rendering/display (module 1112) and output to a display.

If the instrument is stationary, the 3-D scene does not need to be re-rendered or updated in any way. Therefore, a module 1114 is provided that detects any changes in the stream of incoming data. If there are changes, this module signals another module 1116 that determines whether the new 3-D coordinates that have been acquired and processed by the WS have changed significantly from the previously rendered objects or scene. If they have, then this updated information is incorporated into the existing model of the 2-D scene and passed onto the rendering/display module 1112.

The display of the instruments is only one component of the scene relationship and visualization module 1110. In this regard, the instruments need to be displayed in reference to some recognizable features, such as a 2-D or 3-D image showing the environment surrounding the instrument. The algorithm for carrying out external image acquisition is shown schematically in FIG. 11 as "Path 2", and begins with the input of an image from an external image modality (module 1118). As discussed above, system 1600 includes an imagining modality system 1624 providing externally acquired image data sets in 2-D or 3-D form. It should be appreciated that these 2-D or 3-D images may already be in digital form, or may be analog data input directly from a live video source using a frame grabber.

The acquired image data sets must first be converted into a format that is suitable for processing and manipulation inside the WS (module 1120). Accordingly, any analog data is converted to digit data. Therefore, the image data sets that are output from module 1120 are "digital images" that can be manipulated further inside the WS.

The image data sets may need to be preprocessed in some way to make them fit appropriately into the 3-D scene. For instance, if they are to be shown along with the instruments, the image data sets may need to be scaled appropriately. If the images are to be moving, they will need to be updated or reformatted in memory so that they can be output to the 3-D scene rendering/display module 1112 in the correct sequence. Any such manipulation is performed by the preprocessing module 1122. Moreover, for video information, an appropriate sync signal is required for appropriate sequencing (module 1124).

One of the most critical aspects of the 3-D scene relationship and evaluation module 1110 is the placement of the 3-D image of the instrument in the correct spatial relationship with the underlying images showing the environment surrounding the instrument. This is done by registering features in the images, such as the reference transducers, with their position in the measuring coordinate system. This process uses standard coordinate transformation operations, and only requires for input information as to which feature in the image space corresponds to the same feature (i.e., transducer) in the measurement space. This information can be input by the user during initial set up (module 1126), or can be automatically detected using image processing algorithms. Once the instrument image is registered with the underlying images, the information describing the image set that is to be displayed at a given instant is sent to the 3-D scene relationship evaluator module 1110. Additionally, to test whether new image information has arrived and needs to be used, an appropriate signal is sent to module 1114 that detects changes and instructs the system to update the scene.

Figure 11:
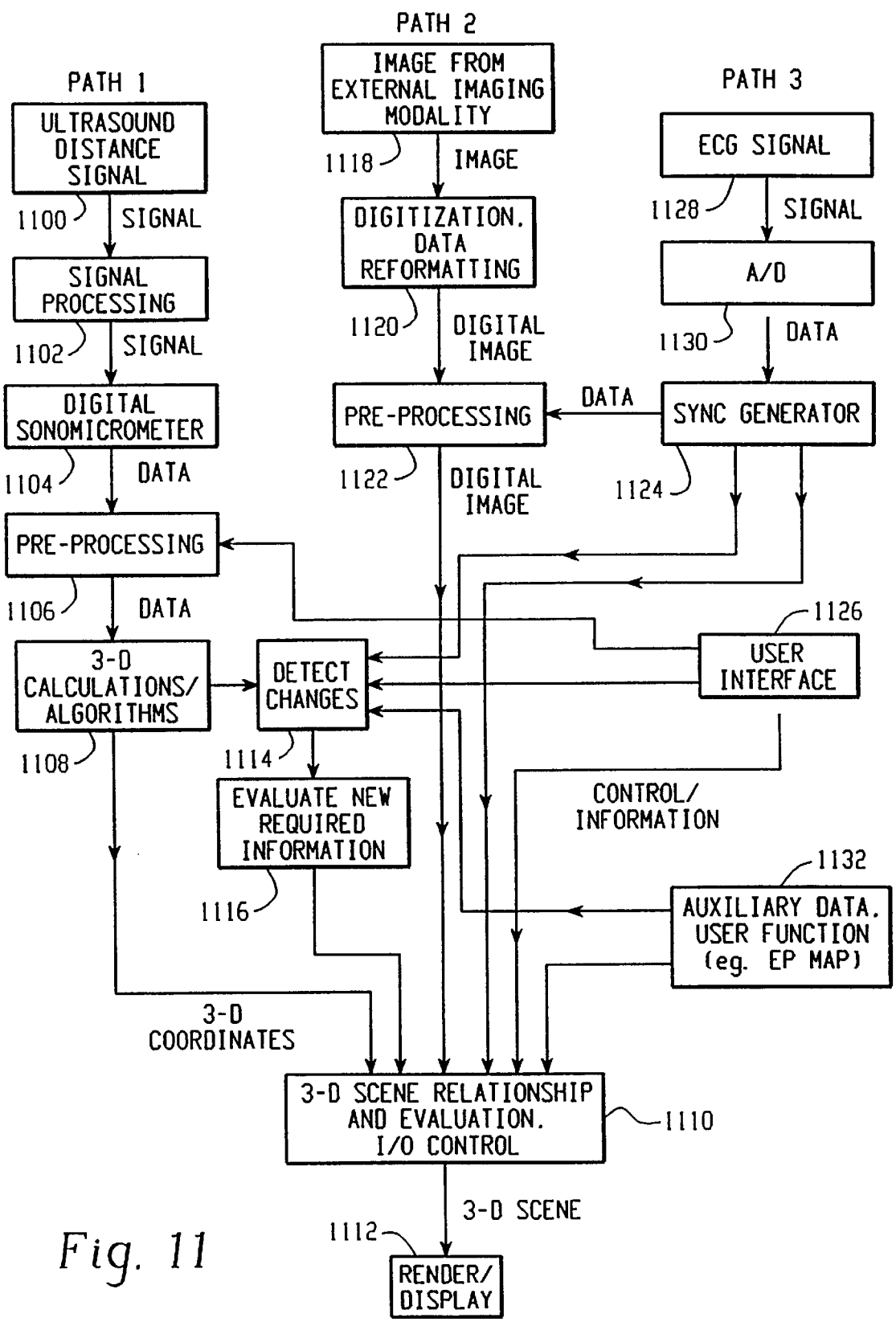
FIG. 11 is a flow chart of a 3-D visualization algorithm for displaying the position of the device being tracked by the tracking system of the present invention.

For moving image sets, such as 2-D video loops, or 3-D ultrasound loops of the heart, the motion of the image data sets need to be output at a rate that continually matches that of the patient heart beat (see Path 3 in FIG. 11). If the image data set that is played back is not synchronized with the current state of the heart, then the 3-D scene will not be displayed in a recognizable format and abnormal motion of the catheters relative to the images, will result.

The first step in synchronizing "video loops" with a patient's heart beat is to input a raw ECG signal into the processing computer (module 1128). The ECG signal is converted into digital data using a standard A/D converter (module 1130). The digital data is then fed into sync generator module 1124, which includes an algorithm that produces a timing signal that corresponds to the current activity of the heart. For example, the sync generator module 1124 can activate a memory location or an input port, or generate an interrupt, at the precise time that a QRS complex is identified. The sync generator module 1124 does this by following the input signal and testing for large rates of change, combined with zero crossing and other information relevant to the expected morphology of the signal. The sync generator module 1124 can run in the PC, the WS, or an external device designed to identify QRS complexes and output a sync signal to the WS.

Control information is provided by the user interface (module 1126), discussed above. The user interface checks for user input from a keyboard and/or mouse and sends appropriate control information to the 3-D scene generator (module 1110), and to other modules that can be affected by the user input. Typically, user input would involve the modification of the type of information that is to be displayed on the display screen, and not the way the signals are processed. The user can also assist in registering the catheter location of the instrument with the underlying image set.

The system also has a provision for the merging of other auxiliary data information, such as the display of electric potential over any 3-D structures that are displayed (module 1132). This information is peripheral to this main system, and is assembled in a way that can be readily incorporated into the 3-D scene generator (module 1110).

Figure 12:
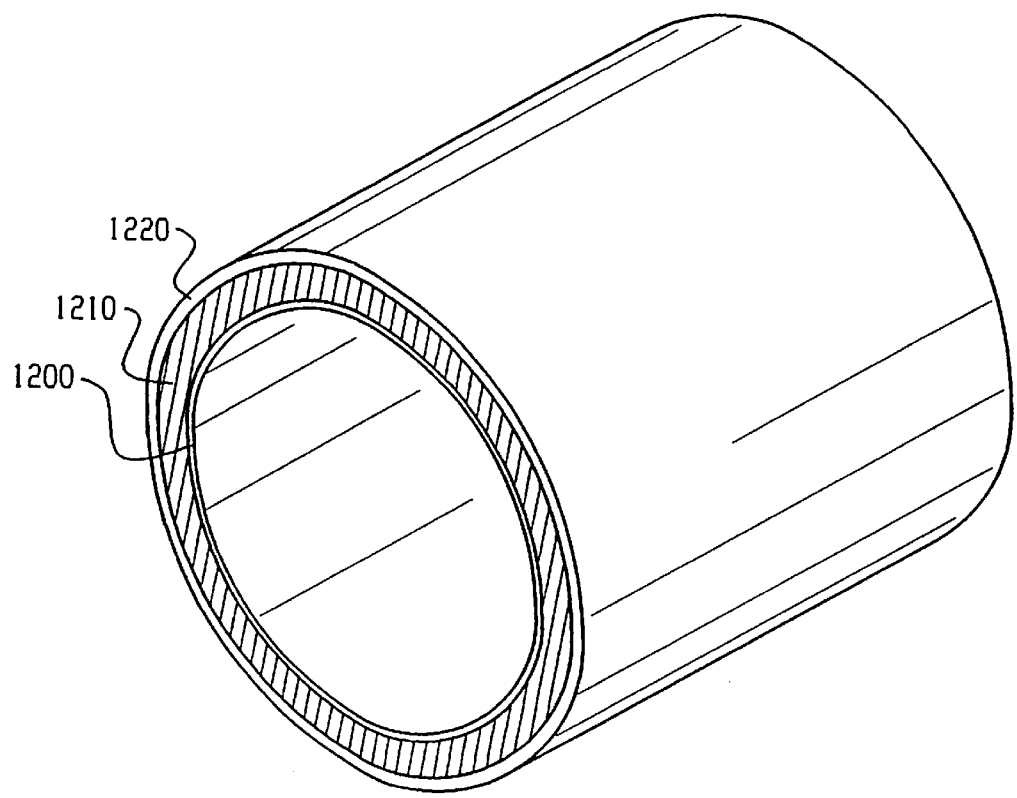
FIG. 12 is a perspective view of a cylindrical or ring-shaped transducer according to a first alternative embodiment.

As indicated above, the transducer of the present invention may take many forms. According to a first alternative embodiment, a cylindrical or ring shaped ultrasonic transducer is provided, as shown in FIG. 12, for attachment to an instrument (e.g., a catheter or other probe), for the purpose of tracking its position in three dimensions inside the body or organ. The transducers can be either rigid or flexible. If they are rigid, they are typically constructed from PZT material, and cast or milled into an appropriate shape. If the transducers are made flexible, they are typically constructed from PVDF material that is laminated onto the surface of an instrument. This material is flexible and can be applied to rounded surfaces. As a result of the relatively low transmit efficiency of PVDF material, it is likely to be used for a transducer used in receive mode only. The geometry of the crystal preferably has principal mode of vibration in the 100 kilohertz to 4 megahertz range, or in the range referred to as "low frequency ultrasound". The transducers are polarized along a principal axis (i.e., either through the wall thickness, or along the cylindrical axis) and the appropriate surfaces are coated with a conductive material to facilitate connection to leads. If the material is poled through the wall thickness, then the inner and outer surfaces of the cylinder are plated and conductors are affixed thereto. While the size of the transducer will depend on the application of the tracking technology, the inner diameter of the cylinder is typically 5 millimeters or less for catheters and 5 millimeters or more for larger endoscopic probes. It should also be appreciated that several sections of a cylinder may be placed around the instrument of interest, thus making each individual transducer small for ease of manufacture, mounting or to control resonant frequency.

As shown in FIG. 12, the cylindrical crystal or transducer may incorporate a lossy backing 1200 on which the piezoelectric material 1210 is disposed. The lossy backing prevents excessive ringing of the PZT material. As the crystal is energized, an ultrasound wave propagates both forward and backward. When the ultrasound wave reaches the interface between the crystal and the outside medium (e.g., water or air) it meets an impedance mismatch and most of the wave bounces back into the crystal. This is why the crystal rings for many cycles. The lossy backing enables the backwards traveling wave to exit the crystal (i.e., it has similar impedance) and dissipate with minimal reflection. The backing material is typically-epoxy with tungsten powder mixed in. Ideally, the backing material should be many times thicker than the crystal itself.

The piezoelectric material 1210 may be coated with a ¼ wavelength matching layer of ultrasound conductive material 1220 (e.g., polymer material). Electrically conductive wires (not shown) are connected to the piezoelectric material. As discussed above, the forward propagating wave of ultrasound typically bounces off of the crystal/water interface, unless some impedance matching material is provided. The purpose of this material is to provide an intermediate impedance between water and PZT so that at each material interface there is less mismatch, and more of the ultrasound wave propagates forward, rather than reflecting backward. Typically one or two layers are deposited on the crystal with intermediate impedances. The thickness of the layers must be ¼ of the wavelength of the ultrasound wave so that destructive interface occurs between the reflected waves, thus reducing the ringing of the crystal.

If PVDF is used for the piezoelectric material 1210, then the film or material can be wrapped around the instrument, or could be molded or cast directly upon it, essentially becoming a component of the instrument. It is also contemplated that an existing instrument (.e.g., catheter) can be retrofitted with PVDF material in accordance with the embodiment of FIG. 12, to facilitate tracking thereof inside the body. It is also contemplated that the piezoelectric film (e.g., PVDF) can be wrapped, cast or deposited over the instrument in several locations.

Figure 13B:
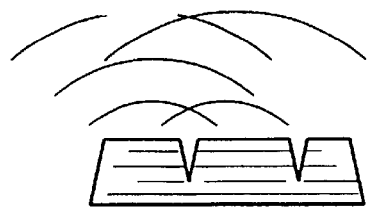
FIG. 13 is a perspective view of a ring-shaped array of transducers, according to a second alternative embodiment.
Figure 13C:
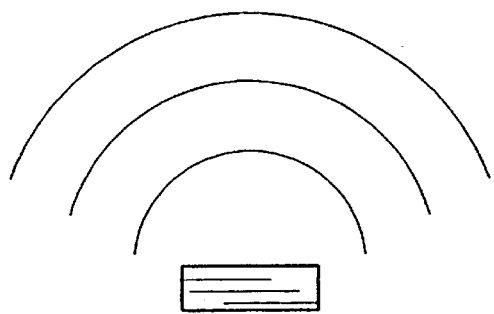
Figure 13A:
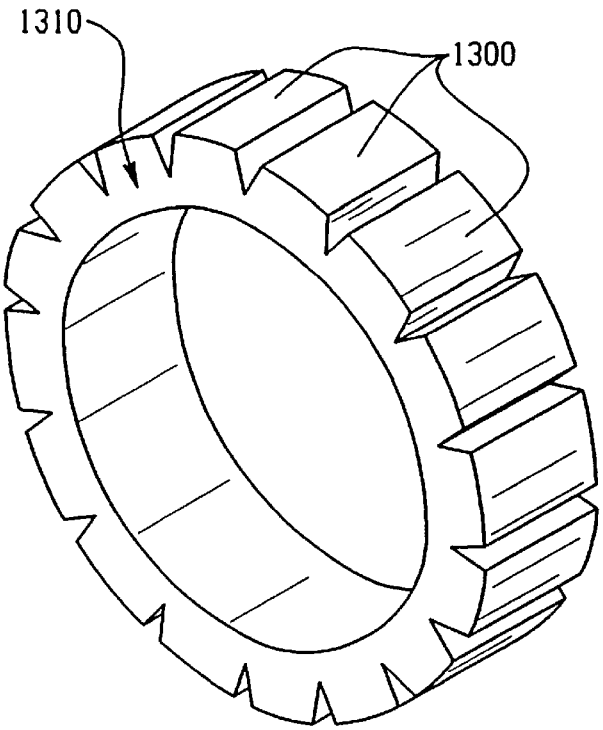

According to a second alternative embodiment for the ultrasonic transducer, a ring-shaped array of crystals, or a segmented single crystal can be provided, as shown in FIG. 13A, with a configuration that enables the ultrasound energy to radiate at a large angle away from perpendicular to the axis of the cylinder, such that the crystal array functions as a line source of ultrasound energy, or as a collection of point sources, each radiating ultrasound energy in a fan substantially away from the plane of the cylinder, as shown in FIGS. 13B and 13C.

The crystal is provided with a plurality of facets 1300, each being in the order of a millimeter in size, so as to resonate individually at a resonant frequency dictated by the size of the facet, rather than the size of the entire ring. The ring is plated with a conductor 1310 on both sides, as depicted in FIG. 13, rather than on the inner and outer surfaces thereof.

Figure 14:
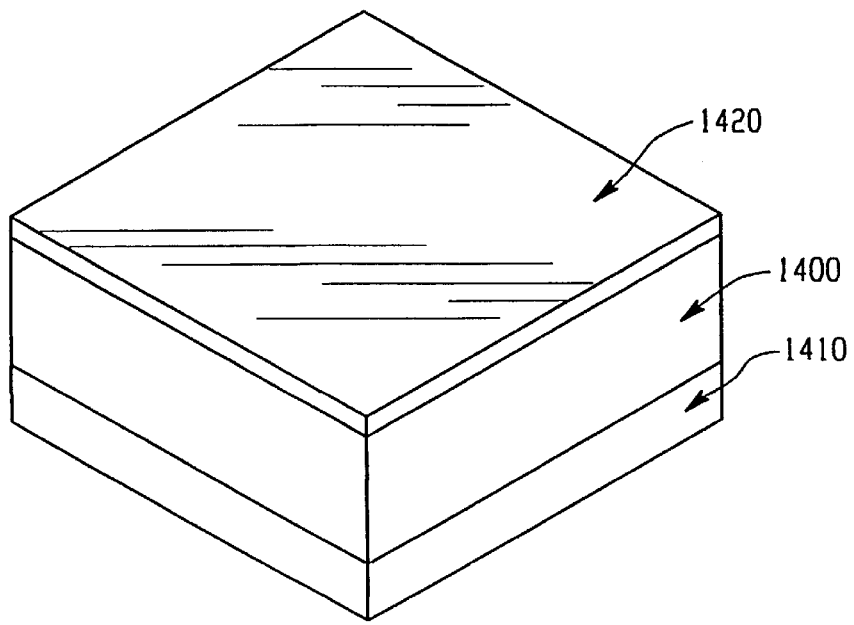
FIG. 14 is a perspective view of a composite transducer, according to a third alternative embodiment.

According to a third embodiment of the transducer, a composite ultrasonic transducer is provided comprising a PZT substrate 1400 on a lossy backing 1410. A PVDF film 142Q is bonded to the PZT substrate 1400. This embodiment offers the advantages of high transmitting efficiency of PZT (i.e., conversion of electrical energy into acoustical energy) and the high receiving efficiency of PVDF (i.e., conversion of acoustical energy into electrical energy). It is contemplated that the PVDF and PZT films 1420 and 1400 can be directly connected (as shown), or electrically isolated with appropriate layers of insulator or conductor therebetween. It is also contemplated that the PVDF or PZT structure can be in the form of a slab, as shown in FIG. 14, or can be cylindrical, as in the embodiments of FIGS. 9, 10, 12 or 13.

FIG. 15 illustrates the manner in which the external reference transducers are placed. The purpose of the external reference transducer is to provide an external reference frame (i.e., outside the body) to monitor the accuracy and movement of the transducers mounted on the instrument. As can be seen, the transducers are placed in a harness-type apparatus that is worn around the chest by the patient during a surgical procedure. A number of radio-opaque transducers are fastened to the harness in locations suitable for optimal signal reception through the chest cavity. Alternatively, the external reference transducer may be affixed directly to the patient at strategic locations, using self adhesive mounting film or adhesive tape.

Under the disclosed configuration, it is possible to monitor the position and direction of the instruments that are introduced into the body, (e.g., catheters introduced into the human circulatory system). This methodology significantly reduces both the risk and the procedural time associated with current electrophysiology and angiology operations, while providing improved positioning accuracy.

A detailed description follows, relating to specific clinical applications of the 3-D tracking and imaging system according to a preferred embodiment of the present invention.

i) Tracking of Catheters Through the Human Circulatory System

Catheters are devices that are inserted into the veins or arteries of humans as part of a procedure in which qualified hospital personnel, remove blockages and obstructions from the circulatory system, or correct other related problems. The 3-D tracking and imaging system of the present invention may be configured to operate as a catheter guidance system that can be used to track various types of catheters, probes and other instruments.

The current method of tracking catheters involves frequent exposure of the patient to an x-ray source. Each successive x-ray provides information on the movement of the catheters within the patient. In addition, contrast agents are frequently injected into patients during catheter procedures. These injections can provide further information on the actual location of the catheter and help physicians to plan subsequent catheter movements.

X-ray radiation and contrast agent injections are each potentially harmful to the health of the patient. Further, these methods of tracking are also time consuming, often introducing additional stress and patient complications.

Three primary advantages result from the present invention when used to track catheters:

1) The need for using harmful x-rays and contrast agents are virtually eliminated while determining the location of catheters) within the patient;
2) Procedure times are substantially reduced with benefits in both safety and cost; and
3) Extremely exact positioning of the catheter is obtained as a result of the theoretical resolution of 19 μm, according to the present embodiment of the system.

The basic principle of the catheter guidance system (CGS) of the present invention involves the establishment of an internal reference frame and an (optional) external reference frame in three dimensions from which the catheter can be tracked. Using the transceiver hardware and the triangulation algorithm discussed above, the crystal positioning data can be captured and processed to resolve the location of the catheter of interest.

To further facilitate visualization of the catheter location by the administering hospital staff, the transducer position information may be overlaid onto a recorded video loop of the region of interest. This video loop can be generated from an imaging modality such as x-ray or scanning ultrasound and is meant to illustrate the natural movement of the biological structures during one or more cardiac cycles. In addition to this, the video loop can also depict the position of the opaque piezoelectric crystals (X1) used by the CGS to track the catheters. These piezoelectric crystals serve as "landmarks" (whether they are internal or external). By identifying these "landmarks" in the video, the positions of the guiding piezoelectric crystals can be correlated with the captured video information. In this fashion, the imaging process and the ultrasound positioning process can be linked for one or more complete cardiac cycles. Once the imaging modalities are linked, the graphic video loop can be substituted for the potentially harmful imaging (and contrast agent injections) throughout the rest of the procedure.

Typically, the catheters used in these procedures are introduced into the body through the femoral vein or artery. From the point of entry, the catheters are pushed and steered, using internal guide wires to the region of interest, usually the human heart. Physically, the catheters are constructed with a biocompatible plastic and feature such options as electrode sensors and actuators for detecting the cardiac activity in electrophysical operations to inflatable balloons for arterial expansion in angiology procedures.

A concept that is of importance in implementing the CGS application of the present invention is the merging of piezoelectric crystals and the imaged catheters. Since the design of catheters used for these procedures are well established, consideration has been given to the design of the ultrasonic sensor, including the following aspects:

1. The type of piezoelectric material used.
2. The encapsulation procedure.
3. The shape of the transducer.
4. The operating frequency.
5. The activation procedure.

The material selected for use in both the internal and external reference frames must possess superior transmission and reception characteristics in order to properly communicate with each other. Since operating temperatures inside the human body are not a major concern, a higher dielectric material with lower Curie temperature can be employed. Essentially, this provides for an increased ultrasonic output per input volt. The preferred material for this purpose is PZT (lead zirconate titanate).

Since these materials are non-biocompatible, an appropriate encapsulation material is used. The encapsulant must not only be biocompatible, but must also possess an acoustic impedance that does not hinder the ultrasonic wave propagation. This is of key importance for the internal reference frame transducers.

The external reference transducer crystals require an acoustic coupling gel similar to that used for standard B-type ultrasound scans. Omni-directional ultrasound transmission, cylindrical crystals (X1) are used for the internal reference frame. The cylindrical crystals maintain omni-directional radiation patterns while demonstrating excellent transmission and reception characteristics. Externally, larger disk-type or hemispherical crystals are employed for the reference transducers.

Due to the variable software controls of the 3-D tracking and imaging system according to the present invention, the activation frequency can be optimized for maximum performance and efficiency. In the case of the internal reference frame, smaller distances are monitored, therefore higher activation cycle frequencies can be used. The opposite is true of the external reference frame.

Figure 9:
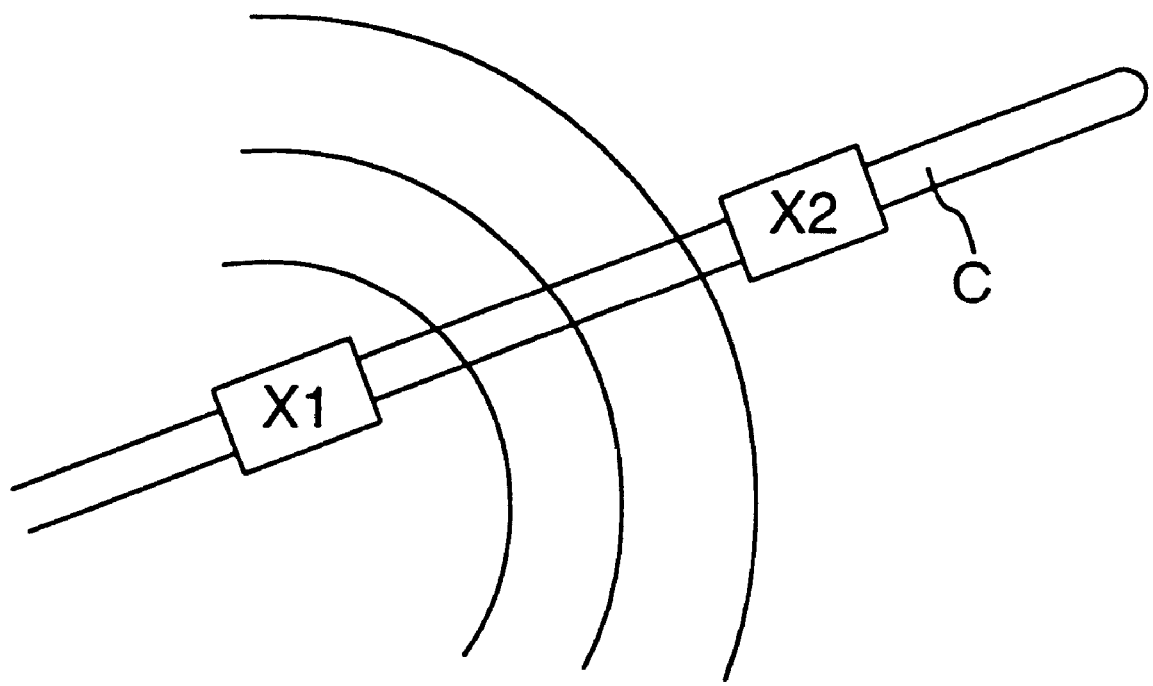
FIG. 9 is a schematic illustration of a catheter guidance system according to a specific implementation of the present invention.

For both reference frames, the method of transducer activation is identical. This process in discussed in detail above with reference to FIG. 6. An insulated conducting wire is used to carry the activation impulse from the control unit to the transducers. In the case of the transducers mounted to the catheter, the signal wires are internally routed through the same sheath as the steering guide wires. Finally, placement of the transducers is contingent upon which reference frame is employed. FIG. 9 illustrates the placement of the cylindrical transducers with respect to the catheter tip, according to the proposed catheter guidance application of the present invention. As can be seen, two ultrasonic crystals (X1, X2) are used on each catheter. This permits the transducers to communicate with each other, as well as to every other internally placed transducer in the region, and also the external reference transducers. By using the information from two concentric transducers mounted on a catheter, vector data can be acquired to illustrate not only the position of the tip, but also the direction. By using three or more transducers, the curvature and 3-D shape of the catheter can be reconstructed.

As can be seen, the two (or more) crystals (X1, X2) are permanently positioned concentrically along the axis of the catheter (C) at an appropriate separation distance for indicating catheter location, orientation and curvature. The piezoelectric material can bet affixed to the catheter with a variety of means, such as a pressfit, bonding, casting or vapor deposition.

Figure 10:
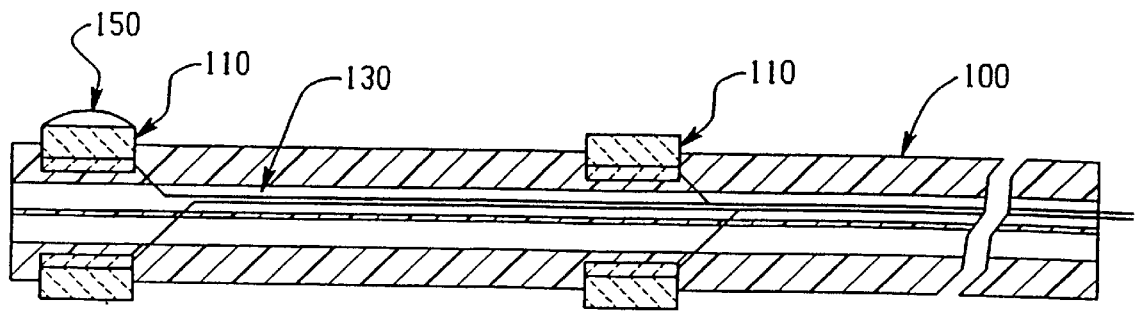
FIG. 10 is a schematic diagram of a multiple transducer catheter according to the preferred embodiment.

One embodiment of the transducer arrangement of FIG. 9, is illustrated in cross-section in FIG. 10. A multi-lumen catheter 100 (or any other suitable probe) is inserted into the body, such that the 3-D shape or extent of the device can be measured or represented, as discussed in greater detail below. As an alternative to using piezoelectric crystals 110, film patches may be used, such as PVDF (polyvinyldifluoride). PVDF is not a crystalline material, but a polymer. It is therefore made in sheets or strips and can be affixed to the catheter as a thin, rectangular patch of film. Its principle of operation is similar to that of PZT. PVDF is essentially a piezoelectric material that can be easily molded into different shapes and configurations.

The catheter 100 can be fabricated from any suitable polymer. A wire or wires (not shown) can pass through one of the lumens of catheter 100, or can be incorporated into the polymer during manufacture. The piezoelectric crystals 110 can be partially or completely embedded into the wall of the catheter 100 or can be affixed to the surface thereof. The crystals are preferably mounted on a suitable lossy backing 130 to which electrical conductors 140 are connected. The crystals 110 can also be provided with a dome-shaped polymer lens 150 affixed thereto.

ii) Tracking of Intravascular Ultrasound Catheters Through Coronary and Through Peripheral Vasculature The tracking of catheters can be extended into the field of intravascular ultrasound. If a vessel has multiple stenoses, it is important to know exactly which one is being imaged with the intravascular ultrasound device. The traditional method involves the injection of contrast agent under fluoroscopy, but this method suffers from the above mentioned risks. The intravascular ultrasound catheter can be easily tracked by using a low frequency transmitter mounted near the imaging head of the catheter. By having a dual display showing the view inside the vessel with the ultrasound, and the position of the imaging area relative to the gross morphology of the vessel on the angiogram, the angiologist can better treat the lesions and reduce the procedural risks to the patient.

iii) Tracking the Biopsy Needles or Biopsy Catheters

The tracking of biopsy catheters is of particular interest, because occasionally the biopsy "bites" are taken from the wrong part of the heart, liver, breast or other tissue or organ to be sampled. In the case of the heart, sometimes a piece of the coronary artery is cut off, or the cardiac valve is damaged, with obvious complications to the patient. By following the path of the biopsy device, using single or multiple angiograms, x-ray images, or ultrasound image sets and real time overlay of the tracked catheter, the biopsy procedure itself can be made more precise and safe.

Needles can also be tracked with ultrasound, such as when cannulating the carotid artery or the femoral artery. An existing unit is available for this procedure, but it relies on having the needle cast a faint shadow in the B-mode ultrasound image. This shadow is not readily visible to the untrained eye, and has obvious limitations in precision. A true 3-D tracking of the needle under real time ultrasound using the principles of the present invention greatly simplifies such procedures.

iv) Guiding of Probes During Stereotactic Surgery

During some delicate surgeries, particularly in the brain, it is important to know the 3-D position of the probe inserted into the head very precisely. The conventional method involves rigidly fastening the patient's head to a stereotactic frame by placing screws and pins into the patient's skull. The patient, with the frame attached, is then imaged using MRI or CAT, and a 3-D reconstruction of the patient's head is created. Pathologic tissue or lesions, such as tumors, are then precisely located relative to the frame. The patient is then taken to the operating room and the required instruments, such as electrodes or ablators, are affixed to guides that allow the instruments to be moved along the specific paths into the patient's head. once the surgical instrument is in place, the lesion can be corrected, destroyed or treated in some way.

This approach is tedious, costly and subject to measurement error in translating the 3-D coordinates from the images to the actual position of the probes within the stereotactic frame.

An alternative to this approach involves the use of a 3-D wand. This instrument consists of an articulating metallic arm that is rigidly affixed to a surgical table. Each of the joints in the arm has an angular position sensor so that the 3-D coordinates of the tip can be calculated from the joint sensors. By matching visual landmarks on the patient's head to the same landmarks on the 3-D image using the probe, the head and the image can be registered with each other. The probe is then used during surgery to hold instruments and guide them into the brain in a manner similar to the stereotactic frame. The advantage of the wand is that it has many more degrees of freedom, and can be held by the surgeon. The disadvantage is that it is very expensive, and very bulky. Also, the position of the probe tip is always only as precise as the original calibration against the patient's head. The patient's head must remain rigidly affixed to the table to which the articulating arm is fixed.

A further application of the 3-D tracking and imaging system according to the present invention involves placing reference transducers anywhere on the patient's head, and several transducers on the probe. As the probe is inserted into the head, its movement relative to the reference transducers can be tracked in real time 3-D. The transducers affixed to the head can be imaged along with the patient, simplifying the registration process, and since they are affixed to the head, movements of the head relative to the operating table do not pose a problem with respect to tracking.

Patients with electrical disturbances of the brain, such as epilepsy, need to have the location of the epilepsy mapped properly prior to surgical intervention. This is done by placing surface electrodes subdurally over the brain. These electrodes, are pushed along the brain through small access holes drilled into the skull, and their location is often difficult to know precisely. By placing transmitter or receiver transducers on the electrode pad, and complementary electrodes on the outside of the skull, according to the principles of the present invention, the motion of the electrodes can be tracked in real time, or can be verified with, images of the brain taken previously. This greatly simplifies the mapping of brain wave activity anomalies.

v) Tracking of Amniocentesis Needles

Another application of the real time tracking system of the present invention in the tracking of biopsy needles for use in the procedure of amniocentesis. A 3-D or 2-D image set of the fetus with the motion of the needle displayed, can increase the precision and speed of the procedure and can prevent injury of the fetus.

vi) Measurement of Cervical Dilation

The onset of labor can be a well controlled process. During the first set of contractions, nurses periodically track the dilation of the cervix. This is done presently by checking the width of the cervix manually. Specifically, one or two fingers are inserted to feel for the head of the fetus, and estimate the degree of cervical dilation. These dilation measurements are done at regular intervals and a time/dilation curve can be plotted. This allows the obstetrician to plan the delivery, as the major contractions come once the rate of cervical dilation increases.

The plotting of such dilation curves can be automated and managed for many mothers in the delivery room by measuring the dilation of the cervix with ultrasonic crystals according to the principles of the present invention.

In this way, a maternity ward can be networked so that progress of many mothers through labor can be monitored remotely by a few nurses at a central station the obstetrician is thus able to predict which patient is due to deliver at what time and can plan his or her activities more precisely.

vii) Assessment of Joint Motion to Look at Stability of the Knee

In some orthopaedic procedures, the stability of the knee needs to be evaluated quantitatively during walking. Knee stability can be assessed through manual manipulation, but only a complex imaging technique can map the motion of the knee during walking. By implanting the transducers of the present invention in the knee, the relative motion of the joints can be measured quantitatively during normal gait, and any surgery to augment ligaments can be better planned.

viii) Assessment of Myocardial Contractility Following Surgery

Following open heart surgery to repair the myocardium or the coronary arteries, the patient has to be monitored to adjust the levels of drugs that are administered. This is referred to as "titration" of drugs. The myocardial contractility is measured with a Swan-Ganz catheter and the drug level adjusted to obtain optimal cardiac function. Unfortunately, the Swan-Ganz catheter measures pressure, which is an indirect measure of contractility and can produce inadequate data.

A pair of transducers, however, provide direct measure of myocardial contractility if attached to the beating ventricle. These transducers can be attached to the myocardium during open chest surgery and can measure the contractility of the heart directly while the chest is open. The leads can then be strung out through the chest wall, and monitoring of myocardial contractility can continue for a few hours or days post operatively. This approach replaces the less precise Swan-Ganz catheter, and can be used to titrate the drugs given to the patient. If the transducers are properly positioned, they can be removed post operatively by pulling on them, in much the same way that pacing electrodes are removed.

The invention has been described with reference to a preferred embodiment. Obviously, modifications and alternatives will occur to others upon reading and understanding of this specification. For instance, it should be appreciated that the transducers may take the form of ultrasonic or electromagnetic transducers. Moreover, the transducers may use time of flight or phase differences as a means of determining position. It is intended to include all such modifications and alterations insofar as they come within the scope of the appended claims or the equivalents thereof.

The invention claimed is:

1. A 3-D tracking and imaging system, comprising:
a plurality of mobile transducer means mounted to an instrument means;
at least one reference transducer means for establishing a reference frame relative to said plurality of mobile transducer means;
coordinate generation means for generating three-dimensional coordinates of the plurality of mobile transducers relative to the reference frame established by the at least one reference transducer means;
imaging modality means for generating one or more digital images of the environment surrounding the instrument means;
image registration means for receiving the three-dimensional coordinates and the one or more digital images, and generating one or more 3-D composites evidencing the position of the plurality of mobile transducer means in relation to the one or more digital images; and
display means adapted for displaying one or more 3-D composites.

2. A system according to claim 1, wherein said plurality of mobile transducer means and said at least one reference transducer means include ultrasonic transducers.

3. A system according to claim 2, wherein said plurality of mobile transducer means and said at least one reference transducer means include electromagnetic transducers.

4. A system according to claim 2 wherein said coordinate generation means comprises:
ultrasound distance measurement means for measuring propagation delays between respective ones of said plurality of mobile transducer means and said at least one reference transducer means;
signal processing means for correcting said measured propagation delays in the event of noise corruption;
a digital sonomicrometer for converting said measured propagation delays into distance measurements and in response generating distance measurement data;
preprocessing means for effecting multidimensional scaling of said distance measurement data to fill in any missing portions of said distance measurement data resulting from signal drop out due to poor signal propagation; and
three-dimensional calculation means for converting said distance measurement data scaled by the preprocessing means into said three-dimensional coordinates.

5. A system according to claim 1 wherein said imaging modality means comprises:
analog-to-digital conversion means for converting analog images into digital images; and
scaling means for scaling said digital images and outputting the scaled digital images to said image registration means.

6. A system according to claim 1 further comprising:
means for receiving an electrocardiogram (ECG) signal;
analog-to-digital conversion means for converting said ECG signal into a digital ECG signal; and
a synchronizing means for receiving said digital ECG signal and in response thereto generating a timing signal for output to said image registration means.

7. A system according to claim 6 further comprising:
user interface means for inputting control instructions and in response to the control instructions generating control signals and transmitting the control signals to said image registration means.

8. A system according to claim 7 further comprising:
means for detecting changes in said signals output from said coordinate generation means three-dimensional coordinates, image modality means, synchronizing means, and user interface means, and in response thereto generating an output signal, and evaluation means for receiving said output signal, determining the existence of any extensive change in said output signal and in response thereto signaling said image registration means.

9. A system according to claim 1, wherein said image registration system arranges said three-dimensional coordinates to form a three-dimensional surface patch defining a moving shape of a bodily structure against which said instrument means is moved.

10. A system according to claim 1, wherein said instrument means is one of either a catheter, a probe, a sensing device, a needle, a scalpel, and a forcep.

11. A system according to claim 1, wherein said coordinate generation means forms an outline of said instrument means.

12. A 3-D tracking and imaging system comprising:
   a plurality of transducer means mounted to an instrument means;
   one or more transducer means located at fixed positions to establish a reference frame relative to the plurality of transducer means mounted to the instrument means;
   coordinate generation means for generating three-dimensional coordinates of the plurality of transducers mounted to an instrument means relative to the reference frame established by the one or more transducer means located at fixed positions;
   imaging modality means for generating image data showing an environment surrounding the instrument means;
   image registration means for registering the three-dimensional coordinates in the image generated by the imaging modality means to generate a 3-D image scene showing the location of the plurality of transducer means mounted to the instrument means in relation to the image data; and
   display means for displaying the 3-D image scene.

13. A system according to claim 12, wherein said transducer means are ultrasonic transducer means having piezoelectric crystals.

14. A system according to claim 13, wherein said coordinate generation means comprises:
   ultrasound distance measurement means for measuring propagation delays of high frequency sound waves emitted by the transducer means and traveling therebetween;
   conversion means for converting the measured propagation delays into distance measurement data indicating the distance between each of said transducer means; and
   3-D calculation means for calculating 3-D coordinates for each of said transducer means from the distance measurement data.

15. A system according to claim 14, wherein said system further comprises:

means for receiving an electrocardiogram (ECG) signal; and
means for generating a timing signal from the ECG signal, said timing signal providing a synchronizing signal to said registration means.

16. A system according to claim 12, wherein said image modality means is comprised of one or more of the following:
   fluoroscopy, MRI, CT, and 3-D ultrasound.

17. A method of tracking an instrument inside a medium within a body and imaging the environment surrounding the instrument in the body, comprising:
   mounting a plurality of transducer means to an instrument means;
   locating at least one transducer means at fixed positions to establish a reference frame relative to the plurality of transducer means mounted to the instrument means;
   generating three-dimensional coordinates of the plurality of transducer mounted to the instrument means relative to the reference frame established by the transducer means located at fixed positions;
   generating image data showing an environment surrounding the instrument means;
   registering the three-dimensional coordinates with the image data to form a 3-D image scene showing the location of the plurality of transducer means mounted to the instrument means relative to the image data; and
   displaying the 3-D image scene.

18. The method according to claim 17, wherein the step of generating three-dimensional coordinates includes:
   measuring progation delays of high frequency sound waves traveling between transducer means;
   converting the measured propagation delays into distance data indicating the distance between each of said transducer means; and
   calculating 3-D coordinates for each of said plurality of transducer means mounted to the instrument means, from the distance data.

19. A method according to claim 17, wherein said method further comprises:
   receiving electrocardiogram (ECG) signals; and
   generating timing signals from the ECG signals to synchronize said step of registering with the step of generating three-dimensional coordinates and generating image data.

20. A method according to claim 17, wherein said step of generating image data includes the step of generating one or more of the following:
   fluoroscopy, MRI, CT and 3-D ultrasound image data.

* * * * *